United States Patent
Numata et al.

(10) Patent No.: US 11,279,941 B2
(45) Date of Patent: Mar. 22, 2022

(54) METHOD FOR INTRODUCING PROTEIN INTO PLANT CELL

(71) Applicant: RIKEN, Wako (JP)

(72) Inventors: Keiji Numata, Saitama (JP); Yoko Horii, Saitama (JP); Takeshi Yoshizumi, Wako (JP); Taku Demura, Saitama (JP); Yutaka Kodama, Tochigi (JP); Takashi Yamamoto, Hiroshima (JP); Tetsushi Sakuma, Hiroshima (JP); Kenji Miura, Ibaraki (JP); Hiroshi Ezura, Ibaraki (JP)

(73) Assignee: RIKEN, Saitama (JP)

( * ) Notice: Subject to any disclaimer, the term of this patent is extended or adjusted under 35 U.S.C. 154(b) by 509 days.

(21) Appl. No.: 16/071,220

(22) PCT Filed: Jan. 19, 2017

(86) PCT No.: PCT/JP2017/001736
§ 371 (c)(1),
(2) Date: Jul. 19, 2018

(87) PCT Pub. No.: WO2017/126604
PCT Pub. Date: Jul. 27, 2017

(65) Prior Publication Data
US 2020/0318125 A1 Oct. 8, 2020

(30) Foreign Application Priority Data
Jan. 20, 2016 (JP) .............................. JP2016-009207

(51) Int. Cl.
*C12N 15/82* (2006.01)
*C07K 14/00* (2006.01)
*C12N 9/22* (2006.01)

(52) U.S. Cl.
CPC ........ *C12N 15/8202* (2013.01); *C07K 14/001* (2013.01); *C12N 9/22* (2013.01); *C12N 2310/20* (2017.05)

(58) Field of Classification Search
None
See application file for complete search history.

(56) References Cited

U.S. PATENT DOCUMENTS

2012/0244569 A1   9/2012  Samuel et al.
2015/0218569 A1*  8/2015  Numata .................... C07K 7/06
                                                      435/468

FOREIGN PATENT DOCUMENTS

| EP | 3115456 A1 | 1/2017 |
| JP | 2014-511678 A | 5/2014 |
| WO | WO 2013/129698 A1 | 9/2013 |
| WO | WO 2015/133652 A1 | 9/2015 |

OTHER PUBLICATIONS

Change et al. Cellular internalization of fluorescent proteins via arginine-rich intracellular delivery peptide in plant cells. Plant Cell Physiol. Mar. 2005;46(3):482-8. Epub Feb. 2, 2005. (Year: 2005).*
Ng et al. Intracellular Delivery of Proteins by Fusion Peptide in Living Plant. The 33rd Meeting of the Japanese Society for Plant Cell & Molecular Biology, Aug. 10-12, 2015, p. 89, 10B-03. (Year: 2015).*
Ng et al. Intracellular Delivery of Proteins via Fusion Peptides in Intact Plants. PLOS ONE, Apr. 21, 2016, 11(4):e0154081, 19 pages. (Year: 2016).*
Lakshmanan et al. Rapid and Efficient Gene Delivery into Plant Cells Using Designed Peptide Carriers. Biomacromolecules, 2013, 14:10-16. (Year: 2013).*
Eggenberger et al. Using the peptide BP100 as a cell-penetrating tool for the chemical engineering of actin filaments within living plant cells. Chembiochem. Jan. 3, 2011;12(1):132-7. (Year: 2011).*
Chang et al. Noncovalent protein transduction in plant cells by macropinocytosis. New Phytol. 2007;174(1):46-56. (Year: 2007).*
Filoti et al. Comparative Study of Analytical Techniques for Determining Protein Charge. J. Pharm. Sci. Jul. 2015;104(7):2123-31. Epub Apr. 24, 2015. (Year: 2015).*
International Search Report dated Feb. 21, 2017, in PCT/JP2017/001736.
Chang et al. "Cellular Internalization of Fluorescent Proteins via Arginine-rich Intracellular Delivery Peptide in Plant Cells," Plant Cell Physiol., 2005, 46(3):482-488.
Esvelt et al., "Genome-scale engineering for systems and synthetic biology," Molecular Systems Biology, 2013, 9, 641, 17 pages.
Lakshmanan et al., "Rapid and Efficient Gene Delivery into Plant Cells Using Designed Peptide Carriers," Biomacromolecules, 2013, 14:10-16.
Liang et al., "Rapid and highly efficient mammalian cell engineering via Cas9 protein transfection," Journal of Biotechnology, 2015, 208:44-53.
Mahmood-ur-Rahman et al.,. "RNA interference : The story of gene silencing in plants and humans," Biotechnology Advances, 2008, 26:202-209.
Ng et al. "Intracellular Delivery of Proteins by Fusion Peptide in Living Plant," The 33rd Meeting of the Japanese Society for Plant Cell & Molecular Biology, Aug. 10-12, 2015, p. 89, 10B-03.
Ng et al., "Intracellular Delivery of Proteins via Fusion Peptides in Intact Plants," PLOS ONE, Apr. 21, 2016, 11(4):e0154081, 19 pages.

(Continued)

*Primary Examiner* — Cynthia E Collins
(74) *Attorney, Agent, or Firm* — Foley & Lardner LLP

(57) ABSTRACT

It is an object of the present invention to provide a method for introducing a protein into a plant, which is simple and extensively applicable to various types of plant cells and proteins. The above object is achieved by the present invention to provide a complex comprising a protein of interest to be introduced into a target plant cell and a carrier peptide, a method for introducing a protein of interest into a target plant cell using the complex, and a kit comprising a protein of interest to be introduced into a target plant cell and a carrier peptide.

10 Claims, 14 Drawing Sheets
Specification includes a Sequence Listing.

(56) References Cited

OTHER PUBLICATIONS

Nielsen et al., "Horizontal gene transfer from transgenic plants to terrestrial bacteria—a rare event?", FEMS Microbiology Reviews, 1998, 22:79-103.

Numata et al., "Direct introduction of neomycin phosphotransferase II protein into apple leaves to confer kanamycin resistance," Plant Biotechnology, 2016, 33(5):403-407.

Sarker et al., "Intracellular Delivery of Universal Proteins Using a Lysine Headgroup Containing Cationic Liposomes: Deciphering the Uptake Mechanism," Molecular Pharmaceutics, 2014, 11:164-174.

Schwarze et al., "In Vivo Protein Transduction: Delivery of a Biologically Active Protein into the Mouse," Science, Sep. 3, 1999, 285:1569-1572.

Chang et al., "Noncovalent protein transduction in plant cells by micropinocytosis," New Phytol., 2007, 174:46-56.

\* cited by examiner

Fig. 10
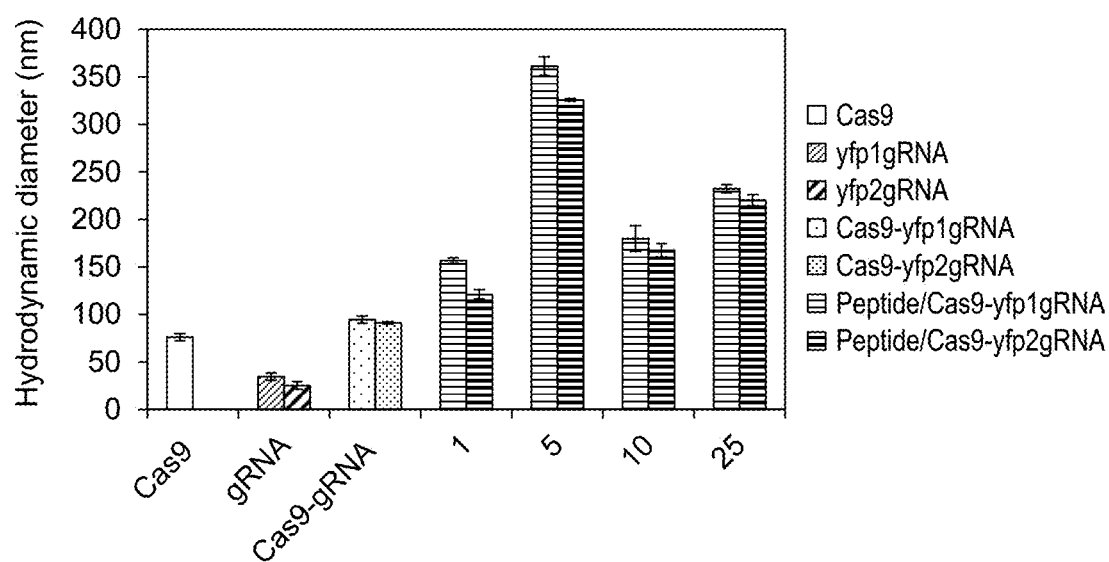
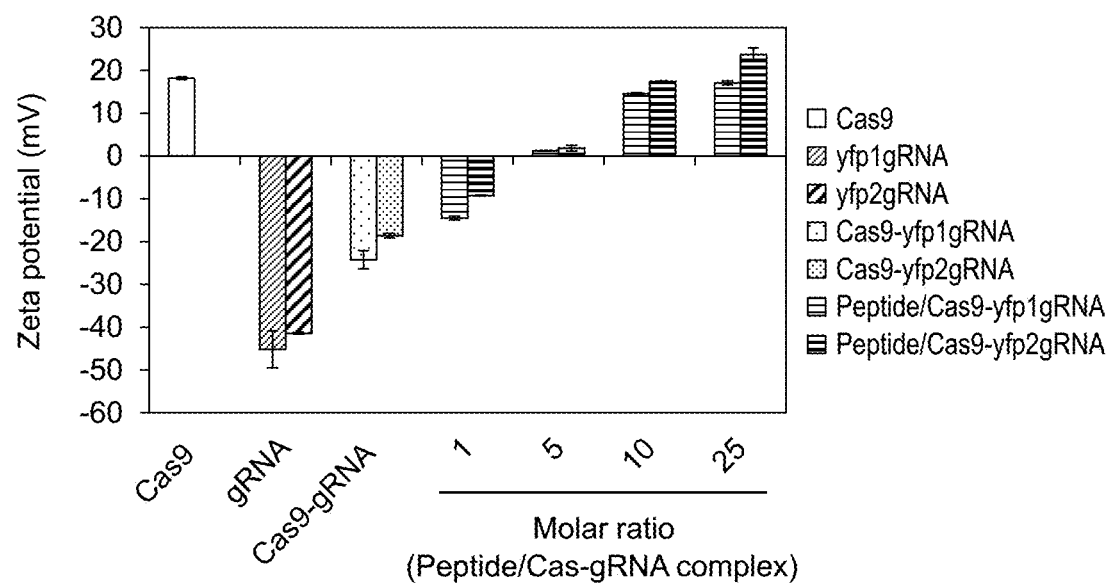

Fig. 12
(a)
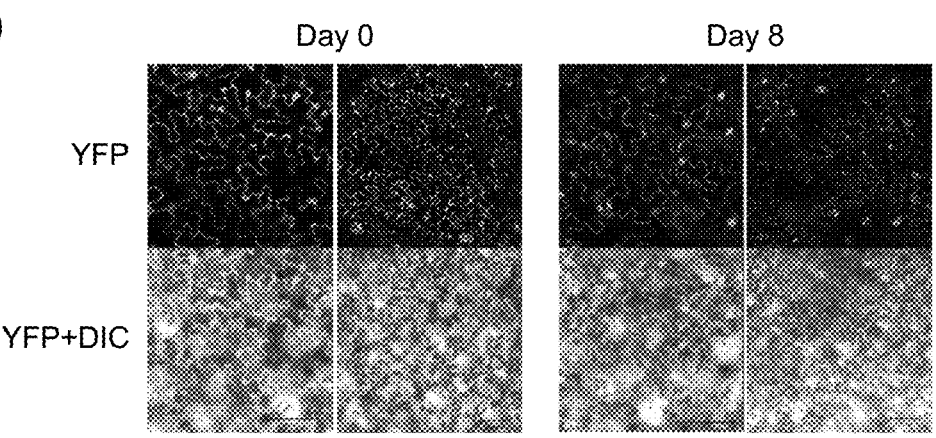
(b)
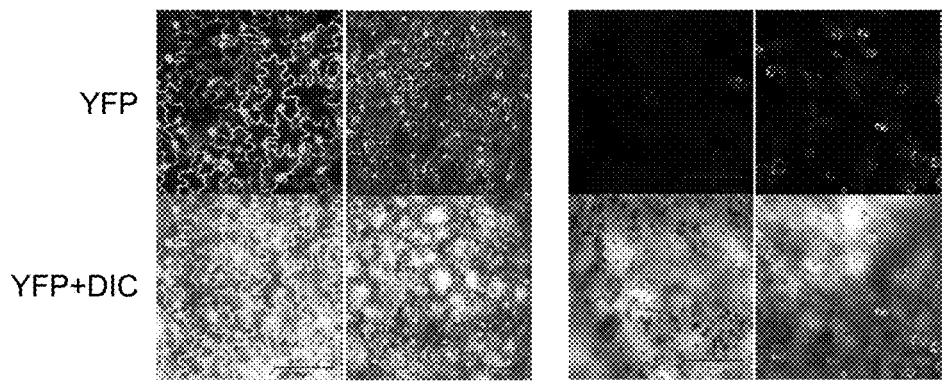

Fig. 13
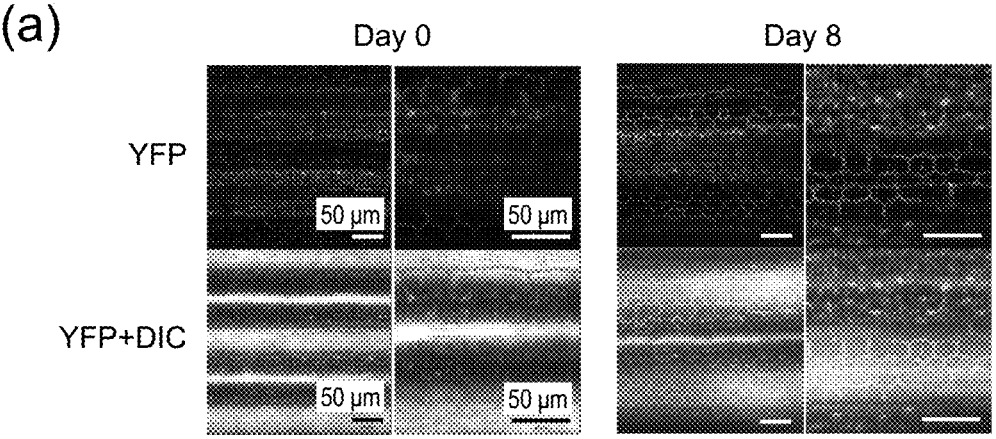
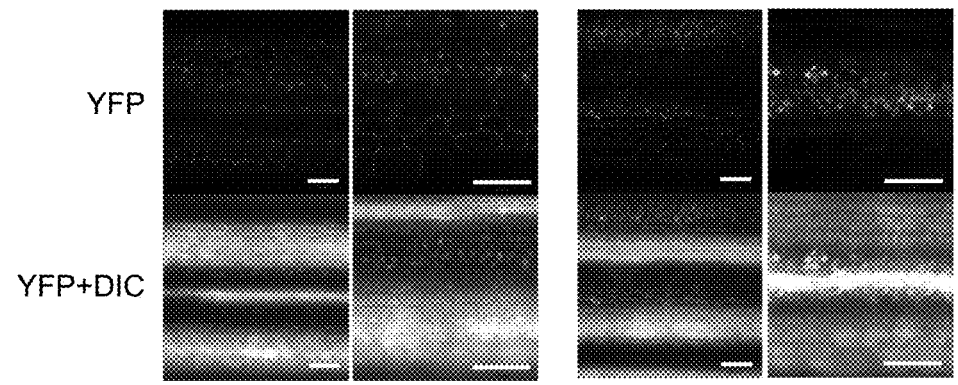

METHOD FOR INTRODUCING PROTEIN INTO PLANT CELL

CROSS-REFERENCE TO RELATED APPLICATIONS

This application is a National Stage application of PCT/JP2017/001736, filed Jan. 19, 2017, which claims priority from Japanese application JP 2016-009207, filed Jan. 20, 2016.

TECHNICAL FIELD

The present invention relates to a carrier peptide/protein complex comprising a protein of interest to be introduced into a target plant cell and a carrier peptide, a method for producing the complex, a method for introducing a protein of interest into a target plant cell using the complex, and a kit comprising a protein of interest to be introduced into a target plant cell and a carrier peptide.

BACKGROUND ART

Genetic recombination is a plant breeding technique that has been extensively employed to improve crop productivity and enhance adaptability. Examples of properties that can be improved by such technique include the yield, nutritional quality, herbicide resistance, drought resistance, pesticide resistance, and virus resistance. Genetically modified plants can be used as, for example, living factories for production of hormones, vaccines, aromatic chemicals, and colorants.

At present, genetically modified plants are primarily produced via DNA transformation, such as *Agrobacterium* transformation, protoplast transformation, or a microparticle gun etc. Such DNA transformation techniques, however, have some underlying problems, for example, unexpected incorporation of a foreign DNA into the plant nuclear genome or organelle genome that destructs an endogenous gene, or incorporation of antibiotic-resistance caused by pathogenic bacteria in soil that mediates horizontal gene transfer (Non Patent Literature 1). In order to prepare and make use of modified plants with higher safety, accordingly, it is essential to develop a method, which is simple and extensively applicable to various types of plant cells and proteins. As such a technique, in recent years, a non-transgenic direct protein delivery system has drawn attention. A non-transgenic direct protein delivery system in animals has been extensively developed in vitro and in vivo (Non Patent Literatures 2 to 4). In the case of plants, however, development of such technique had been considered difficult because of that plants have thick and strong cell walls, proteins are generally macromolecules, and plant cells have proteolytic activity, and other reasons. So far, accordingly, it has been difficult to safely modify many plants and produce an improved new variety of a plant.

In recent years, genome editing techniques, such as TALEN, the CRISPR/Cas9 system, and ZFN, have also drawn attention. Genome-editing techniques enable genetic modification at the genome level, such as knock-out of any gene in the genome and knock-in of a foreign gene into the genome (Non Patent Literature 5). While such genome editing techniques are excellent in being able to produce plants with an inheritable genetic modification via a single modification treatment, it is difficult to produce plants with a non-inheritable and transient genetic modification. An RNA interference (RNAi) technique such as siRNA is known in the art as another technique to inhibit gene expression (Non Patent Literature 6). Since effects of the RNAi technique are limited to a single to several generations in many cases, it is often convenient in terms of preparing transient genetically modified plants. The RNAi technique, however, utilizes the inhibitory mechanism at the mRNA level, but it is not a modification technique at the genome level unlike the genome editing technique. Accordingly, a novel technique that modifies a particular gene at the genome level and can limit the effects to a single generation is demanded.

CITATION LIST

Non Patent Literature

Non Patent Literature 1: Nielsen K. M. et al., 1998, FEMS Microbiol. Rev., 22, pp. 79-103
Non Patent Literature 2: Liang X. et al., 2015, J. Biotechnol., 208, pp. 44-53
Non Patent Literature 3: Sarker S. R. et al., 2014, Mol. Pharm., 11, pp. 164-174
Non Patent Literature 4: Schwarze S. R. et al., 1999, Science, 285, pp. 1569-1572
Non Patent Literature 5: Esvelt K M. et al., 2013, Mol. Syst. Biol., 9, 641
Non Patent Literature 6: Mahmood-ur-Rahman et al., Biotechnol. Adv., 26, 3, pp. 202-209

SUMMARY OF INVENTION

Technical Problem

An object of the present invention is to provide a method for introducing a protein into a plant, which is simple and extensively applicable to various types of plant cells and proteins, and to provide a method for producing a transient or inheritable genome-modified plant by introducing a protein into a plant.

Solution to Problem

The present inventors constructed a fusion peptide comprising a cell-penetrating sequence and a polycationic sequence in combination as a carrier peptide to deliver a protein of interest into a plant cell. They discovered that a carrier peptide/protein complex which can introduce a protein of ino a plant cell with excellent efficiency can be formed by mixing the carrier peptide with the protein of interest to be introduced into the plant cell, and thus have completed the present invention.

Specifically, the present invention encompasses the following aspects.

(1) A carrier peptide/protein complex comprising:
a carrier peptide comprising a cell-penetrating sequence and a polycationic or polyanionic sequence; and
a protein of interest to be introduced into a target plant cell.
(2) The complex according to (1), wherein the cell-penetrating sequence is KKLFKKILKYL (SEQ ID NO: 1).
(3) The complex according to (1) or (2), wherein the polycationic sequence comprises at least three amino acid residues selected from lysine (K), arginine (R), and histidine (H).
(4) The complex according to (3), wherein the polycationic sequence comprises 3 to 20 KH repeats or a sequence of 3 to 20 contiguous Ks.

(5) The complex according to (1) or (2), wherein the polyanionic sequence comprises at least three amino acid residues selected from aspartic acid (D) and glutamic acid (E).
(6) The complex according to (4), wherein the carrier peptide comprises the amino acid sequence of KKLFKKIL-KYLKKLFKKILKYLKKKKKKKK (SEQ ID NO: 23) or KKLFKKILKYLKHKHKHKHKHKHKHKH (SEQ ID NO: 24).
(7) The complex according to (1) or (2), wherein the complex has an average hydrodynamic diameter of 150 to 700 nm.
(8) The complex according to any of (1) to (7), wherein the protein of interest has a molecular weight of 5 kDa to 200 kDa.
(9) The complex according to any of (1) to (8), wherein the protein of interest is TALEN-L or TALEN-R, ZFN, or Cas9.
(10) A method for producing the carrier peptide/protein complex according to any of (1) to (9) comprising:
 a step of mixing a carrier peptide with a protein of interest to form the carrier peptide/protein complex according to any of (1) to (9).
(11) A method for introducing a protein of interest into a target plant cell comprising:
 a step of mixing a carrier peptide with protein of interest to form the carrier peptide/protein complex according to any of (1) to (9); and
 a step of bringing the resulting complex into contact with the target plant cell.
(12) A method for producing a genome-modified plant cell comprising:
 a step of mixing a carrier peptide with a protein of interest to be introduced into a target plant cell to form a carrier peptide/protein complex; and
 a step of bringing the resulting complex into contact with the target plant cell,
 wherein the carrier peptide comprises a cell-penetrating sequence and a polycationic or polyanionic sequence, and
 wherein the protein of interest is TALEN-L or TALEN-R, ZFN, or Cas9.
(13) A method for producing a genome-modified plant comprising:
 a step of producing a genome-modified plant from the genome-modified plant cell obtained by the method according to (12).
(14) A genome-modified plant cell obtained by the method according to (12) or a genome-modified plant obtained by the method according to (13).
(15) The method according to any of (10) to (13), wherein the carrier peptide is mixed with the protein of interest at a molar ratio of 2:1 to 25:1 in the step of forming a complex.
(16) The method according to any of (10) to (13) and (15), wherein the target plant cell is obtained from a plant of Gramineae, Brassicaceae, Solanaceae, Leguminosae, or Salicaceae.
(17) An agent for introducing a protein of interest into a target plant cell consisting of a carrier peptide comprising a cell-penetrating sequence and a polycationic or polyanionic sequence.
(18) A kit for introducing a protein of interest into a target plant cell comprising: a protein of interest to be introduced into a target plant cell; and the carrier peptide as defined in any of (1) to (6).
(19) The kit according to (18), wherein the protein of interest is TALEN-L or TALEN-R, ZFN, or Cas9.

This description includes part or all of the content as disclosed in the description and/or drawings of Japanese Patent Application No. 2016-009207, to which the present application claims priority.

Advantageous Effects of Invention

The present invention provides a method for introducing a protein into a plant cell, which is simple and extensively applicable to various types of plant cells and proteins. According to this method of introduction, varieties of many plants can be safely and readily improved. In addition, the present invention can modify a particular gene at the genome level and can limit the gene modification effects to transient effects.

BRIEF DESCRIPTION OF DRAWINGS

FIG. 3 (a) shows the results of SDS-PAGE of a total crude protein extracted from an *Arabidopsis thaliana* leaf 6 hours after being contacted with the $(BP100)_2K$/BSA-RhB complex and the $BP100(KH)_9$/BSA-RhB complex prepared by mixing the carrier protein with BSA-RhB at a molar ratio of 1 to 25. The fluorescence band of BSA-RhB was detected using a fluorescence image analyzer. A negative control is a total crude protein extracted from an *Arabidopsis thaliana* leaf that not being contacted with the complex. A positive control represents the results of BSA-RhB directly subjected to SDS-PAGE. FIGS. 3 (b) and (c) shows a bar chart showing the amount (%) of BSA-RhB extracted from an *Arabidopsis thaliana* leaf after being contacted with the $(BP100)_2K_8$/BSA-RhB complex, and $BP100(KH)_9$/BSA-RhB, respectively. All the data are indicated as the mean S.D. of the three tests, and the symbol "*" indicates a statistically significant difference, compared with contacting the complex at a peptide molar ratio of 1 (Turkey's HSD test, $p<0.05$).

Figure 4:
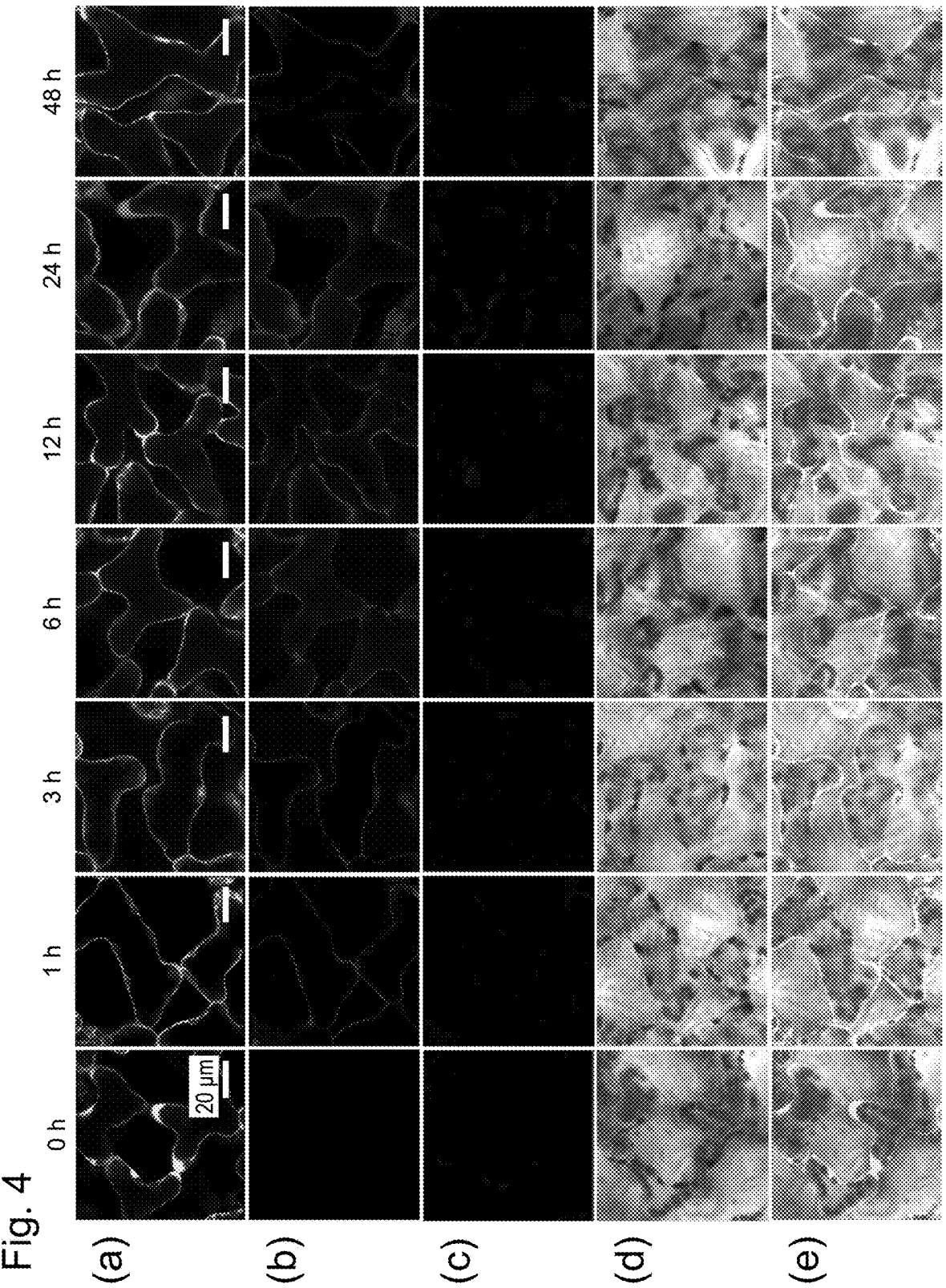
FIG. 4 shows the results of overtime analysis of BSA-RhB delivery by the $(BP100)_2K$/BSA carrier peptide complex comprising the carrier peptide and the protein at a molar ratio of 10:1 with the elapse of time. An YFP-expressing *Arabidopsis thaliana* leaf was contacted with the $(BP100)_2K$/BSA-RhB complex for a given period of time (0, 1, 3, 6, 12, 24, and 48 hours) and then observed by confocal laser scanning microscopy (CLSM). (a) shows YFP (yellow fluorescent protein) expressed in the cytosol of an YFP-expressing *Arabidopsis thaliana* leaf, (b) shows RhB fluorescence derived from the introduced BSA-RhB, (c) shows autofluorescence emitted by the cell plastid (chloroplast), (d) shows the results of the light field, and (e) shows merged images of 4 images (a) to (d). A scale bar is 20 μm.

correspond to (a) to (e) in FIG. 4, provided that (b) shows RhB fluorescence derived from the introduced ADH-RhB.

Figure 6:
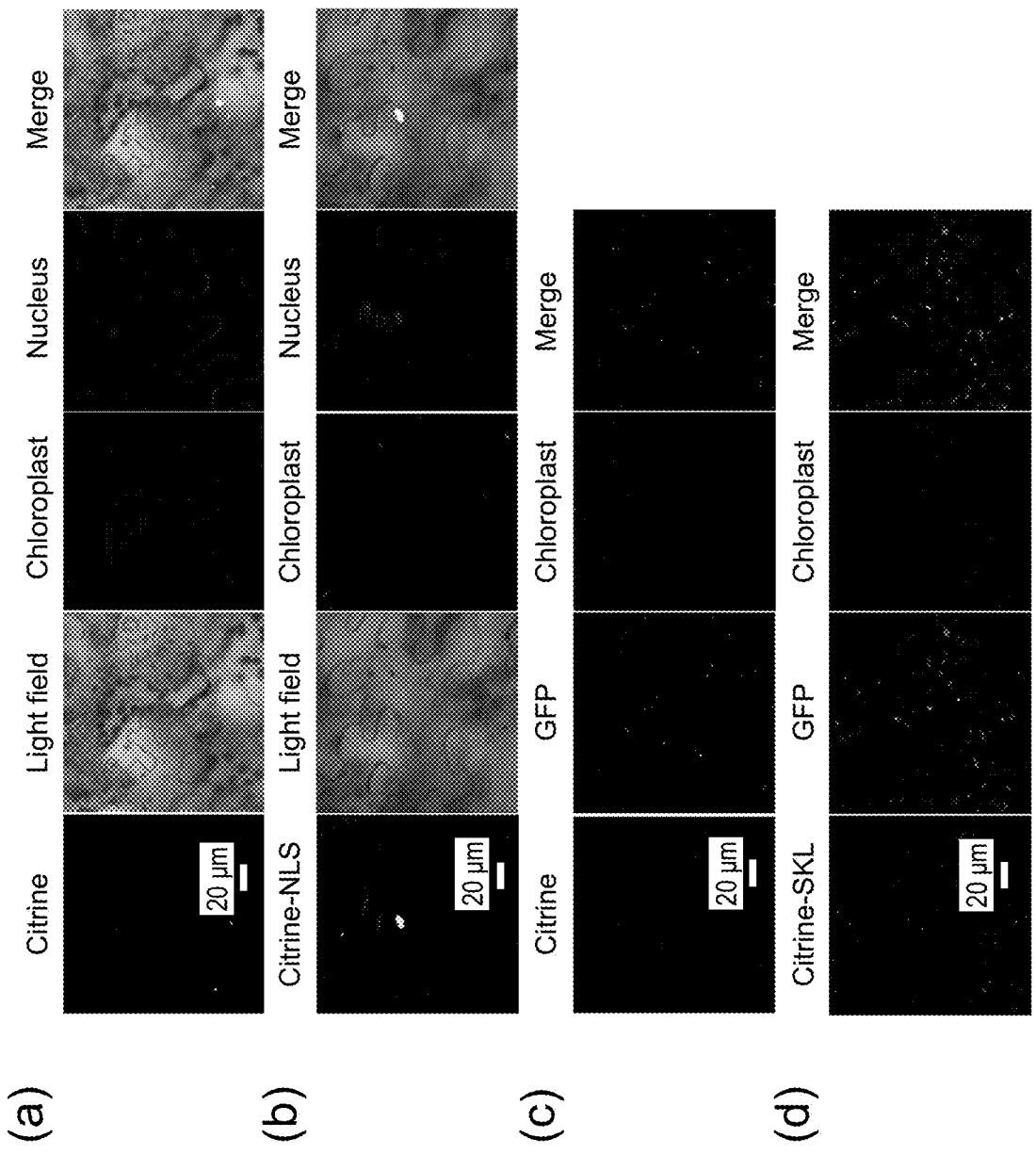

FIG. 6 shows the results of analysis of subcellular localization of the introduced protein via CLSM. (a) and (b) show the results of an *Arabidopsis thaliana* leaf into which the (BP100)$_2$K/citrine complex as a negative control and (BP100)$_2$Ks/citrine-NLS complex were introduced, respectively. The nucleus was stained with DAPI (4'6-diamidino-2-phenylindole). (c) and (d) show GFP-PTS-expressing *Arabidopsis thaliana* leaf into which the (BP100)$_2$K/citrine complex as a negative control and (BP100)$_2$K/citrine-PTS complex were introduced, respectively. Peroxisome was visualized by GFP fluorescence. A scale bar is 20 μm.

Figure 7:
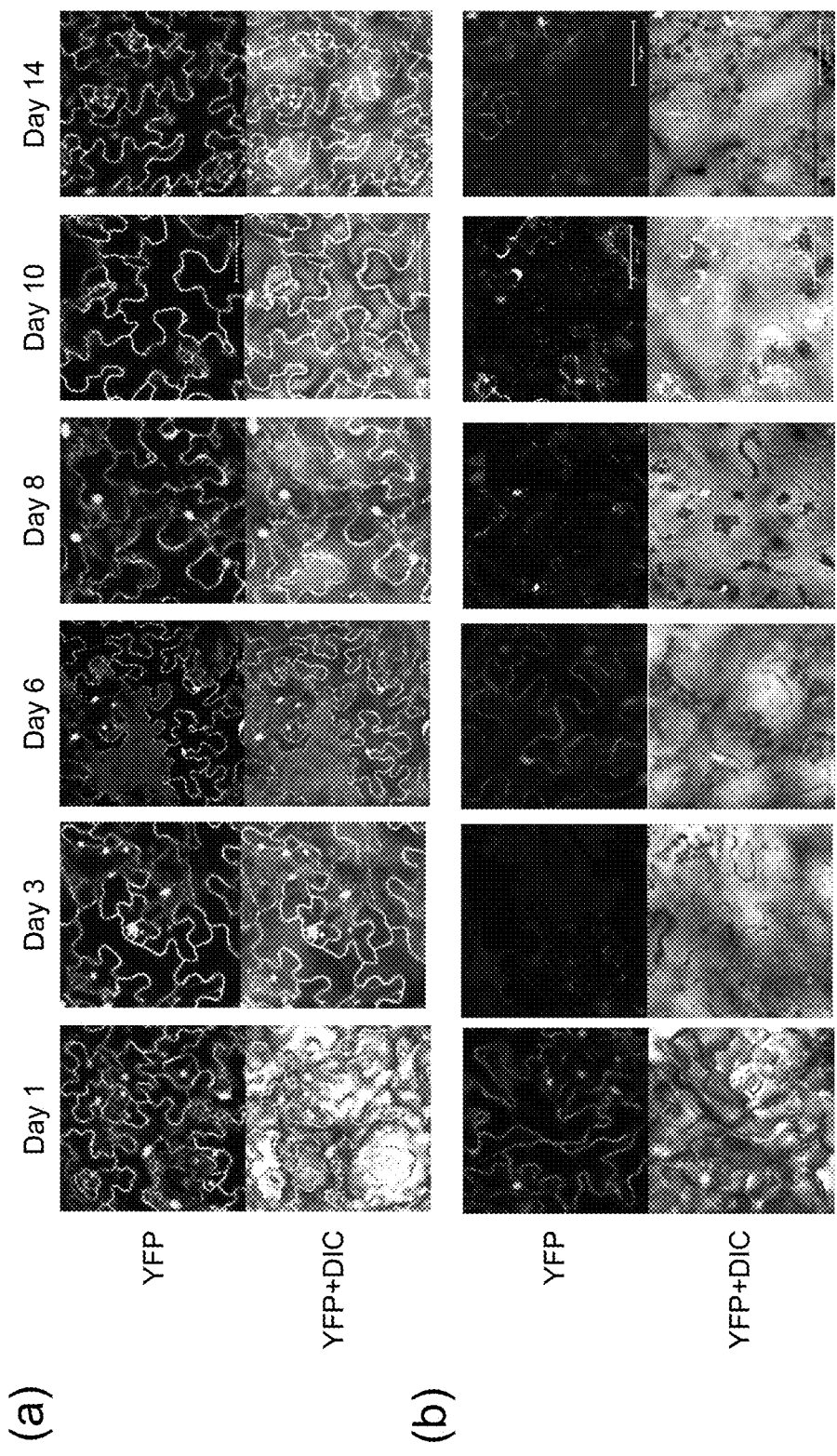

FIG. 7 shows the results of observation via CLSM of an YFP-expressing *Arabidopsis thaliana* leaf into which TALEN-YFP was introduced (1, 3, 6, 8, 10, and 14 days after the contact). (a) shows the results when adding water as a control and (b) shows the results when introducing the carrier peptide/TALEN-YFP complex. "YFP" indicates fluorescence emitted by YFP, and "YFP+DIC" shows a merged image of the YFP fluorescence image and the differential interference contrast image.

Figure 8:
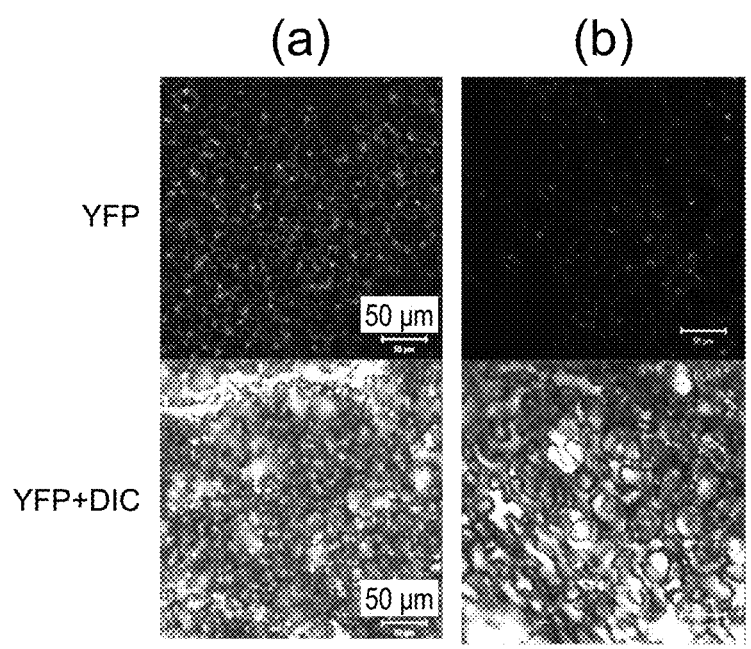

FIG. 8 shows the results of observation via CLSM of an YFP-expressing poplar leaf 2 days after being contacted with TALEN-YFP. (a) shows the results when introducing (BP100)$_2$K$_8$ as a control and (b) shows the results when introducing the carrier peptide/TALEN-YFP complex. "YFP" indicates fluorescence emitted by YFP, and "YFP+DIC" shows a merged image of the YFP fluorescence image and the differential interference contrast image. A scale bar is 50 μm.

Figure 9:
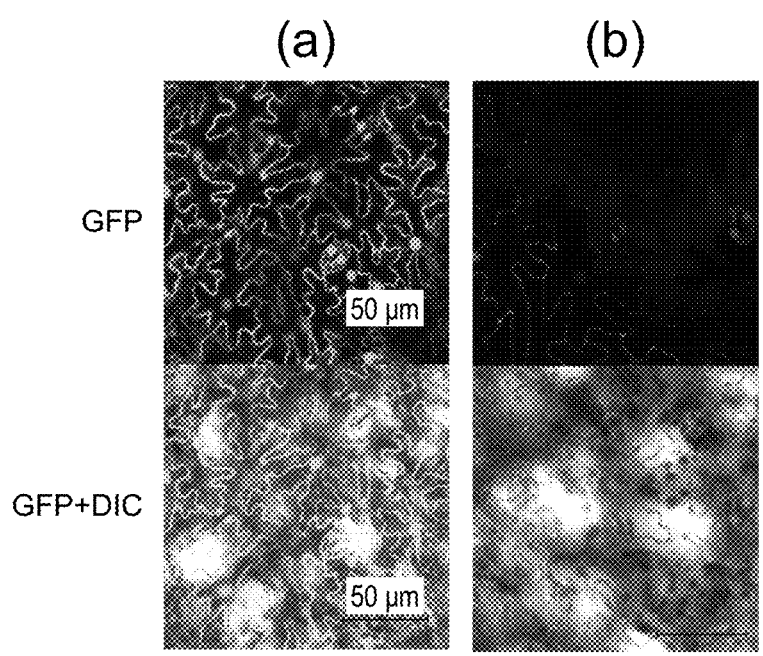

FIG. 9 shows the results of observation via CLSM of a GFP-expressing tomato (Micro-tom) leaf 3 days after introducing TALEN-GFP. (a) shows the results when introducing (BP100)$_2$K$_8$ as a control and (b) shows the results when introducing the carrier peptide/TALEN-GFP complex. "GFP" indicates fluorescence emitted by GFP, and "GFP+DIC" shows a merged image of the GFP fluorescence image and the differential interference contrast image. A scale bar is 50 μm.

FIG. 10 shows charts showing the hydrodynamic diameters (a) and the zeta potentials (b) of Cas9, gRNA, Cas9-gRNA, and Cas9-gRNA-peptide complexes (a peptide/Cas9-gRNA molar ratio: 1, 5, 10, or 25), regarding Yfp1 gRNA and Yfp2gRNA.

Figure 11:
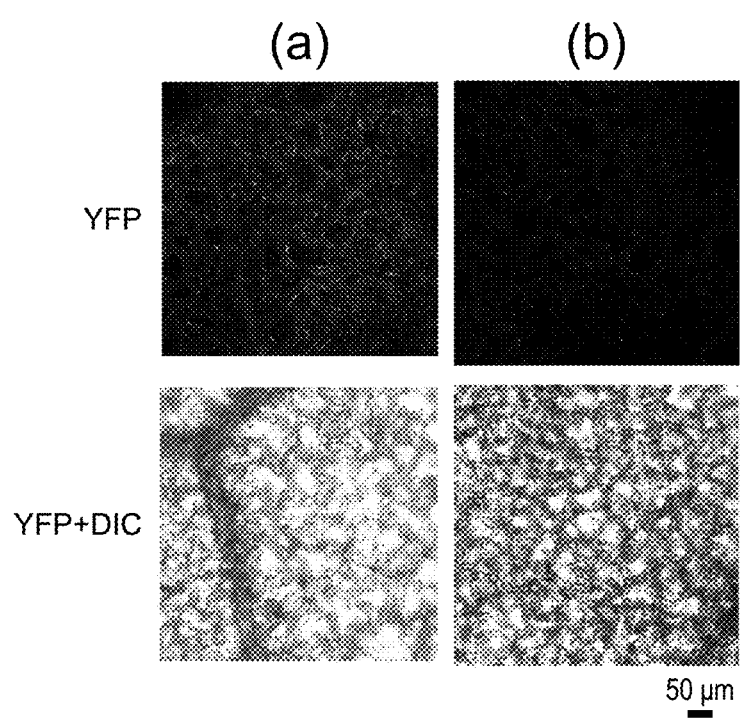

FIG. 11 shows the results of observation via CLSM of an YFP-expressing *Arabidopsis thaliana* leaf 6 days after introducing guide RNAs targeting Cas9 and YFP. (a) shows the results when introducing water as a control and (b) shows the results when introducing the carrier peptide/Cas9-gRNA complex. "YFP" indicates fluorescence emitted by YFP, and "YFP+DIC" shows a merged image of the YFP fluorescence image and the differential interference contrast image. A scale bar is 50 μm.

FIG. 12 shows the results of observation via CLSM of a GFP-expressing microtomato 0 and 8 days after introducing guide RNAs targeting Cas9 and YFP. (a) shows the results when introducing the carrier peptide alone as a control and (b) shows the results when introducing the carrier peptide/Cas9-gRNA complex. "YFP" indicates fluorescence emitted by YFP, and "YFP+DIC" shows a merged image of the YFP fluorescence image and the differential interference contrast image. A scale bar is 50 μm.

FIG. 13 shows the results of observation via CLSM of a GFP-expressing rice 0 and 8 days after introducing of guide RNAs targeting Cas9 and YFP. (a) shows the results when introducing the carrier peptide alone as a control and (b) shows the results when introducing the carrier peptide/Cas9-gRNA complex. "YFP" indicates fluorescence emitted by YFP, and "YFP+DIC" shows a merged image of the YFP fluorescence image and the differential interference contrast image. A scale bar is 50 μm.

Figure 14:
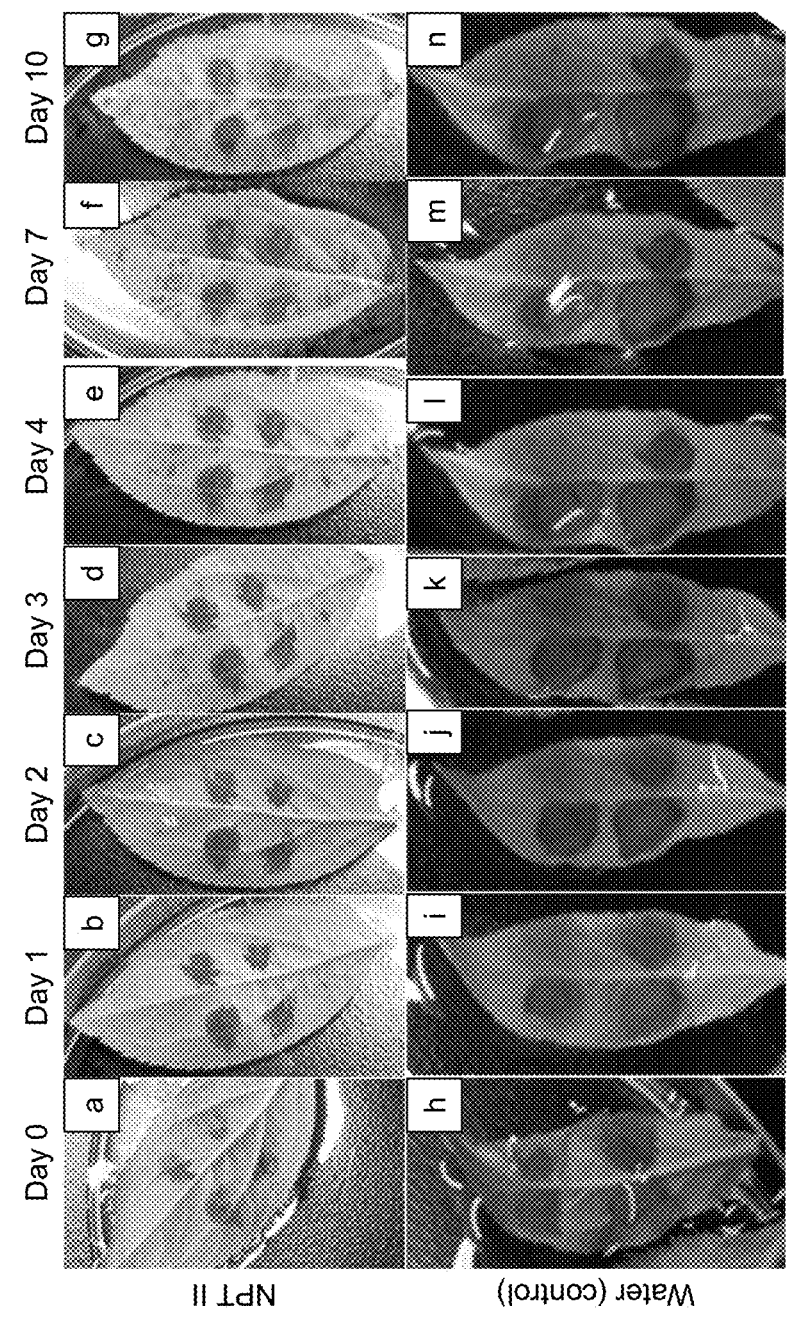

FIG. 14 shows the results of observation of an apple leaf impregnated with the NPT II/carrier peptide complex (MPT II) or water (control) that were further impregnated with a 75 mg/mL kanamycin solution for 0 to 10 days.

DESCRIPTION OF EMBODIMENTS

<Carrier Peptide/Protein Complex>

In one aspect, the present invention relates to a carrier peptide/protein complex comprising a protein of interest to be introduced into a target plant cell, and a carrier peptide comprising a cell-penetrating sequence and a polycationic or polyanionic sequence.

1. Protein of Interest to be Introduced into Target Plant Cell

Types and properties of "the protein of interest to be introduced into the target plant cell" (also simply referred to as "the protein of interest" hereinafter) as used herein are not particularly limited. For example, the protein of interest may be any of a structural protein, a secretory protein, an enzyme, an antibody, a label protein, a regulatory protein, and a selection marker protein (e.g., neomycin phosphotransferase (NPT) II providing kanamycin resistance or β-lactamase providing ampicillin resistance). Specific examples include bovine serum albumin (BSA), alcohol dehydrogenase (ADH), and modified YFP, such as citrine and NPT II. A preferable example of the protein of interest is a genome-editing protein. The term "genome editing" or "genome modification" used herein refers to specific cleavage or editing of a target site in the genome, for example, knock-in and knock-out of a particular gene for a wild-type genome. Examples of genome-editing proteins include the transcription activator-like effector nuclease (TALEN), the CRISPR associated protein 9 (Cas9), and the zinc finger nuclease (ZFN), preferably, TALEN and Cas9. Two or more protein of interests can be introduced simultaneously into a target plant cell. For example, a selection marker protein and another protein of interest are simultaneously introduced into a target plant cell, so that cells into which the protein was introduced can be selected based on the selection marker.

The term "transcription activator-like effector nuclease (TALEN)" used herein refers to a protein comprising a nucleic acid binding domain (i.e., a transcription activator-like effector (TALE)) and a nuclease domain. The transcription activator-like effector (TALE) is a protein derived from bacteria such as *Xanthomonas* sp., which comprises a plurality of, for example, 10 to 30 or 13 to 25, and preferably 15 to 20 repeat sequences consisting of about 34 amino acids. Each repeat sequence comprises 2 amino acid residues at positions 12 and 13 (repeat variable diresidues (RVD)) specific to a nucleotide in the target nucleic acid sequence. An example of a repeat sequence is LTPEQVVAIASHDGGKQALETVQRLLPVLCQAHG (SEQ ID NO: 26). (provided that the sequences at positions 12 and 13 in the repeat sequence may vary depending on a target nucleotide sequence. Thus, the repeat sequence may be LTPEQVVAIASXXGGKQALETVQRLLPVLCQAHG (SEQ ID NO: 27), provided that amino acids at positions 12 and 13 are defined depending on the binding to the target nucleotides). Also, an amino acid sequence in which one or a plurality of amino acid residues are substituted, inserted, and/or deleted in the amino acid sequence of SEQ ID NO:

26 or 27, and maintaining binding specificity to DNA can be used. The term "a plurality of" used herein refers to, for example, 10 or less, 9 or less, 8 or less, 7 or less, 6 or less, preferably 5 or less or 4 or less, and more preferably 3 or less or 2 or less. Examples of RVDs that specifically recognize nucleotides include: HD that recognizes C; NG that recognizes T; NI that recognizes A; NN that recognizes G or A; and NS that recognizes A, C, G, or T. See, for example, WO 2011/072246, regarding the details of RVD and recognition sequences thereof. In another embodiment, amino acids at positions 12 and 13 of RVD may be substituted with other amino acid residues, so as to enhance specificity thereof to nucleotides A, T, C, and G.

A nuclease domain in TALEN preferably has endonuclease activity (e.g., I-TevI, ColE7, NucA, and FokI, preferably, FokI). The amino acid sequences of these domains are known to a person skilled in the art. For example, FokI comprises the amino acid sequence of SEQ ID NO: 25. As nuclease domains, a polypeptide comprising an amino acid sequence in which one or a plurality of amino acid residues are substituted, inserted, an/or deleted in the amino acid sequence of SEQ ID NO: 25, and having endonuclease activity as well as a polypeptide comprising an amino acid sequence having 70% or higher, 80% or higher, for example, 90% or higher, 95% or higher, 97% or higher, 98% or higher, or 99% or higher identity with the amino acid sequence of SEQ ID NO: 25, and having endonuclease activity may be used. The sequence identity is calculated using software that computes the identity among a plurality of sequences (e.g., FASTA, DANASYS, and BLAST) at default settings. As a nuclease domain, FokI that was modified to enhance specificity can be used (e.g., Doyon Y. et al., Nature Methods, 2010, 8 (1), pp. 74-79; and Szczepek M. et al., Nature Biotechnology, 2007, 25 (7), pp. 786-793). FokI is activated by forming a dimer (Bitinaite et al., Proc. Natl. Acad. Sci. U.S.A., 1998, 95, pp. 10, 570-10, 575). When FokI is used as a nuclease domain, accordingly, it is activated only when it binds to both of the double strands of the target DNA sequence. In this case, two types of TALENs (i.e., TALEN-Left (TALEN-L) and TALEN-Right (TALEN-R)) are necessary, in order for TALEN to have nuclease activity, and TALEN-L and TALEN-R bind to each of the double strands of the target DNA sequence via, for example, 8 to 40, 10 to 34, or 12 to 32 spacer sequences. See, for example, WO 2011/072246, regarding the details of the method for producing and using TALEN.

The "CRISPR associated protein 9 (Cas9)" used herein is a protein that constitutes the clustered regularly interspaced short palindromic repeats (Cas9/CRISPR) system together with guide RNA. The Cas9/CRISPR system makes use of sequence-specific DNA binding and cleavage, and sequence specificity thereof depends on guide RNA (Hendel A. et al., Nature Biotechnology, 2015, 33, pp. 985-989). An origin of the Cas9 protein is not particularly limited. For example, Cas9 derived from *Streptococcus pyogenes* serotype M1 (Accession Number in the SwissProt database: Q99ZW2; the amino acid sequence of Cas9 is shown in SEQ ID NO: 30) may be used, or a polypeptide comprising the amino acid sequence of SEQ ID NO: 51 may be used. The Cas9 protein may be modified. Examples of modified Cas9 proteins include a polypeptide comprising an amino acid sequence in which one or a plurality of amino acid residues are substituted, inserted, and/or deleted in the amino acid sequence of SEQ ID NO: 30 or 51 and having nuclease activity as well as a polypeptide comprising an amino acid sequence having, 70% or higher, 80% or higher, for example, 90% or higher, 95% or higher, 97% or higher, 98% or higher, or 99% or higher identity with the amino acid sequence of SEQ ID NO: 30 or 51 and having nuclease activity.

Guide RNA (gRNA) comprises nucleotides complementary to the downstream sequence of the protospacer adjacent motif (PAM) sequence (NNG). The length of the guide nucleotide sequence is not particularly limited. For example, it comprises 15 to 30 nucleotides, 18 to 24 nucleotides, and preferably 19 to 22 nucleotides. A person skilled in the art can easily design the guide nucleotide sequence based on the target nucleotide sequence. The Cas9 protein binds to target DNA to which gRNA has bound, and it cleaves DNA. In order to enhance sequence specificity, either of the two independent nuclease domains within Cas9 (each domain has homology to HNH and RuvC endonucleases, respectively) may be mutated to convert Cas9 protein into nickase (Cong L. et al., Science, 2013, 339, pp. 819-823). In this case, two guide RNAs cleaves strands different from each other of the target DNA are needed to cleave the target DNA sequence. When the protein of interest to be introduced into the target plant cell is Cas9, in the present invention, it is preferable the complex of the present invention further comprise gRNA to deliver Cas9 and gRNA simultaneously. gRNA can bind to the complex through, for example, ionic interactions with a carrier peptide.

The term "zinc finger nuclease (ZFN)" used herein refers to a chimeric protein comprising at least 1 zinc finger DNA-binding domain and a DNA cleavage domain operably linked to the binding domain. The DNA cleavage domain is preferably linked to the C terminal side of the zinc finger DNA-binding domain. A zinc finger DNA-binding domain generally recognizes 3 nucleotides, ZFN recognizes 9 to 18 nucleotides, since it typically contains 3 to 6 zinc finger DNA-binding domains. A zinc finger domain may comprise, for example, the $Cis_2His_2$-type zinc finger represented by a zinc finger transcription factor, TFIIIA or Spl. DNA recognition specificity and/or binding specificity of ZFN can be modified to cause genetic recombination at any site. Such modification can be performed via known molecular biological techniques and/or chemical synthesis techniques (see, for example, M. Bibikova et al., Genetics, 2002, 161, pp. 1169-1175). A DNA cleavage domain is derived from a non-specific DNA cleavage domain (e.g., a DNA cleavage domain of a type II restriction enzyme such as FokI). As described above, FokI is activated by forming a dimer. Therefore, DNA can be specifically cleaved by using 2 zinc finger DNA-binding domain-FokI fusion proteins binding to different strands of the target DNA sequence.

In the present invention, the molecular weight of the protein of interest is not particularly limited. For example, the molecular weight may be 5 kDa or more, 10 kDa or more, or 15 kDa or more, and preferably 20 kDa or more, 25 kDa or more, 30 kDa or more, 40 kDa or more, or 50 kDa or more, and 300 kDa or less, 250 kDa or less, or 200 kDa or less, and preferably 190 kDa less, 180 kDa less, 170 kDa or less, or 160 kDa or less.

The charge of the protein of interest is not particularly limited, provided that the protein can form a complex with the carrier peptide described below through ionic interactions. When the carrier peptide is positively charged, it is preferable that the protein of interest be negatively charged. When the carrier peptide is negatively charged, it is preferable that the protein of interest be positively charged. In order to facilitate ionic interactions with the carrier peptide, the protein of interest may be modified by a technique known to a person skilled in the art. For example, a peptide comprising an amino acid charged oppositely from the carrier peptide may be added to the protein of interest, to enhance the ionic interactions between the carrier peptide and the protein of interest.

2. Target Plant Cell

In the present invention, types of target plant cells are not particularly limited. The present invention can be applied to any plant cells, such as angiosperms including monocotyledonous plants and dicotyledonous plants, gymnosperms, bryophytes, pteridophytes, herbaceous plants, and woody plants. Specific examples of the plants include solanaceae [eggplant (*Solanum melongena* L.), tomato (*Solanum lycopersicum*), green pepper (*Capsicum annuum* L. var. *angulosum* Mill.), red pepper (*Capsicum annuum* L.), tabacco (*Nicotiana tabacum* L.), etc.], gramineous [rice (*Oryza sativa*), wheat (*Triticum aestivum* L.), barley (*Hordeum vulgare* L.), perennial ryegrass (*Lolium perenne* L.), Italian ryegrass (*Lolium multiflorum* Lam.), meadow fescue (*Festuca pratensis* Huds.), thor fescue (*Festuca arundinacea* Schreb.), orchardgrass (*Dactylis glomerata* L.), timothy (*Phleum pratense* L.), etc.], brassicaceae [thale cres (*Arabidopsis thaliana*), colza (*Brassica campestris* L.), cabbage (*Brassica oleracea* L. var. *capitata* L.), Japanese radish (*Raphanus sativus* L.), rape (*Brassica campestris* L., *B. napus* L.), etc.], leguminous [soy bean (*Glycine max*), adzuki bean (*Vigna angularis* Willd.), kidney bean (*Phaseolus vulgaris* L.), broad beans (*Vicia faba* L.), etc.], cucurbitaceae [cucumber (*Cucumis sativus* L.), melon (*Cucumis melo* L.), watermelon (*Citrullus* vulgaris Schrad.), pumpkin (*C. moschata* Duch., *C. maxima* Duch.) etc.], convolvulaceae [sweet potato (*Ipomoea batatas*), etc.], liliaceae [leek (*Allium fistulosum* L.), onion (*Allium cepa* L.), Chinese chive (*Allium tuberosum* Rottl.), garlic (*Allium sativum* L.), Asparagus (*Asparagus officinalis* L.), etc.], lamiaceae [*Perilla* (*Perilla frutescens* Britt. var. *crispa*), etc.], asteraceae [chrysanthemum (*Chrysanthemum morifolium*), garland chrysanthemum (*Chrysanthemum coronarium* L.), lettuce (*Lactuca sativa* L. var. *capitata* L.), Chinese cabbage (*Brassica pekinensis* Rupr.), etc.], rosaceae [*Rose* (*Rose hybrida* Hort.), strawberry (*Fragaria×ananassa* Duch.), etc.], rutaceae [mandarin orange (*Citrus unshiu*), Japanese pepper (*Zanthoxylum piperitum* DC.), etc.], myrtaceae [*Eucalyptus* (*Eucalyptus globulus* Labill), etc.], salicaceae [poplar (*Populas nigra* L. var. *italica* Koehne), etc.], chenopodiaceae [spinach (*Spinacia oleracea* L.), sugar beet (*Beta vulgaris* L.), etc.], gentianaceae [gentian (*Gentiana scabra* Bunge var. *buergeri* Maxim.), etc.], and caryophyllaceae [carnation (*Dianthus caryophyllus* L.), etc.]. Among them, plants of Gramineae, Brassicaceae, Solanaceae, Leguminosae, and Salicaceae, in particular, plants of Brassicaceae such as *Arabidopsis thaliana*, plants of Solanaceae such as tomato, and plants of Salicaceae such as poplar, are preferably used.

Plant cells derived from any tissue can be used and are not particularly limited. For example, plant cells derived from an embryo, a callus, a pollen, a leaf, an anther, a root, an apex of root, a flower, a seed, a sheath, a stem and a cultured tissue can be used.

3. Carrier Peptide

In the present invention, a carrier peptide is a peptide which can form a carrier peptide/protein complex through ionic interactions with a protein (hereafter, it is also simply referred to as a "complex") and serve as a carrier mediating introduction of a protein into a plant cell. The carrier peptide of the present invention is characterized in comprising a cell-penetrating sequence and a polycationic or polyanionic sequence. The carrier peptide forms a complex with a protein through ionic interactions as described above. Therefore, when the protein of interest is negatively charged, the carrier peptide comprises a polycationic sequence, while when the protein of interest is positively charged, the carrier peptide comprises a polyanionic sequence. In the present invention, the carrier peptide may comprise a sugar chain, a lipid, and/or a phosphate residue.

The term "cell-penetrating sequence" refers to a sequence of a cell-penetrating peptide (CPP). The term "cell-penetrating peptide" refers to a peptide that is capable of penetrating the cell membrane and invading into the cell. Examples of cell-penetrating peptides include, but are not limited to, BP100 (Appl. Environ. Microbiol., 72 (5), 3302, 2006), HIV Tat (Journal of Biological Chemistry, 272, pp. 16010-16017, 1997), Tat$_2$ (Biochim. Biophys. Acta., 1768 (3), 419, 2007), Penetratin, pVEC, and pAntp (Journal of Biological Chemistry, 269, pp. 10444-10450, 1994), HSV-1 VP22 (Cell, 88, pp. 223-233, 1997), model amphiphilic peptide (MAP) (Biochimica Biophysica Acta, 1414, pp. 127-139, 1998), Transportan (FEBS Journal, 12, pp. 67-77, 1998), R7 (Nature Medicine, 6, pp. 1253-1257, 2000), MPG (Nucleic Acid Research 25, pp. 2730-2736, 1997), and Pep-1 (Nature Biotechnology, 19, pp. 1173-1176, 2001).

Specific examples of the cell-penetrating sequence include the following sequences: KKLFKKILKYL (SEQ ID NO: 1), RKKRRQRRRRKKRRQRRR (SEQ ID NO: 2), RKKRRQRRR (SEQ ID NO: 3), PLSSIFSRIGDP (SEQ ID NO: 4), PISSIFSRTGDP (SEQ ID NO: 5), AISSILSKTGDP (SEQ ID NO: 6), PILSIFSKIGDL (SEQ ID NO: 7), PLSSIFSKIGDP (SEQ ID NO: 8), PLSSIFSHIGDP (SEQ ID NO: 9), PLSSIFSSIGDP (SEQ ID NO: 10), RQIKIWFQNRRMKWKK (SEQ ID NO: 11), DAATATR-GRSAASRPTERPRAPARSASRPRRPVD (SEQ ID NO: 12), AAVALLPAVLLALLAP (SEQ ID NO: 13), AAVLLPVLLAAP (SEQ ID NO: 14), VTVLALGA-LAGVGVG (SEQ ID NO: 15), GALFLGWL-GAAGSTMGA (SEQ ID NO: 16), MGLGLHLLV-LAAALQGA (SEQ ID NO: 17), LGTYTQDFNKFHTFPQTAIGVGAP (SEQ ID NO: 18), GWTLNSAGYLLKINLKALAALAKKIL (SEQ ID NO: 19), and KLALKLALKALKAALKLA (SEQ ID NO: 20). Peptide sequences in which one or a plurality of amino acid residues are substituted, inserted, and/or deleted in these sequences and having a cell penetrating capacity may be preferably used. Examples of cell-penetrating sequences that can be used herein other than those described above are shown in Table 1 below.

TABLE 1

Examples of cell-penetrating sequences

| Sequence name | Amino acid sequence | SEQ ID NO: | Reference |
|---|---|---|---|
| 2BP100 | KKLFKKILKYLKKLFKKILKYL | 63 | (Ng et al., 2016) |
| Rev(34-50) | TRQARRNRRRRWRERQR | 64 | (Futaki et al., 2001) |

TABLE 1-continued

Examples of cell-penetrating sequences

| Sequence name | Amino acid sequence | SEQ ID NO: | Reference |
| --- | --- | --- | --- |
| R9 | RRRRRRRRR | 65 | (Duchardt et al., 2007) |
| D-R9 | rrrrrrrrr (r: D-form Arg) | 66 | (Wender et al., 2000) |
| R12 | RRRRRRRRRRRR | 67 | |
| KH9 | KHKHKHKHKHKHKHKHKH | 22 | (Chen et al., 2000) |
| K9 | KKKKKKKKK | 68 | |
| K18 | KKKKKKKKKKKKKKKKKK | 69 | |
| Pen2W2F | RQIKIFFQNRRMKFKK | 70 | (Thorén et al., 2004) |
| DPV3 | RKKRRRESRKKRRRES | 71 | (De Coupade et al., 2005) |
| 6-Oct | GRKRKKRT | 72 | (Ragin et al., 2002) |
| R9-TAT | GRRRRRRRRRPPQ | 73 | (Futaki et al., 2001) |
| Retro-Tat(57-49) | RRRQRRKKR | 74 | (Wender et al., 2000) |
| Sc18 | GLRKRLRKFRNKIKEK | 75 | (Neundorf et al., 2009) |
| KLA10 | KALKKLLAKWLAAAKALL | 76 | (Scheller et al., 1999) |
| IX | QLALQLALQALQAALQLA | 77 | (Scheller et al., 1999) |
| XI | LKTLATALTKLAKTLTTL | 78 | (Scheller et al., 1999) |
| No.14-12 | RAWMRWYSPTTRRYG | 79 | (Kamide et al., 2010) |
| pVEC | LLIILRRRIRKQAHAHSK | 80 | (Elmquist et al., 2001) |
| PenArg | RQIRIWFQNRRMRWRR | 81 | (Thorén et al., 2004) |
| M918 | MVTVLFRRLRIRRACGPPRVRV | 82 | (El-Andaloussi et al., 2006) |
| PolyP 3 (SAP) | VRLPPPVRLPPPVRLPPP | 83 | (Fernández-Carneado et al., 2004) |
| dhvar5 | LLLFLLKKRKKRKY | 84 | (Costa et al., 2015) |
| HPV33L2-445/467 | SYFILRRRRKRFPYFFTDVRVAA | 85 | (Kamper et al., 2006) |
| buforin II (5-21) | RAGLQFPVGRVHRLLRK | 86 | (Park et al., 1998) |
| scrambled pVEC | IAARIKLRSRQHIKLRHL | 87 | (Chugh and Eudes, 2008) |
| HPV33L2-DD447 | SYDDLRRRKRFPYFFTDVRVAA | 88 | |
| LAH4 | KKALLALALHHLAHLALHLALALKKA | 89 | (Mason et al., 2006) |
| ppTG1 | GLFKALLKLLKSLWKLLLKA | 90 | (Rittner et al., 2002) |
| Transportan (TP) | GWTLNSAGYLLGKINLKALAALAKKIL | 91 | (Soomets et al., 2000) |
| 2x ppTG1 | GLFKALLKLLKSLWKLLLKAGLFKALLKLLKSLWKLLLKA | 92 | (Numata and Kaplan, 2010) |
| pAntpHD(Pro50) | RQIKIWFPNRRMKWKK | 93 | (Derossi et al., 1994) |
| pAntp(44-58) | QIKIWFQNRRMKWKK | 94 | (Fischer et al., 1999) |
| Crot(27-39) | KMDCRWRWKCCKK | 95 | (Jha et al., 2011) |
| Crot(27-39) derevative (1) | MDCRWAWKCCKK | 96 | (Jha et al., 2011) |
| Crot(27-39) derevative (2) | KCGCRWRWKCGCKK | 97 | (Jha et al., 2011) |
| CyLoP-1 | CRWAWKCCKK | 98 | (Jha et al., 2011) |
| Inv3 | TKRRITPKDVIDVRSVTTEINT | 99 | (Chugh and Eudes, 2007) |

TABLE 1-continued

Examples of cell-penetrating sequences

| Sequence name | Amino acid sequence | SEQ ID NO: | Reference |
|---|---|---|---|
| Inv5 | AEKVDPVKLNLTLSAAAEALTGLGDK | 100 | (Lu et al., 2006) |
| Inv3.5 | TKRRITPKDVIDVRSVTTKINT | 101 | (Lu et al., 2006) |
| Inv3.10 | HHHHHHTKRRITPKDVIDVRSVTTEINT | 102 | (Lu et al., 2006) |
| ARF(1-22) | MVRRFLVTLRIRRACGPPRVRV | 103 | (Johansson et al., 2008) |
| Cyt C 71-101 | GTKMIFVGIKKKEERADLIAYLKKA | 104 | (Jones et al., 2016) |
| hLF peptide | KCFQWQRNMRKVRGPPVSCIKR | 105 | (Duchardt et al., 2007) |
| Glu-Oct-6 | EEEAAGRKRKKRT | 106 | (Lewis et al., 2010) |
| M 511 | FLGKKFKKYFLQLLK | 107 | |
| G53-4 | FLIFIRVICIVIAKLKANLMCKT | 108 | |
| M591 | YIVLRRRRKRVNTKRS | 109 | |
| E162 | KTVLLRKLLKLLVRKI | 110 | |
| E165 | LLKKRKVVRLIKFLLK | 111 | |
| M867 | KKICTRKPRFMSAWAQ | 112 | |
| MG2d | GIGKFLHSAKKWGKAFVGQIMNC | 113 | (Takeshima et al., 2003) |

References listed in Table 1 are as described below.

REFERENCES

Chen, Q R, Zhang, L, Stass, Sa and Mixson, a J (2000) Co-polymer of histidine and lysine markedly enhances transfection efficiency of liposomes. *Gene Ther* 7, 1698-1705.

Chugh, A and Eudes, F (2007) Translocation and nuclear accumulation of monomer and dimer of HIV-1 Tat basic domain in triticale mesophyll protoplasts. *Biochimica et Biophysica Acta—Biomembranes* 1768, 419-426.

Chugh, A and Eudes, F (2008) Cellular uptake of cell-penetrating peptides pVEC and transportan in plants. *J Pept Sci* 14, 477-481.

Costa, F M, Maia, S R, Gomes, P A and Martins, M C (2015) Dhvar5 antimicrobial peptide (AMP) chemoselective covalent immobilization results on higher antiadherence effect than simple physical adsorption. *Biomaterials* 52, 531-538.

De Coupade, C, Fittipaldi, A, Chagnas, V, Michel, M, Carlier, S, Tasciotti, E, Darmon, A, Ravel, D, Kearsey, J, Giacca, M, Cailler, F, Li, H, Qian, Z M, Ruben, S, Perkins, A, Purcell, R, Joung, K, Sia, R, Burghoff, R, Haseltine, W A, Rosen, C A, Tyagi, M, Rusnati, M, Presta, M, Giacca, M, Tasciotti, E, Zoppe, M, Giacca, M, Mie, M, Takahashi, F, Funabashi, H, Yanagida, Y, Aizawa, M, Kobatake, E, Silhol, M, Tyagi, M, Giacca, M, Lebleu, B, Vives, E, Vives, E, Brodin, P, Lebleu, B, Stein, S, Weiss, A, Adermann, K, Lazarovici, P, Hochman, J, Wellhoner, H, Torchilin, V P, Rammohan, R, Weissig, V, Levchenko, T S, Schwarze, S R, Ho, A, Vocero-Akbani, A, Dowdy, S F, Elliott, G, O'Hare, P, Derossi, D, Calvet, S, Trembleau, A, Brunissen, A, Chassaing, G, Prochiantz, A, Kokryakov, V N, Harwig, S S, Panyutich, E A, Shevchenko, A A, Aleshina, G M, Shamova, O V, Korneva, H A, Lehrer, R I, Jans, D A, Futaki, S, Goto, S, Sugiura, Y, Suzuki, T, Futaki, S, Niwa, M, Tanaka, S, Ueda, K, Sugiura, Y, Suzuki, T, Futaki, S, Niwa, M, Tanaka, S, Ueda, K, Sugiura, Y, Avrameas, E, Temynck, T, Temynck, T, Avrameas, A, Ragimbeau, J, Buttin, G, Avrameas, S, Avrameas, A, Temynck, T, Nato, F, Buttin, G, Avrameas, S, Avrameas, A, Temynck, T, Gasmi, L, Buttin, G, Fittipaldi, A, Ferrari, A, Zoppe, M, Arcangeli, C, Pellegrini, V, Beltram, F, Giacca, M, Richard, J P, Melikov, K, Vives, E, Ramos, C, Verbeure, B, Gait, M J, Chemomordik, L V, Lebleu, B, Morris, M C, Depollier, J, Mery, J, Heitz, F, Divita, G, Pichon, C, Monsigny, M, Roche, A C, Lundberg, M, Johansson, M, Lundberg, M, Wikström, S, Johansson, M, Walev, I, Hombach, M, Bobkiewicz, W, Fenske, D, Bhakdi, S, Husmann, M, Palmer, M, Lindgren, M, Hallbrink, M, Prochiantz, A, Langel, U, Pooga, M, Hallbrink, M, Zorko, M, Langel, U, Hallbrink, M, Floren, A, Elmquist, A, Pooga, M, Bartfai, T, Langel, U, Rostand, K S, Esko, J D, Henley, J R, Krueger, E W, Oswald, B J, McNiven, M A, Simons, K, Ikonen, E, Zhang, Z, Coomans, C, David, G, Lundberg, M, Johansson, M, Trehin, R, Merkle, H P, Eguchi, A, Akuta, T, Okuyama, H, Senda, T, Yokoi, H, Inokuchi, H, Fujita, S, Hayakawa, T, Takeda, K, Hasegawa, M, Vives, E, Drin, G, Cottin, S, Blanc, E, Rees, A R, Temsamani, J, Ziegler, A, Blatter, X L, Seelig, A, Seelig, J, Belting, M, Fuchs, S M, Raines, R T, Thoren, P E, Persson, D, Karlsson, M, Norden, B, Mazel, M, Clair, P, Rousselle, C, Vidal, P, Scherrmann, J M, Mathieu, D and Temsamani, J (2005) Novel human-derived cell-penetrating peptides for specific subcellular delivery of therapeutic biomolecules. *The Biochemical journal* 390, 407-418.

Derossi, D, Joliot, A H, Chassaing, G and Prochiantz, A (1994) The third helix of the Antennapedia homeodomain translocates through biological membranes. *J Biol Chem* 269, 10444-10450.

Duchardt, F, Fotin-Mleczek, M, Schwarz, H, Fischer, R and Brock, R (2007) A comprehensive model for the cellular uptake of cationic cell-penetrating peptides. *Traffic* 8, 848-866.

El-Andaloussi, S, Johansson, H J, Lundberg, P and Langel, U (2006) Induction of splice correction by cell-penetrating peptide nucleic acids. *J Gene Med* 8, 1262-1273.

Elmquist, A, Lindgren, M and Bartfai, T (2001) V E-Cadherin-Derived Cell-Penetrating Peptide, p VEC, with Carrier Functions. 244, 237-244.

Fernindez-Cameado, J, Kogan, M J, Pujals, S and Giralt, E (2004) Amphipathic Peptides and Drug Delivery. *Biopolymers—Peptide Science Section* 76, 196-203.

Fischer, D, Bieber, T, Li, Y, Elsasser, H P and Kissel, T (1999) A novel non-viral vector for DNA delivery based on low molecular weight, branched polyethylenimine: effect of molecular weight on transfection efficiency and cytotoxicity. *Pharmaceutical Research* 16, 1273-1279.

Futaki, S, Suzuki, T, Ohashi, W, Yagami, T, Tanaka, S, Ueda, K and Sugiura, Y (2001) Arginine-rich peptides. An abundant source of membrane-permeable peptides having potential as carriers for intracellular protein delivery. *J Biol Chem* 276, 5836-5840.

Jha, D, Mishm, R, Gottschalk, S, Wiesmiller, K H, Ugurbil, K, Maier, M E and Engelmann, J (2011) CyLoP-1: A novel cysteine-rich cell-penetrating peptide for cytosolic delivery of cargoes. *Bioconjug Chem* 22, 319-328.

Johansson, H J, El-Andaloussi, S, Holm, T, Mae, M, Janes, J, Maimets, T and Langel, U (2008) Characterization of a novel cytotoxic cell-penetrating peptide derived from p14ARF protein. *Molecular therapy: the journal of the American Society of Gene Therapy* 16, 115-123.

Jones, S, Uusna, J, Langel, U and Howl, J (2016) Intracellular Target-Specific Accretion of Cell Penetrating Peptides and Bioportides: Ultrastructural and Biological Correlates. *Bioconug Chem* 27, 121-129.

Kamide, K, Nakakubo, H, Uno, S and Fukamizu, A (2010) Isolation of novel cell-penetrating peptides from a random peptide library using in vitro virus and their modifications. *International Journal of Molecular Medicine* 25, 41-51.

Kamper, N, Day, P M, Nowak, T, Selinka, H C, Florin, L, Bolscher, J, Hilbig, L, Schiller, J T and Sapp, M (2006) A membrane-destabilizing peptide in capsid protein L2 is required for egress of papillomavirus genomes from endosomes. *J Virol* 80, 759-768.

Lewis, H D, Husain, A, Donnelly, R J, Barlos, D, Riaz, S, Ginjupalli, K, Shodeinde, A and Barton, B E (2010) Creation of a novel peptide with enhanced nuclear localization in prostate and pancreatic cancer cell lines. *BMC biotechnology* 10, 79.

Lu, S, Tager, L A, Chitale, S and Riley, L W (2006) A cell-penetrating peptide derived from mammalian cell uptake protein of *Mycobacterium tuberculosis*. *Analytical biochemistry* 353, 7-14.

Mason, A J, Martinez, A, Glaubitz, C, Danos, O, Kichler, A and Bechinger, B (2006) The antibiotic and DNA-transfecting peptide LAH4 selectively associates with, and disorders, anionic lipids in mixed membranes. *Faseb J* 20, 320-322.

Neundorf, I, Rennert, R, Hoyer, J, Schramm, F, Lobner, K, Kitanovic, I and Wolfi, S (2009) Fusion of a Short HA2-Derived Peptide Sequence to Cell-Penetrating Peptides Improves Cytosolic Uptake, but Enhances Cytotoxic Activity. *Pharmaceuticals (Basel)* 2, 49-65.

Ng, K K, Motoda, Y, Watanabe, S, Sofiman Othman, A, Kigawa, T, Kodama, Y and Numata, K (2016) Intracellular Delivery of Proteins via Fusion Peptides in Intact Plants. *PLoS One* 11, e0154081.

Numata, K and Kaplan, D L (2010) Silk-Based Gene Carriers with Cell Membrane Destabilizing Peptides. *Biomacromolecules* 11, 3189-3195.

Park, C B, Kim, H S and Kim, S C (1998) Mechanism of action of the antimicrobial peptide buforin II: Buforin II kills microorganisms by penetrating the cell membrane and inhibiting cellular functions. *Biochemical and biophysical research communications* 244, 253-257.

Ragin, A D, Morgan, R A and Chmielewski, J (2002) Cellular import mediated by nuclear localization signal peptide sequences. *Chem Biol* 9, 943-948.

Rittner, K, Benavente, A, Bompard-Sorlet, A, Heitz, F, Divita, G, Brasseur, R and Jacobs, E (2002) New basic membrane-destabilizing peptides for plasmid-based gene delivery in vitro and in vivo. *Mol Ther* 5, 104-114.

Scheller, A, Oehlke, J, Wiesner, B, Dathe, M, Krause, E, Beyermann, M, Melzig, M and Bienert, M (1999) Structural requirements for cellular uptake of alpha-helical amphipathic peptides. *J Pept Sci* 5, 185-194.

Soomets, U, Lindgren, M, Gallet, X, Hallbrink, M, Elmquist, A, Balaspiri, L, Zorko, M, Pooga, M, Brasseur, R and Langel, U (2000) Deletion analogues of transportan. *Biochimica et BiophysicaActa (BBA)—Biomembranes* 1467, 165-176.

Takeshima, K, Chikushi, A, Lee, K K, Yonehara, S and Matsuzaki, K (2003) Translocation of analogues of the antimicrobial peptides magainin and buforin across human cell membranes. *J Biol Chem* 278, 1310-1315.

Thordn, PEG, Persson, D, Esbjorner, E K, Goksor, M, Lincoln, P and Norddn, B (2004) Membrane Binding and Translocation of Cell-Penetrating Peptides †. *Biochemistry* 43, 3471-3489.

Wender, P A, Mitchell, D J, Pattabiraman, K, Pelkey, E T, Steinman, L and Rothbard, J B (2000) The design, synthesis, and evaluation of molecules that enable or enhance cellular uptake: Peptoid molecular transporters. *Proceedings of the National Academy of Sciences* 97, 13003-13008.

In one embodiment, the cell-penetrating sequence comprises an amino acid sequence selected from the group consisting of the amino acid sequences of SEQ ID NOs: 1 to 20, 22, and 63 to 113, or a sequence in which one or a plurality of amino acid residues are substituted, inserted, and/or deleted in these amino acid sequences and having a cell penetrating ability.

In one embodiment, the cell-penetrating sequence may comprise the polycationic sequence described below, such as an amino acid sequence of any of SEQ ID NOs: 4 to 9. In this case, the carrier peptide of the present invention further comprises the same or different polycationic or polyanionic sequence, in addition to the polycationic sequence serving as the cell-penetrating sequence.

Two or more types of cell-penetrating peptides may be used in combination. It is also preferable to select a cell-penetrating peptide specific to a cell of interest.

The term "polycationic sequence" used herein refers to a peptide sequence comprising at least three amino acid residues selected from lysine (K), arginine (R), and histidine (H) and stably binding to a negatively charged protein through ionic interactions under physiological conditions. A polycationic component may comprise a neutral amino acid in addition to positively charged amino acid residues (cationic amino acid residue) such as lysine, arginine, and histidine, as long as it sufficiently maintains the cationic property as a whole and stably binds to a protein under physiological conditions. This can be examined by a simple experiment by adding a protein. For example, this can be examined by mixing a carrier peptide with a protein of interest, and measuring zeta potentials and/or diameters of the particles in the mixture. For example, whether or not a carrier peptide-protein complex is formed can be examined by determining whether or not the zeta potential shifts from a negative level to a positive level when adding the carrier peptide to the negatively charged protein of interest.

The polycationic sequence of the carrier peptide comprises at least three lysine, arginine, or histidine residues, and the upper limit of the number thereof is not limited. The polycationic sequence can comprise up to 450 amino acid residues, and it is known to still remain functional (Proc. Natl. Acad. Sci., U.S.A., 1990, 87, 3410-3414). However, the length of the polycationic sequence is preferably 5 to 100, more preferably 5 to 50, and further preferably 7 to 20 amino acid residues. The ratio of cationic amino acid residues in the polycationic sequence is preferably 40 mol % or more, more preferably 60 mol % or more, further preferably 80 mol % or more, and the most preferably 90 mol % or more. Polycationic sequence exclusively consisting of polycationic amino acid residues is most preferably used.

The polycationic sequence comprises preferably 4 or more, more preferably 5 or more, and further preferably 7 or more, and preferably 30 or less, more preferably 25 or less, and further preferably 20 or less lysine, arginine, and/or histidine residues. Further, the polycationic sequence comprises preferably 3 or more, more preferably 5 or more, and particularly preferably 7 or more contiguous lysine, arginine, and/or histidine residues. When the ratio of arginine in the cationic amino acid residues is high, introduction into a cell tends to be fast, whereas when the ratio of histidine and lysine is high, introduction into a cell tends to be slow. Therefore, the introduction rate of a complex into a cell can be controlled by appropriately selecting a polycationic sequence depending on the intended use of the complex of the present invention, such as organelle-specific introduction as described below. For example, a polycationic sequence preferably comprises KH repeats, such as 3 to 20 KH repeats, more preferably 5 to 15 KH repeats, and further preferably 7 to 12 KH repeats. Examples of polycationic sequences include: contiguous arginine (R) residues, such as 3 to 20 contiguous Rs, preferably 5 to 15 contiguous Rs, and further preferably 7 to 12 contiguous Rs; contiguous lysine (K) residues, such as 3 to 20 contiguous Ks, preferably 5 to 15 contiguous Ks, and further preferably 7 to 12 contiguous Ks; and contiguous histidine (H) residues, such as 3 to 20 contiguous Hs, preferably 5 to 15 contiguous Hs, and further preferably 7 to 12 contiguous Hs. Specific examples of the polycationic sequence include the following sequences: KKKKKKKK (SEQ ID NO: 21) and KHKHKHKHKHKHKHKH (SEQ ID NO: 22).

The term "polyanionic sequence" used herein refers to a peptide sequence comprising at least three amino acid residues selected from aspartic acid (D) and glutamic acid (E) and stably binding to a positively charged protein under physiological conditions. A polyanionic component can comprise a neutral amino acid, in addition to negatively charged amino acid residues (anionic amino acid residue) such as aspartic acid and glutamic acid, as long as it sufficiently maintains the anionic property as a whole and stably binds to a protein under physiological conditions. This can be examined by a simple experiment by adding a protein as with the case of the polycationic sequence. For example, this can be examined by mixing a carrier peptide with a protein of interest, and measuring zeta potentials and/or diameters of the particles in the mixture. For example, whether or not a carrier peptide-protein complex is formed can be examined by determining whether or not the zeta potential shifts from a negative level to a positive level when adding carrier peptide to the positively charged protein of interest.

The polyanionic sequence of the carrier peptide comprises at least three aspartic acid or glutamic acid residues, and the upper limit of the number thereof is not limited. The length of the polyanionic sequence is preferably 5 to 100, more preferably 5 to 50, and further preferably 7 to 20 amino acid residues. The ratio of anionic amino acid residues in the polyanionic sequence is preferably 40 mol % or more, more preferably 60 mol % or more, further preferably 80 mol % or more, and the most preferably 90 mol % or more. Polyanionic sequence consisting of polyanionic amino acid residues is most preferably used.

The polyanionic sequence comprises preferably 4 or more, more preferably 5 or more, and further preferably 7 or more, and preferably 30 or less, more preferably 25 or less, and further preferably 20 or less aspartic acid and/or glutamic acid residues. Further, the polyanionic sequence comprises preferably 3 or more, more preferably 5 or more, and particularly preferably 7 or more contiguous aspartic acid and/or glutamic acid residues. For example, the polyanionic sequence preferably comprises aspartic acid (D) repeats, such as 3 to 20 D repeats, more preferably 5 to 15 D repeats, and further preferably 7 to 12 D repeats. Further examples of polyanionic sequences include: contiguous arginine (R) residues, such as 3 to 20 contiguous Rs, preferably 5 to 15 contiguous Rs, and further preferably 7 to 12 contiguous Rs; and contiguous glutamic acid (E) residues, such as 3 to 20 contiguous Es, preferably 5 to 15 contiguous Es, and further preferably 7 to 12 contiguous Es.

The carrier peptide of the present invention corresponds to a linear fusion of a cell-penetrating sequence and a polycationic or polyanionic sequence. In the fusion, the polycationic or polyanionic sequence is preferably bound to the N-terminus and/or C-terminus of the cell-penetrating sequence. One or more, preferably one or several, more preferably about one to three polycationic or polyanionic sequences as described above can be linked to the cell-penetrating sequence. Particularly preferably one polycationic or polyanionic sequence can be linked to the cell-penetrating sequence. A peptide comprising a polycationic or polyanionic sequence linked to the cell-penetrating sequence can be synthesized in accordance with a general peptide synthesis technique, such as a solid phase method, or it can be prepared via bioengineering such as genetic recombination. Alternatively, the cell-penetrating sequence and the polycationic or polyanionic sequence prepared separately can be chemically linked via, for example, crosslinking. When linking the cell-penetrating sequence to the polycationic or polyanionic sequence, an oligo peptide linker may be interposed therebetween, if needed. For example, a linker consisting of one or several amino acids may be interposed, and the amino acid residues constituting the linker may be appropriately selected. Since a cell-penetrating peptide exerts its characteristics when positioned at the N-terminus, the cell-penetrating sequence is preferably linked to the N-terminus of the polycationic or polyanionic sequence. When the carrier peptide of the present invention is prepared by a recombinant DNA technique, for example, a DNA fragment encoding the polycationic or polyanionic sequence is linked to one or both ends of a DNA fragment encoding the cell-penetrating sequence by a linkage reaction with an appropriate DNA adaptor. Such gene manipulation method is known to a person skilled in the art of molecular biology.

The carrier peptide of the present invention can further comprise any sequence, such as an organelle transit sequence, in addition to a cell-penetrating sequence and a polycationic or polyanionic sequence. The organelle transit sequence refers to a peptide sequence having affinity for or permeability in a particular organelle within a cell. By adding the organelle transit sequence, a protein of interest can be delivered to any organelle within a plant cell. Examples of the organelle transit sequence include a nuclear localization signal (NLS) targeting a nucleus and peroxisomal targeting signal (PTS). A peptide sequence having affinity for or permeability in a mitochondrion or a chloroplast can also be used. More specific examples include, but are not limited to: a chloroplast transit sequence derived from *Chlamydomonas* ferredoxin (Cf) and *Chlamydomonas* Rubisco activase (CRa); a mitochondrial matrix targeting signal peptide (Biochemical and Biophysical Research Communications, 1996, 226, pp. 561-565); and mitochondrial inner membrane targeting signal peptides, such as SS01, SS02, SS31, and SS20 (the AAPS Journal, 2006, 8, pp. E277-E283), 50S ribosome protein L28, 50S ribosome protein L24, 50S ribosome protein L27, RuBisCo small chain, and LHCII type 1.

Specific examples of the organelle transit sequence include the following sequences: PKKKRKV (SEQ ID NO: 31), SKL (SEQ ID NO: 32), MAMAMRSTFAARVGAK-PAVRGARPASRMSCMA (SEQ ID NO: 33), MQVTMKS-SAVSGQRVGGARVATRSVRRAQLQV (SEQ ID NO: 34), MATMVAGISLRGPVMSSHRTFSVTKRASLPQSKLS-SELSFVTSQLSGLKISSTHFISSSA PLSVPFKPSLQPVA (SEQ ID NO: 35), MAALQSSFAGLSTSFFGQRFSP-PLSLPPLVKSTEGPCLIQA (SEQ ID NO: 36), MAVSFSLVGAFKGLSLASSSSFLKGDFGAAF-PVAPKFSVSFPLKSPLTIES (SEQ ID NO: 37), MASSVLSSAAVATRSN-VAQANMVAPFTGLKSAASFPVSRKQNLDITSIASNG-GRVQC (SEQ ID NO: 38), MAASTMALSSPAF-AGKAVKLSPAASEVLGSGRVTMRKTV (SEQ ID NO: 39), and MLSLRQSIRFFK (SEQ ID NO: 40). A peptide sequence in which one or a plurality of amino acid residues are substituted, inserted, and/or deleted in any of such peptide sequences by may be preferably used. Such sequence may be used alone or in combination of two or more, if appropriately.

Examples of the sequences of the carrier peptide of the present invention include an amino acid sequence comprising: KKLFKKILKYLKKLFKKILKYLKKKKKKKK (SEQ ID NO: 23; (BP100)$_2$K$_8$) or KKLFKKIL-KYLKHKHKHKHKHKHKHKH (SEQ ID NO: 24; BP100(KH)$_9$), preferably, an amino acid sequence comprises KKLFKKILKYLKKLFKKILKYLKKKKKKKK (SEQ ID NO: 23).

While the form of the carrier peptide/protein complex is not limited, it is generally in a particle form, the average hydrodynamic diameter thereof is preferably 100 nm or more, more preferably 150 nm or more, and further preferably 200 nm or more, and preferably 700 nm or less, more preferably 600 nm or less, and further preferably 550 nm or less. The average hydrodynamic diameter can be measured by a dynamic light scattering (DLS) method. The present inventors discovered that a protein can be introduced into a plant cell with high efficiency by using a complex having such an average hydrodynamic diameter.

The complex of the present invention may comprise other substances, in addition to the carrier peptide and the protein of interest. For example, when the protein of interest is Cas9, the complex preferably comprises guide RNA, so that Cas9 and the guide RNA can be delivered simultaneously.

<Method for Producing a Carrier Peptide/Protein Complex>

In one aspect, the present invention relates to a method for producing a carrier peptide/protein complex comprising a step of mixing a carrier peptide with a protein of interest to be introduced into a target plant cell to form a carrier peptide/protein complex.

The constitutions of the carrier peptide, the protein of interest, the carrier peptide/protein complex, and the target plant cell according to the present aspect are as described above and the description thereof is accordingly omitted herein.

In the step of mixing a carrier peptide with a protein of interest, a molar ratio of a carrier peptide to a protein of interest is preferably 1 or more, further preferably 2 or more, 3 or more, 4 or more, and most preferably 5 or more, and preferably 50 or less, further preferably 40 or less, 30 or less, 25 or less, 20 or less, or 15 or less, and most preferably 10 or less. In the step of mixing, accordingly, the molar ratio of the carrier peptide to the protein of interest is, for example, 1:1 to 50:1, 2:1 to 25:1, and preferably 3:1 to 20:1 or 5:1 to 10:1. The protein can be introduced into a plant cell with high efficiency, by mixing the carrier peptide with the protein within the molar ratio described above to form a complex.

The step of mixing a carrier peptide with a protein to form a complex can be performed by, for example, mixing the carrier peptide with the protein in the solution. In such a case, the concentration of the carrier peptide is generally 10 μg/mL to 10 mg/mL, and preferably 100 μg/mL to 1 mg/mL, and the concentration of the carrier peptide solution is generally 1 μg/mL to 10 mg/mL, and preferably 10 μg/mL to 1 mg/mL.

The conditions of the step of mixing a carrier peptide with a protein to form a complex are not particularly limited. For example, the step of mixing can be carried out by performing incubation at room temperature (25° C. to 35° C.) for several minutes to several hours, such as 5 minutes to 6 hours, 10 minutes to 3 hours, and preferably 20 minutes to 1 hour.

<Method for Introducing a Protein of Interest into a Target Plant Cell>

In one aspect, the present invention relates to a method for introducing a protein of interest into a target plant cell comprising: a step of mixing a carrier peptide with a protein of interest to be introduced into a target plant cell to form a carrier peptide/protein complex; and a step of bringing the resulting complex into contact with the target plant cell.

The constitutions of the carrier peptide, the protein of interest, the carrier peptide/protein complex, the target plant cell, and the step of mixing a carrier peptide with a protein of interest according to the present aspect are as described above and the description thereof is accordingly omitted herein.

The step of bringing the complex into contact with the target plant cell can be performed in accordance with a method known in the art without particular limitation. For example, the step can be performed by bringing a solution containing the carrier peptide/protein complex of the present invention into contact with a target plant cell, and then incubating them in an incubator at room temperature (20° C. to 35° C.) under a constant light for 8 to 18 hours every day. Incubation is performed preferably for 1 hour to 150 hours, more preferably for 3 hours to 50 hours, and further preferably for 5 hours to 30 hours. The method for introducing a protein according to the present invention is excellent, since it can introduce a protein within a relatively short period of time. The step of contact may be performed with cells such as cultured cells, or may be performed directly with, for example, plant tissues, such as an embryo, a callus, a pollen, a leaf, an anther, a root, an apex of root, a flower, a seed, a sheath, and a stem of a plant, and a cultured tissue.

The method may optionally comprise a step of facilitating introduction of a protein of interest into a target plant cell, prior to the step of bringing the complex into contact with the target plant cell. An example of such step is irradiating high-intensity light to a target plant cell. Light intensity may be, for example, 20 $\mu mol/m^2$ sec to 500 $\mu mol/m^2$ sec, 50 $\mu mol/m^2$ sec to 200 $\mu mol/m^2$ sec, and preferably 80 $\mu mol/m^2$ sec to 100 $\mu mol/m^2$ sec, and duration for irradiating light is, for example, 2 hours to 20 hours, 4 hours to 15 hours, and preferably 6 hours to 10 hours.

<Method for Modifying Plant Genome>

When the protein of interest is a genome-editing protein, such as TALEN, Cas9, or ZFN, the method for producing a protein according to the present invention can be employed as a method of genome editing. Specifically, in one embodiment, the present invention relates to a method for editing or modifying the genome of the target plant cell, or a method for producing a genome-modified plant cell, wherein the method comprises: a step of mixing a carrier peptide with a genome-editing protein to be introduced into a target plant cell to form the carrier peptide/protein complex of the present invention; and a step of bringing the resulting complex into contact with the target plant cell. The constitutions of the carrier peptide, the protein of interest, the carrier peptide/protein complex, the target plant cell, the step of mixing a carrier peptide with a protein of interest, and the step of bringing the resulting complex into contact with the target plant cell according to the present aspect are as described above and the description thereof is accordingly omitted herein.

This method does not suffer from problems such as unexpected incorporation of foreign DNA into the plant nuclear genome or organelle genome that destructs an endogenous gene, or incorporation of antibiotic-resistance into pathogenic bacteria in soil via horizontal gene transfer. Accordingly, this method is advantageous compared with the conventional method that may leave an influence of genome editing on the progeny.

A plant with transiently modified genome can be produced by directly applying this method to a plant. The term "transiently modified genome" used herein refers a modification such that the modified genome is not transferred to the progeny and effects of a genome modification are limited to the treated plants. Also, a plant with an inheritable genome modification can be obtained by applying this method to a plant cell and producing a plant from the plant cell. The term "an inheritable genome modification" used herein refers to a modification such that the modified genome is transmitted to the progeny, and effects of the genome modification are exerted on the progeny of the treated plant.

Accordingly, in one aspect, the present invention relates to a method for producing a genome-modified plant comprising a step of producing a genome-modified plant from the genome-modified plant cell obtained by the method described above. The step of producing a genome-modified plant from a genome-modified plant cell is known to a person skilled in the art. For example, a genome-modified plant can be obtained by applying the method of genome modification according to the present invention to a germ cell, such as an embryo or seed, and the allowing resulting cell to grow. Also, a genome-modified plant can be obtained by applying the method of genome modification according to the present invention to a plant tissue, such as a leaf, an anther, a root, an apex of root, a flower, or a seed, dedifferentiating the resultant to obtain a callus, and redifferentiating the callus. The steps of dedifferentiation and redifferentiation can be omitted depending on a plant type and a tissue type. The resulting genome-modified plant may be screened with an antibiotics or the like, according to need. According to the method of the present invention, a plant in which an arbitrary gene is modified can be obtained. Thus, the method of the present invention can be useful for improving a plant variety etc.

The present invention also relates to a genome-modified plant cell or a genome-modified plant obtained by the method described above. The genome-modified plant according to the present invention may be different from a genome-modified plant obtained by other methods in not comprising an incorporated foreign gene or the like other than the site targeted by the genome-editing protein.

When the genome-editing protein is Cas9, guide RNA is needed to be introduced in order to edit or modify genome. It is preferable that guide RNA be included in the complex of the present invention and delivered into the cell together with Cas9; however, guide RNA may be introduced into the cell via other means. An example thereof is transfection of guide RNA or a vector, such as a plasmid vector containing guide RNA.

<Agent for Introducing a Protein of Interest Consisting of a Carrier Peptide>

In one aspect, the present invention relates to an agent for introducing a protein of interest into a target plant cell, consisting of a carrier peptide containing a cell-penetrating sequence and a polycationic or polyanionic sequence. According to the present aspect, the carrier peptide forms a carrier peptide/protein complex with the protein of interest through ionic interactions. The constitutions of the carrier peptide, the protein of interest to be introduced into a target plant cell, the target plant cell, and the carrier peptide/protein complex according to the present aspect are as described above and the description thereof is accordingly omitted herein.

The present invention also relates to a composition used for introducing a protein of interest into a target plant, comprising the agent for introducing the protein of interest as described above. This composition may comprise, in addition to the agent for introduction, for example, a medium such as water or oil, a buffer, a salt, and/or other substances.

<Kit for Introducing a Protein of Interest into a Target Plant Cell>

In one aspect, the present invention relates to a kit for introducing a protein of interest into a target plant cell, comprising the protein of interest to be introduced into the target plant cell, and the carrier peptide.

The constitutions of the carrier peptide, the protein of interest to be introduced into the target plant cell, and the target plant cell according to the present aspect are as described above and the description thereof is accordingly omitted herein. The kit according to the present invention may comprise instructions, a reagent and an apparatus for forming a complex or cell introduction, and the like.

EXAMPLES

Example 1: Formation of Peptide/Protein Complexes at Various Molar Ratios and Characterization Thereof (Method)
Synthesis of Carrier Peptide (BP100)$_2$K$_8$ (KKLFKKILKYLKKLFKKIL-KYLKKKKKKKK (SEQ ID NO: 23), theoretical pI/Mw: 10.75/3851.13 Da) and BP100(KH)$_9$ (KKLFKKIL-KYLKHKHKHKHKHKHKHKHKH (SEQ ID NO: 24), theoretical pI/Mw: 10.81/3809.71 Da) were prepared by a standard technique of 9-fluorenylmethoxycarbonyl (Fmoc) solid-phase peptide synthesis, and purified via high-performance liquid chromatography (Fields G. B. and Noble R. L., Int. J. Pept. Protein Res., 1990, 35, pp. 161-214). The molecular weights of the peptides were determined by matrix-assisted laser desorption/ionization flight time mass analysis (MALDI-TOFMS).

Preparation of Protein Labeled with Rhodamine B Isothiocyanate

Saccharomyces cerevisiae-derived rhodamine B isothiocyanate (RhB) (Mw: 536.08 g/mol), BSA, and ADH were purchased from Sigma-Aldrich (St. Louis, Mo., U.S.A.) and used in the experiment described below.

At the outset, 10 mg of powdery BSA or ASH was dissolved in 1 mL of a sodium carbonate solution (0.1 M, pH 9.0) to prepare a 10.0 g/l BSA or ASH solution. Further, 1 mg of powdery RhB was dissolved in 100 μl of dimethyl sulfoxide to prepare a 10.0 g/l RhB solution. Subsequently, the RhB solution was added dropwise to and mixed with the protein solution with mild stirring, and the resulting solution was incubated with continuous stirring overnight at 4° C., so as to allow Rhb to conjugate to the protein. Free RhB was removed from the BSA-RHB conjugate or the ADH-RhB conjugate via gel filtration chromatography at 25° C. using the Sephadex G-25 column (Sigma-Aldrich, St. Louis, Mo., U.S.A.). The concentration of the purified BSA-RhB conjugate or ADH-RhB conjugate was measured with the UV-vis spectrometer at the absorbance of 280 nm and 555 nm. An extent of labeling was calculated using the following formula: (OD$_{555}$ of RhB (nm)×protein Mw)/(protein concentration (g/l)×molar absorption coefficient of RhB). The molar absorption coefficient of RhB is 106,000 M$^{-1}$ cm$^1$. In this example, 4 RhB molecules were conjugated to a BSA molecule, and 6 RhB molecules were conjugated to an ADH molecule.

Preparation of Carrier Peptide/Protein Complexes at Various Peptide/Protein Molar Ratios and Characterization Thereof A solution of 1.0 g/l of the peptide ((BP100)$_2$K or BP100(KH)$_9$) was mixed with 2 μg of the protein (the BSA-RhB conjugate) at various peptide/protein molar ratios (1, 5, 10, and 25) at 25° C. for about 5 minutes to prepare carrier peptide/protein complexes, and the resultants were diluted to the final volume of 100 μl with autoclaved ultrapure water (MilliQ water). Thereafter, 10 1 of the solution was taken and further diluted to the final volume of 100 μl. The average hydrodynamic diameter of the complexes was measured via dynamic light scattering (DLS) using Zetasizer Nano-ZS (Malvern Instruments, Ltd., Worcestershire, U.K.). Polydispersion indexes (PDI) were determined with the zeta nanosizer (Zetasizer software ver 6.20) using He—Ne laser (633 nm) at 25° C. and a backscattering detection angle of 173°. Thereafter, the sample was further diluted to the total volume of 750 μl with autoclaved ultrapure water (MilliQ water), and the zeta potential was analyzed via laser Doppler microelectrophoresis using Zetasizer Nano-ZS. The zeta potential and zeta shift of the samples were measured three times and the average was determined with Zetasizer software ver 6.20.

In order to perform a configurational characterization via atomic force microscopy, 10 μl of carrier peptide/protein complex solutions (1.0 mg/l) prepared at various peptide/protein molar ratios were added dropwise on cut mica and adsorbed to the mice substrate for 30 seconds (Mori O. and Imae T., 1996, Colloid Surface B 9, 31-36). Thereafter, the samples were thoroughly washed with autoclaved ultrapure water (MilliQ water) to remove all the buffer components. After removing remaining water from the mica surface, the mica was air-dried at room temperature overnight. The samples were observed via AFM using a silicon cantilever in air at room temperature in a tapping mode at a spring constant of 1.3 N/m (AFM5300E, Hitachi High-Tech Science Corporation, Japan).

(Results)

BP100(KH)$_9$ and (BP100)$_2$K$_8$ were each mixed with BSA-RhB at various peptide/protein molar ratios (the molar concentration of the protein was maintained at a constant level and that of the peptide was elevated from 1 to 25) to form the carrier peptide/protein complexes (i.e., BP100(KH)$_9$/BSA-RhB and (BP100)$_2$K/BSA-RhB).

The results of measurements of hydrodynamic diameters, PDI, and zeta potentials of the carrier peptide/protein complex are shown in Tables 2 and 3 below.

TABLE 2

Characterization of (BP100)$_2$K$_8$/BSA-RhB complex at various peptide/protein molar ratios

| Molar ratio | Hydrodynamic diameter (nm) | PDI | Zeta potential (mV) |
|---|---|---|---|
| 1.0 | 341 ± 73 | 0.44 ± 0.05 | −29.0 ± 0.2 |
| 5.0 | 296 ± 2 | 0.40 ± 0.08 | 18.9 ± 0.3 |
| 10.0 | 226 ± 1 | 0.15 ± 0.03 | 18.8 ± 0.3 |
| 25.0 | 173 ± 8 | 0.20 ± 0.01 | 23.4 ± 0.3 |

TABLE 3

Characterization of BP100(KH)$_9$/BSA-RhB complex at various peptide/protein molar ratios

| Molar ratio | Hydrodynamic diameter (nm) | PDI | Zeta potential (mV) |
|---|---|---|---|
| 1.0 | 329 ± 12 | 0.26 ± 0.04 | −27.8 ± 0.4 |
| 5.0 | 452 ± 44 | 0.44 ± 0.02 | 10.4 ± 0.4 |
| 10.0 | 547 ± 32 | 0.49 ± 0.09 | 13.7 ± 0.2 |
| 25.0 | 586 ± 82 | 0.51 ± 0.11 | 15.8 ± 0.4 |

The hydrodynamic diameter of BSA-RhB not forming the complex was 92±2 nm. The average hydrodynamic diameter of (BP100)$_2$K/BSA-RhB was 341±73 nm at the peptide/protein molar ratio of 1.0. As the peptide/protein molar ratio increased, the average hydrodynamic diameter decreased from 341±73 nm to 173±8 nm (Table 1).

In contrast, the average hydrodynamic diameter of the BP100(KH)$_9$/BSA-RhB complex increased from 329±12 nm to 586±82 nm as the peptide/protein molar ratio increased (Table 2).

BSA-RhB had a negative surface charge of −35.3±1.5 mV. As the peptide/protein molar ratio increased, the zeta potentials of both the (BP100)$_2$Ks/BSA-RhB complex and the BP100(KH)$_9$/BSA-RhB complex increased from a negative level to a positive level (Tables 1 and 2). That is, the BSA-RhB surface was covered by a cationic fusion protein, an ionic complex was then formed, and the zeta potential increased.

Figure 1:
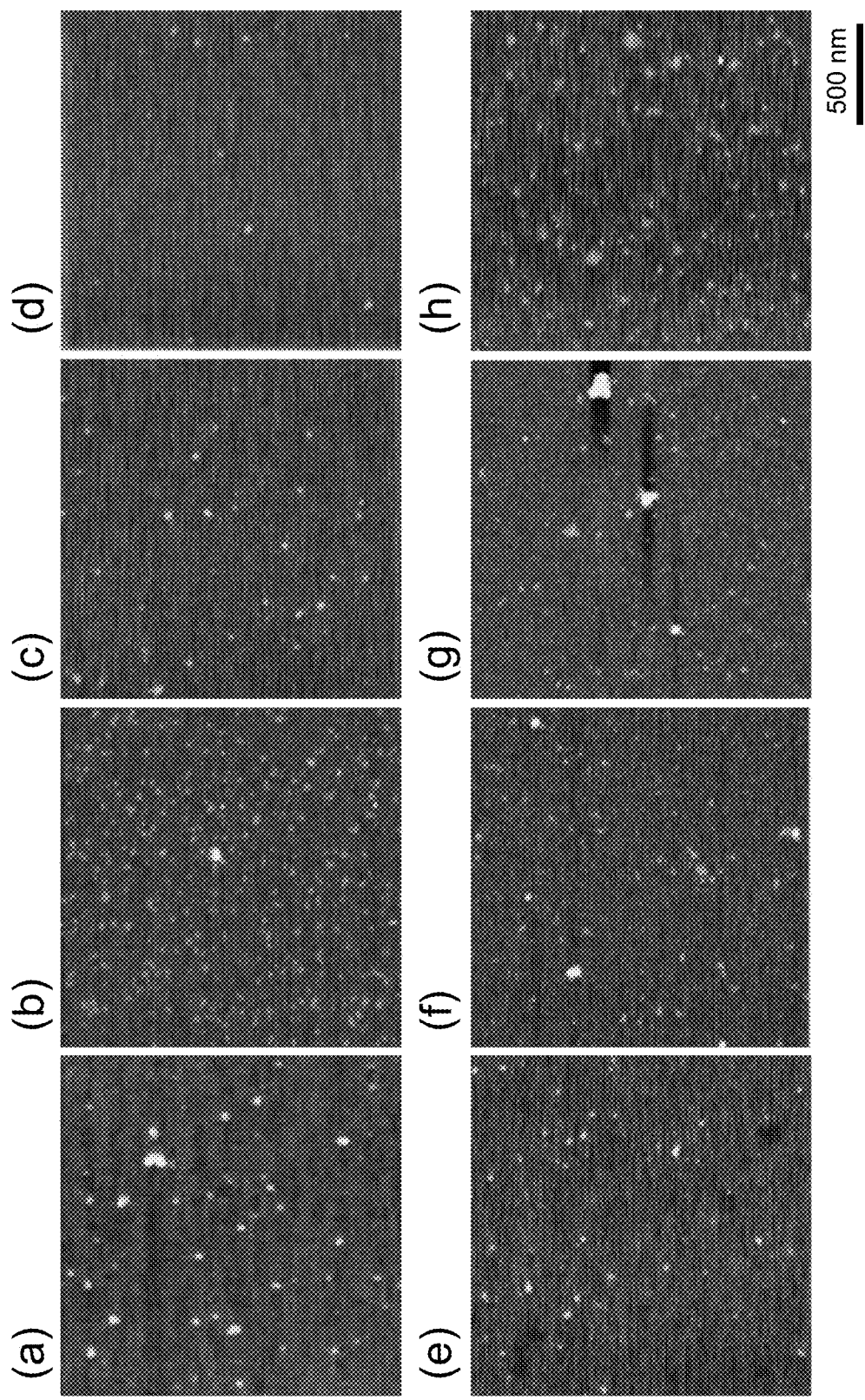
FIG. 1 shows the results of observation of the carrier peptide/BSA-RhB complex under anatomic force microscope (AFM). The carrier peptide shown is $(BP100)_2K_8$ (a) to (d), and $BP100(KH)_9$ in (e) to (h). A molar ratio of the carrier peptide to BSA-RhB is 1:1 in (a), 5:1 in (b), 10:1 in (c), 25:1 in (d), 1:1 in (e), 5:1 in (f), 10:1 in (g), and 25:1 in (h).
Figure 2:
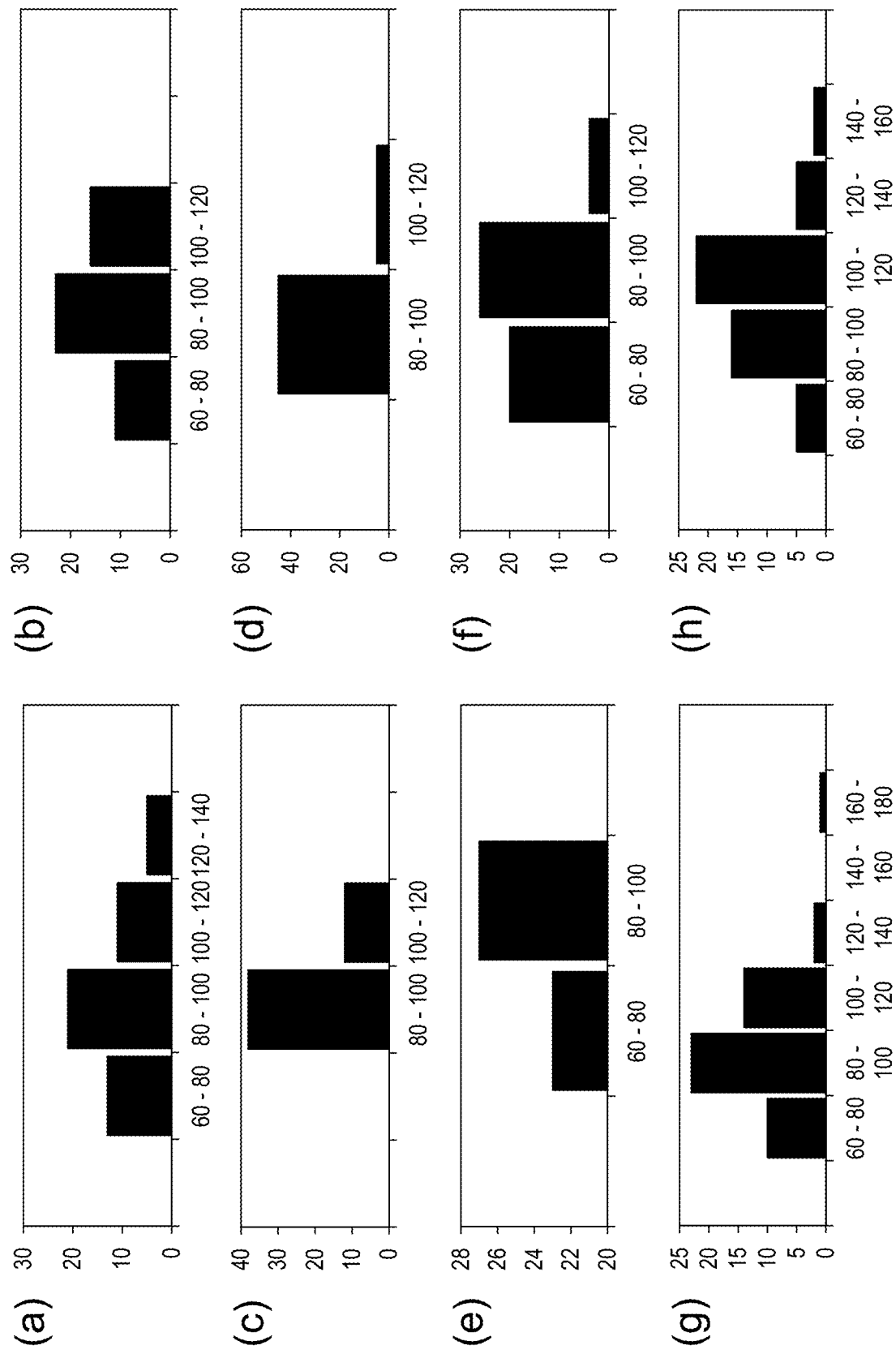
FIG. 2 shows the results of measurement of the particle size of the peptide-BSA-RhB complex under AFM. (a) to (h) correspond to (a) to (h) of FIG. 1 (provided that n=50). The horizontal axis shows the particle diameter (nm) and the vertical axis shows the number of particles.

As a result of measurement by AFM, the $(BP100)_2K_8$/BSA-RhB complex at a molar ratio of 5 or 10 and the $BP100(KH)_9$/BSA-RhB complex at a molar ratio of 1 were found to have homogenous spherical form (FIGS. 1 and 2).

Example 2: Introduction of BSA-RhB and ADH-RhB into Cells (Method)
Preparation of YFP-Introduced Plants A transgenic *Arabidopsis thaliana* plant expressing a yellow fluorescent protein (YFP) was prepared via *Agrobacterium tumefaciens* (GV3101 (pMP90) strain)-mediated transformation of a binary vector comprising the cauliflower mosaic virus 35S promoter and the In—YFP gene into a wild-type *Arabidopsis thaliana* (Columbia) plant (Ohtani M. et al., Plant Cell, 2013, 25, pp. 2056-2069). Seeds of both the wild-type *Arabidopsis thaliana* strain and the transgenic *Arabidopsis thaliana* strain were sowed in a pot containing a plant medium comprising soil (Pro-Mix; Premier Tech Ltd, Quebec, Canada) and vermiculite (Vs kakou, Tokyo, Japan) at 2:1.

Introduction of the Carrier Peptide/Protein Complex into Leaf

About 100 µl of the solution of the carrier peptide/protein complex (the $(BP100)_2K$/BSA-RhB or $BP100(KH)_9$/BSA-RhB complex) prepared in Example 1 was brought into direct contact with an YFP-expressing *Arabidopsis thaliana* leaf at various peptide/protein molar ratios (1, 5, 10, and 25) with a needleless syringe. Also, about 100 l of the solution of the carrier peptide/protein complex (the $(BP100)_2Ks$/ADH-RhB complex) prepared in Example 1 was brought into direct contact with an YFP-expressing *Arabidopsis thaliana* leaf at the peptide/protein molar ratio of 10.

Incorporation of the Carrier Peptide/Protein Complex into Cells

Incorporation of proteins into cells was quantitatively assayed using a confocal laser scanning microscope (CLSM, Carl Zeiss, Oberkochen, Germany). Intracellular delivery of the peptide/BSA-RhB complex or the peptide/ADH-RhB complex to an YFP-expressing *Arabidopsis thaliana* leaf was observed by detecting the YFP fluorescence at the excitation light of 488 nm and detecting the RhB fluorescence at the excitation light of 555 nm.

Quantification of Peptide Delivery Efficiency

A transgenic YFP-expressing *Arabidopsis thaliana* leaf was collected 6 hours after bringing it into contact with the $(BP100)_2K_8$/BSA-RhB or $BP100(KH)_9$/BSA-RhB complex, and the leaf was washed 2 times with PBS (D-PBS(−), Wako Pure Chemical Industries Ltd., Osaka, Japan) to remove excess BSA-RhB on the leaf surface. Total crude protein extracted from the contacted leaf with 1× lysis buffer (Promega, Madison, U.S.A.) was subjected to 4 to 15% tris-glycine-sodium dodecyl sulfate (SDS)-polyacrylamide gel electrophoresis (PAGE) (Bio-rad, California, U.S.A.) at a constant voltage of 100 V. Thereafter, the BSA-RhB fluorescence was detected at the excitation light of 520 nm and the emission light of 605 nm with the Luminoimage analyzer (LAS-3000, Fujifilm Corporation, Tokyo, Japan). After detecting the fluorescence, the gel was stained with Coomassie blue G250 (Bio-rad, California, U.S.A.) to detect the Rubisco large subunit. The BSA-RhB fluorescence band density and the Coomassie blue-stained rbcL band density were quantified using Image J64 (NIH, Bethesda, Md.), and the BSA-RhB band density was normalized against the rbcL band density. SDS-PAGE was performed again based on the normalized data. The volume of the subjected crude protein in each sample was adjusted, in such a manner that the band density of Coomassie blue-stained rbcL bands would be equivalent to each other among all the tested samples, so as to attain the BSA-RhB band having the normalized fluorescence intensity. In addition, the calibration curve for the BSA-RhB intensity against the known amount (µg) of the BSA-RhB protein (the positive control) was prepared. The total amount of the BSA-RhB protein collected from the contacted leaf was calculated in accordance with the formulae below.

The total amount (µg) of the BSA-RhB protein extracted per contacted leaf=(the amount (µg) of the protein corresponding to the RhB intensity measured per lane of the gel/the volume (µl) of the subjected crude protein per lane of the gel)×the total volume (l) of the extracted crude protein.

The percentage (%) of the BSA-RhB protein extracted per contacted leaf=the total amount (µg) of the extracted BSA-RhB protein/the initial amount (2 µg) of the contacted protein×100.

Statistic Analysis

The obtained data are shown as the mean the standard deviation (SD) of the three tests. SPSS 22.0 (IBM Armonk, N.Y.) was used for statistic analysis. A statistic difference was determined at a statistic significance of p<0.05 via analysis of variance (ANOVA) and the Tukey's honestly significant difference (HSD) test.

(Results)

BSA delivery efficiency was quantified based on intact BSA-RhB collected from the contacted leaf. Tests were performed at various peptide/protein molar ratios, and the total protein derived from all the leaves was extracted 6 hours after the contact. The extracted protein lysate was analyzed via SDS-PAGE, and BSA-RhB (66 kDa) was excited and visualized under a fluorescent system.

Figure 3:
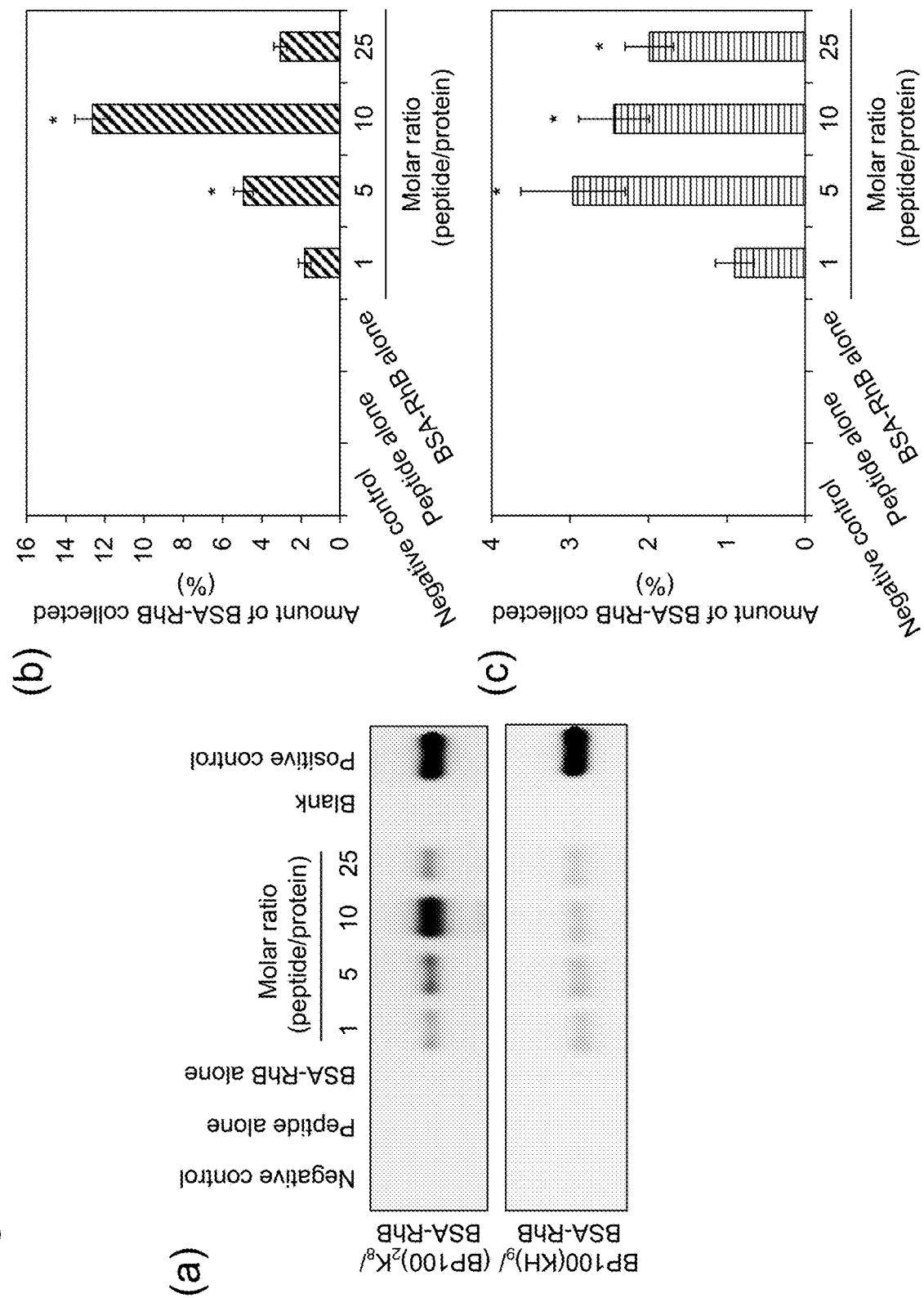
FIG. 3 shows delivery efficiency of the carrier peptide for BSA-RhB.

As shown in FIG. 3, BSA-RhB was extracted from the leaf only when the carrier peptide was used (FIG. 3). At all the peptide/protein molar ratios, the $(BP100)_2Ks$ fusion peptide exhibited the protein delivery capacity superior to that of the $BP100(KH)_9$ fusion peptide (FIG. 3). In the case of the $(BP100)_2K_8$ fusion peptide, the amount of the collected protein was the greatest at the peptide/protein molar ratio of 10. In the case of the $BP100(KH)_9$ fusion peptide, the amount of the collected protein was the greatest at the peptide/protein molar ratio of 5 (FIG. 3).

Subsequently, the $(BP100)_2K$/BSA-RhB complex was brought into contact with the an YFP-expressing *Arabidopsis thaliana* leaf at the peptide/protein molar ratio of 10 for 6 hours, and fluorescence images were then obtained via CLSM. YFP fluorescence expressed in the cytosol and the nucleus of the transgenic YFP-expressing *Arabidopsis thaliana* was used to distinguish the extracellular space from the intracellular space. The BSA-RhB signal was observed as early as 1 to 3 hours after the contact, the signal intensity reached the peak at 6 hours, the peak signal intensity was maintained at 12 to 24 hours, and the signal intensity was lowered at 48 hours after the contact (FIG. 4). While the BSA-RhB fluorescence was mainly observed on the extracellular surface 1 to 3 hours after the contact, the BSA-RhB fluorescence was observed to be colocalized with the YFP fluorescence 6 to 48 hours after the contact. This indicates that BSA-RhB was present in the intracellular space. In addition to the localization in the cytosol, the BSA-RhB signal was observed in the vacuole 6 to 24 hours after the contact.

Subsequently, intracellular delivery of a protein having a higher molecular weight; i.e., ADH (150 kDa), was examined at the peptide/protein molar ratio of 10, using (BP100)$_2$K$_8$ as the carrier peptide.

Figure 5:
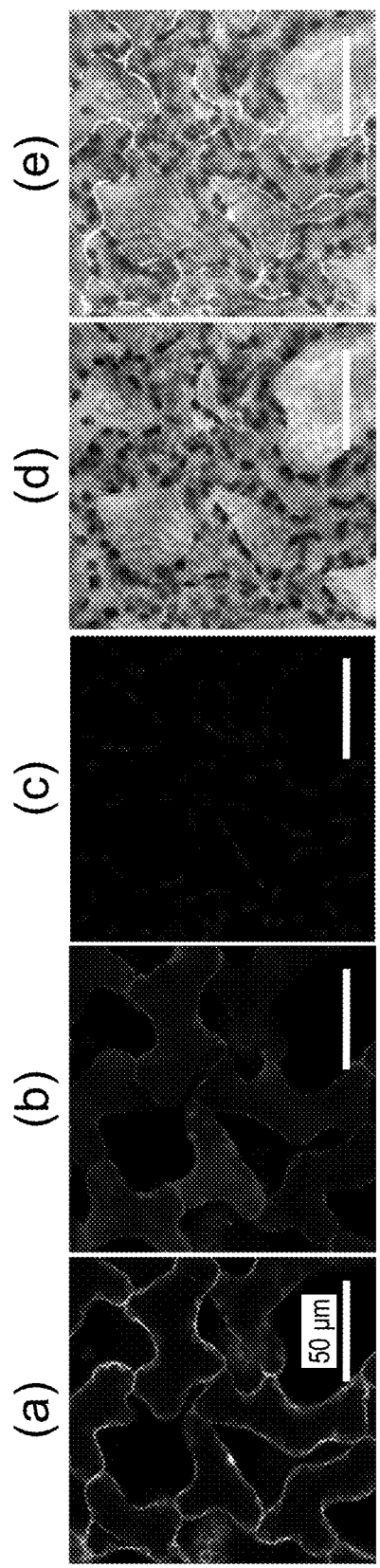
FIG. 5 shows the results of observation via CLSM of the leaf 6 hours after being contacting with the $(BP100)_2K$/ADH-RhB complex. A scale bar is 50 μm. (a) to (e)

ADH-RhB not forming the complex exhibited a negative zeta potential (−43.1±1.1 mV), and the hydrodynamic diameter thereof was 168±7 nm. The average hydrodynamic diameter of (BP100)$_2$Ks/ADH-RhB comprising the peptide and the protein at the peptide/protein molar ratio of 10 was 308±53 nm, the PDI value was 0.21±0.07, and the surface charge was 11.1±1.9 mV. An increase in the zeta potential from −43.1 mV to 11.1 mV indicates that the ADH-RhB surface is covered by cationic (BP100)$_2$K$_8$ and an ionic complex is formed. As a result of measurement by AFM, the (BP100)$_2$K/ADH-RhB complex was found to have a homogeneous spherical form (data not shown). Subsequently, an YFP-expressing *Arabidopsis thaliana* leaf was contacted with the complex for 6 hours, and fluorescence images were obtained via CLSM. As with the results observed in BSA delivery, ADH-RhB was detected in the cytosol and the vacuole 6 hours after the contact (FIG. 5). In addition, the ADH-RhB signal was detected in the wild-type *Arabidopsis thaliana* leaf that had been brought into contact with (BP100)$_2$K/ADH-RhB (data not shown). Thus, the fluorescence was found to be derived from ADH-RhB.

ADH-RhB was found to be collected from the leaf that was brought into contact with the (BP100)$_2$K/ADH-RhB complex by native PAGE (data not shown). The ADH-RhB signal was not detected in the leaf that had been brought into contact with ADH-RhB alone (data not shown). This verifies that ADH-RhB would not be transported to the cell in the absence of the carrier peptide. Success in ADH-RhB delivery indicates that the fusion peptide-mediated protein delivery system is effective for a protein having a relatively high molecular weight.

Example 3: Introduction of a Protein Comprising an Organelle Transit Sequence into a Cell (Method)
Preparation of *Arabidopsis thaliana* expressing GFP-PTS A transgenic *Arabidopsis thaliana* strain expressing GFP-PTS was prepared via *Agrobacterium tumefaciens* (EHA101)-mediated transformation of pMAT137 comprising the sGFP gene into wild-type *Arabidopsis thaliana* (Columbia) (Mano S. et al., Plant Cell Physiol., 2002, 43, pp. 331-341). The seeds were sowed in the Murashige and Skoog (MS) medium containing 1% agar and kanamycin. The kanamycin-resistant seedlings were germinated and maintained in MS medium for 1 week. Then, the plants were sowed in a pot containing a plant medium containing soil and vermiculite mixed at a ratio of 2:1. *Arabidopsis thaliana* was allowed to grow under long-day conditions (16-hour light period/8-hour dark period) at 21° C. in the Biotron NK system (Nippon Medical & Chemical Instruments Co., Ltd., Osaka, Japan).

Cell-Free Synthesis of Citrine, Citrine-NLS, and Citrine-PTS

The dialysis mode of cell-free synthesis (Numata K et al., Biomacromolecules, 2012, 13, pp. 3450-3455; and Spirin A. S. et al., Science, 1988, 242, pp. 1162-1164) was employed. Briefly, an internal solution (9 mL) containing a substrate, a buffer, a plasmid, and an enzyme necessary for transcription and translation was prepared. This solution was composed of 55 mM of HEPES-KOH (pH 7.5; containing 1.7 mM dithiothreitol), 68 µM of L(−)-5-formyl-5,6,7,8-tetrahydrofolic acid, 0.05% sodium azide, 4.0% polyethylene glycol (the average molecular weight: 8,000 g/mL), 210 mM of potassium glutaminate, 27.5 mM of ammonium acetate, 10.7 mM of magnesium acetate, 2.7 mL of an S30 extract, 1.2 mM of adenosine-5'-triphosphate (pH 7.0), 0.8 mM each of cytidine triphosphate (pH 7.0), guanosine-5'-triphosphate (pH 7.0), and uridine-5'-triphosphate (pH 7.0), 80 mM of creatine phosphate, 0.64 mM of 3',5'-cyclic adenosine monophosphate, 1.0 mM each of 20 amino acid species, 175 µg/mL of total RNA from *E. coli*, a plasmid construct (a pDES17-citrine plasmid, pDES17-citrine-NLS plasmid, or pDES17-citrine-PTS plasmid), 250 µg/mL of creatine kinase, and 93 µg/mL of T7 RNA polymerase. The S30 extract was prepared from the *E. coli* BL21 codon-plus RIL strain (Agilent technologies, Santa Clara, Calif., U.S.A.) in the manner described previously (Kitagawa T., J. Struct. Funct. Genomics, 2004, 5, pp. 63-68). Nine mL of the internal solution was dialyzed against 90 mL of the external solution via cell-free, large-scale dialysis, using a dialysis membrane with a molecular weight cut off of 15 kDa (Fisher Scientific, Waltham, Mass., U.S.A.). The reaction solution was incubated at 30° C. for 16 hours with stirring.

Purification of Citrine, Citrine-NLS, and Citrine-PTS

The internal solution (9 mL) was purified using the AKTA Express system (GE Healthcare, Little Chalfont, U.K.). The internal solution was centrifuged at 3,000×g for 30 minutes, and the supernatant was mixed with Buffer A (i.e., 20 mM Tris-HCl buffer (pH 8.0) containing 300 mM sodium chloride, 20 mM imidazole, and 1 mM tris(2-carboxyethyl) phosphine hydrochloride (TCEP, Hampton Research, Aliso, Viejo, Calif.)). The protein solution was applied to 5 mL of Histrap (GE Healthcare, Little Chalfont, U.K.), and resin was washed with a buffer. The protein was eluted with Buffer B (i.e., 20 mM Tris-HCl buffer containing 300 mM sodium chloride, 500 mM imidazole, and 1 mM TCEP).

The preparation of the peptide/protein complex at a molar ratio of 10, the contact with a plant cell, and evaluation thereof were carried out in the manner as described in Examples 1 and 2.

(Results)
Citrine conjugated to a nuclear localization signal (NLS) peptide targeting a nucleus and citrine conjugated to a peroxisomal targeting signal (PTS) targeting a peroxisome were used as protein models. Citrine containing no signal peptide was used as a negative control.

The citrine proteins and the citrine protein-(BP100)$_2$K$_8$ complexes were characterized by DLS, zeta potentials, and AFM. Based on the observation via AFM and size distribution graph, all the complexes were found to have homogenous spherical form (data not shown).

All the citrine proteins containing no carrier peptides exhibited negative zeta potentials, and hydrodynamic diameters thereof were about 200 nm (Table 4). The citrine protein-(BP100)$_2$Ks complexes were positively charged, and the sizes thereof were in the range of 218±13 nm to 263±7 nm (Table 5).

TABLE 4

Characterization of citrine, citrine-NLS, and citrine-PTS

| Protein | Hydrodynamic diameter (nm) | PDI | Zeta potential (mV) |
|---|---|---|---|
| Citrine | 188 ± 6 | 0.06 ± 0.02 | −11.3 ± 1.5 |
| Citrine-NLS | 196 ± 7 | 0.03 ± 0.00 | −7.37 ± 2.7 |
| Citrine-PTS | 190 ± 5 | 0.05 ± 0.01 | −12.1 ± 1.4 |

TABLE 5

Characterization of (BP100)$_2$K$_8$/citrine complex prepared at peptide/protein molar ratio of 10

| Protein in the complex | Hydrodynamic diameter (nm) | PDI | Zeta potential (mV) |
|---|---|---|---|
| Citrine | 263 ± 7 | 0.03 ± 0.03 | 20.1 ± 1.3 |
| Citrine-NLS | 218 ± 13 | 0.07 ± 0.04 | 23.9 ± 0.4 |
| Citrine-PTS | 253 ± 9 | 0.11 ± 0.04 | 17.9 ± 1.0 |

Citrine containing no organelle transit sequence was not localized in a particular region in a cell (FIG. 6). In contrast, citrine-NLS was found to be accumulated in a given region overlapping with a DAPI-stained region indicating a nuclear position 72 hours after the contact (FIG. 6b). As indicated by colocalization of citrine-PTS fluorescence and GFP-PTS fluorescence, citrine-PTS was localized in a peroxisome (FIG. 6d). Citrine-PTS was delivered to the peroxisome 12 hours after the contact.

These results demonstrate that the ability of delivering the carrier peptide/protein complex into a cell is not inhibited by the organelle transit sequence and that a protein can be delivered in an organelle-specific manner by adding the organelle transit sequence to the protein of the complex according to the present invention.

Example 4: Introduction of a Genome-Editing Module into a Cell (Method)
Preparation of GFP-Expressing Tomato and YFP-Expressing Poplar A GFP-expressing tomato was prepared via *Agrobacterium* transformation. More specifically, it was prepared in accordance with the method described in Sun H. J. et al., Plant Cell Physiol., 2006, 47, pp. 426-431.

An YFP-expressing poplar strain was prepared in accordance with the method described in Ohtani M. et al., Plant J., 2011, 67, pp. 499-512.

A GFP-expressing rice strain was prepared in accordance with the method described in Hiroaki Saika et al., Plant Cell Reports, 2009, Vol. 28, Issue 4, pp. 619-626.
Preparation of Cas9, gRNA, and Complex Thereof Based on the YFP gene sequence (SEQ ID NO: 41), guide RNAs (gRNAs) were prepared for two target sites (SEQ ID NO: 42 and SEQ ID NO: 43) using the MEGAscript T7 Transcription kit (Ambion) (the resulting gRNAs are designated as "Yfp1 gRNA" and "Yfp2 gRN," respectively). Cas9 was prepared via cell-free synthesis in the same manner as with citrine in Example 3, except that the plasmid construct was prepared by amplifying cDNA of Cas9 (the nucleotide sequence thereof is shown in SEQ ID NO: 50 and the amino acid sequence thereof is shown in SEQ ID NO: 51) using a forward primer (SEQ ID NO: 52) and a reverse primer (SEQ ID NO: 53), and introducing the amplified DNA fragment into the pDES™17 vector (Thermo Fisher Scientific, Waltham, Mass., U.S.A.). The crude Cas9 protein was purified via His trap affinity chromatography, ion exchange chromatography, and gel filtration chromatography. Cas9 (100 mM) and gRNAs (200 nM) were dissolved in a binding buffer (20 mM HEPES buffer, 150 mM potassium chloride, 10% glycerol, and 1 mM DTT), and the resulting solution was incubated at 22° C. for 15 minutes.
Preparation of TALEN Plasmid DNAs encoding TALEN-R and TALEN-L targeting YFP were prepared in accordance with the previous report (Nakagawa et al., Exp. Anim., 2014, 63, pp. 79-84). Briefly, the synthesized TALE repeats were cloned into pBluescript SK and assembled by the Golden cloning method (Ochiai H et al., 2013, Sci. Rep., 3, 3379). The N- and C-terminal domains of TALE were obtained from pTALEN_v2 (Addgene, Cambridge, Mass., U.S.A.) (Sanjana N. E. et al., Nat. Biotechnol., 31, 23-24). TCTTCAAGGACGACGGCAACT (SEQ ID NO: 54) and TCGCCCTCGAACTTCACCT (SEQ ID NO: 55) were used as YFP-targeting sequences to prepare L-TALEN and R-TALEN, respectively. In accordance with the manufacturer's instructions and Sakuma T. et al., Genes Cells, 18, 315-326, mRNAs of TALENs were prepared from a plasmid linearized by digestion with SmaI using the mMessage mMachine T7 Ultra Kit (Thermo Fisher Scientific, Waltham, Mass., U.S.A.), and purified using the RNeasy Mini Kit (Qiagen, Hilden, Germany). The TALEN proteins was prepared using the cell-free synthesis system in the same manner as with the case of citrine in Example 3, and purified via His trap affinity chromatography.
Preparation of Complex of Genome-Editing Module (TALEN or Cas9/gRNA) and Peptide A fusion peptide of BP100 and oligolysine; i.e., (BP100)$_2$K$_8$ (KKLFKKILKYLKKLFKKIL-KYLKKKKKKKK (SEQ ID NO: 23); theoretical pI/Mw: 10.75/3851.13 Da), was synthesized and purified in the manner described in Example 1 and the molecular weight thereof was measured. A peptide solution (0.4 μl, 1.0 mg/mL) was mixed with 99.6 μl of Cas9/gRNA (Cas9: 100 nm), and the mixture was incubated at 22° C. for 30 minutes to prepare a peptide/Cas9/gRNA complex. Also, 2 g of each TALEN was mixed with 320 mg of a peptide for 30 minutes, and the resulting mixture was suspended in ultrapure water (MilliQ water) (the final volume: 50 μl) to prepare a peptide/TALEN complex. The peptide/TALEN-R complex and the peptide/TALEN-L complex were mixed immediately before they were brought into contact with plants.
Bringing the Complex into Contact with Plants The complex was brought into contact with plants with a needleless syringe. As target plants, one or more plants selected from YFP-expressing *Arabidopsis thaliana*, YFP-expressing poplar, GFP-expressing microtomato (Microtom), and GFP-expressing rice were used. Prior to the contact, the plants were retained in a plant incubator at high light intensity of 90 mol/m$^2$ sec for about 8 hours in order to facilitate introduction. The mixed solution of the peptide/TALEN-R complex and the peptide/TALEN-L complex (100 1 in total) or the peptide/Cas9/gRNA complex was brought into contact with a plant leaf. Thereafter, plants were incubated under short-day conditions (8-hour light conditions/16-hour dark conditions).
Evaluation of Genome Editing Efficiency and Edited Sequence The contacted leaf was collected 1 day to 14 days after the contact for confocal laser scanning microscopic (CLSM) observation and DNA sequencing. Reporter gene silencing was observed via CLSM. Genomic DNA was extracted from the contacted leaf using the DNAeasy Mini Kit (Qiagen) for sequencing. The target sequence was amplified using the primers shown in Table 5 below and purified using the QIAquick Purification Kit (Qiagen). In the table, TALEN (foward-1) and TALEN (reverse-1), and TALEN (foward-2) and TALEN (reverse-2) are two sets of primers used for TALEN testing. Also, Cas9 (YFP1-foward) and Cas9 (YFP1-reverse), and Cas9 (YFP2-foward) and Cas9 (YFP2-reverse) are two sets of primers used for the target sites of YFP1 and YFP2, respectively, for Cas9 testing.

TABLE 6

| | Sequence | SEQ ID NO: |
|---|---|---|
| TALEN (foward-1) | CCTGAAGTTCATCTGCACCA | 44 |
| TALEN (reverse-1) | ATGCCGTTCTTCTGCTTGTC | 45 |
| TALEN (foward-2) | CACATGAAGCAGCACGACTTCTTCA | 56 |
| TALEN (reverse-2) | CTCGATGTTGTGGCGGATCTTGAAG | 57 |
| Cas9 (YFP1-foward) | TCGACATGCTACAGTGGTACC | 46 |
| Cas9 (YFP1-reverse) | CCGGACACGCTGAACTTGTGG | 47 |
| Cas9 (YFP2-foward) | ACGTAAACGGCCACAAGTTC | 48 |
| Cas9 (YFP2-reverse) | TCTTGTAGTTGCCGTCGTCC | 49 |

The PCR product was subcloned into the TA cloning kit (Toyobo Co., Ltd.) for DNA sequencing. A colony, which was obtained by transforming cloning vector into E. coli, and cultivating it on an LB agar medium at 37° C., was used to preform colony PCR, using the M13 forward primer (GTTTTCCCAGTCACGAC: SEQ ID NO: 28) and the M13 reverse primer (CAGGAAACAGCTATGAC: SEQ ID NO: 29).

(Results)

Cas9, gRNA, and TALEN were confirmed to be successfully prepared and purified via SDS-PAGE (data not shown).

The results of CLSM observation demonstrate that 3 days were sufficient for the YFP-targeting TALEN/peptide complex to edit and silence the YFP-expressing *Arabidopsis thaliana* genome (FIG. 7) (and no significant cytotoxicity was observed in the leaf appearance at this time (data not shown)). Subsequently, the extracted genome DNA was subcloned and sequenced. As a result, the target sequence was found to be edited with efficiency of about 5% (20/400 clones). The YFP-targeting TALEN/peptide complex was brought into contact with an YFP-expressing poplar leaf, and YFP silencing occurred 2 days thereafter (FIG. 8). In the case of the GFP-expressing microtomato (Micro-tom), GFP silencing occurred within 3 days (FIG. 9) (and no significant cytotoxicity was observed in the leaf appearance at this time (data not shown)).

The hydrodynamic diameters and zeta potentials of the complexes of Cas9, gRNA, Cas9-gRNA, and Cas9-gRNA and peptides (the peptide/Cas9-gRNA molar ratio of 1, 5, 10, or 25) are shown in FIG. 10.

Subsequently, the prepared Cas9/Yfp2 gRNA/peptide complex was examined. As a result, this complex could be introduced into an YFP-expressing *Arabidopsis thaliana* leaf, and YFP silencing was observed via CLSM (FIG. 11). As a result of analysing the genomic DNA sequence, genome editing was found to be successful (data not shown). It was also found that the Cas9/Yfp2 gRNA/peptide complex could be introduced into GFP-expressing microtomato and GFP-expressing rice, and it caused GFP silencing (FIG. 12 and FIG. 13, respectively).

The results demonstrate that the genome-editing modules can be introduced into a plant cell by the complex of the present invention and that a plant genome can be edited thereby.

Example 5: Introduction of NPT II into a Cell (Method)
Synthesis of NPT II

Neomycin phosphotransferase (NPT) II was synthesized using the dialysis mode of cell-free synthesis (Numata K et al., Biomacromolecules, 2012, 13, pp. 3450-3455; and Spirin A. S. et al., Science, 1988, 242, pp. 1162-1164). Briefly, the NPT II gene was amplified using, as a template, the pMpGWB401 binary vector (Ishizaki K et al., PLos One, 2015, 10: e0138876) and the following primers: ATATC-CATGGGGATTGAACAAGATGGATTGCACGC (SEQ ID NO: 58) and ATATGGATCCCGGAAGAACTCGT-CAAGAAGGCGAT (SEQ ID NO: 59). The amplified DNA fragment was cloned into the NcoI and BamHI sites of pET28b(+), and the sequence was confirmed. Thereafter, the cloned NPT II gene was amplified via two-step PCR in accordance with the previous report (Yabuki T et al., J. Struct. Funct. Genomics, 2007, 8: 173-191). Briefly, the first PCR was performed in 20 l of a reaction mixture containing 3 μl of 50-fold diluted buffer, 50 nM each of the forward primer and the reverse primer reacting with NPT II, 0.2 mM each deoxyribonucleotide triphosphate, 1×Expand Hi-Fi buffer (Roche), and 0.5 U Expand Hi-Fi enzyme (Roche). Subsequently, the second PCR was performed in 20 μl of a reaction mixture containing 5 l of 5-fold diluted first PCR product, 50 μM of T7P fragment (GCTCTTGTCAT-TGTGCTTCGCATGATTACGAATTCAGATCTC-GATCCCGCGAAAT TAATACGACTCACTATAGGGA-GACCACAACGGTTTCCCTCTAGAAATAATTTTGT TTAACTTTAAGAAGGAGATATACATATGAAAGAT-CATCTCATCCACAATCATCAC AAACAT-GAGCACGCTCATGCCGAACATACT-GAGAACCTGTACTTCCAGGG: SEQ ID NO: 60), 50 μM of T7T fragment (AATGATTGATT-GATCCCCGCCCAGCTGAGTTGGCTGCTGC-CACCGCTGAGCAATA ACTAGCAT-AACCCCTTGGGGCCTCTAAACGGGTCTTGAGG GGTTTTTTGCTGAAA GGAGGAACTATATCCGGA-TAACCTCGAGCTGCAGG-CATGCAAGCTTGGCGAAGC ACAATGACAAGAGC: SEQ ID NO: 61), 1 μM of U2 universal primer (GCTCTTGTCATTGTGCTTCG: SEQ ID NO: 62), 0.2 mM each of dNTP, 1×Expand Hi-Fi buffer, and 0.5 U Expand Hi-Fi enzyme. The His tag used in this test was modified from a naturally-occurring polyhistidine tag (Yabuki et al., supra).

Cell-free synthesis was performed in the same manner as in Example 3. Subsequently, the tagged NPT II protein was purified through nickel-nitrotriacetic acid agarose columns in the same manner as described previously (Numata K et al., Biochemistry, 2015, 54: 1401-1407). A protein yield was determined by the Bradford method using the Bio-Rad Protein Assay Kit, and using bovine serum albumin standards.

Synthesis of the Carrier Peptide, Preparation of the Complex, and Introduction Thereof into Cells (BP100)$_2$K$_8$ was synthesized in the manner described in Example 1. Subsequently, 2 μg (about 0.062 nmol) of NPT II was mixed with about 2.4 g (0.62 nmol) of a fusion peptide to form a complex. The solution of the complex (15 μl) containing 2 μg of NPT II was brought into contact with a plant with a needleless syringe and introduced into an apple leaf. The used apple variety was JM1, and leaves obtained from 1- to 2-week old apple trees grown by hydroponics in tap water were used.

The tree leaves were impregnated with a kanamycin-containing solution for 10 days (at 2 to 4 sites per leaf), and the cell death was evaluated by visually examining a change in tree leaf color (green to brown).

(Results)

As a result of 9-mL-scale cell-free synthesis, 6.3 mg of NPT II was obtained. Also, NPT II was confirmed to be prepared by CBB staining of the gel after SDS-PAGE (data not shown).

Preliminary tests were carried out at kanamycin concentration of 0, 25, 50, 75, 100, and 200 mg/l, and the optimal test concentration was determined to be 75 mg/mL (data not shown).

FIG. 14 shows the results of exposure of the tree leaf to the 75 mg/mL kanamycin solution. The apple leaf died 1 day after exposed to 75 mg/l kanamycin in a control experiment (water) not comprising NPT II, whereas the cells impregnated with NPT II survived for 2 days after exposed to 75 mg/mL kanamycin (FIG. 14*c*). In the presence of 75 mg/l kanamycin, some cells impregnated with NPT II died from 3 days after the exposure (FIG. 14 (*d*) to (*f*)).

The results demonstrate that antibiotics-resistant proteins can be introduced into plant cells by the complex according to the present invention.

All publications, patents, and patent applications cited herein are incorporated herein by reference in their entirety.

The invention claimed is:

1. A carrier peptide/protein complex formed by ionic interaction between a carrier peptide and a protein of interest,
   wherein the carrier peptide comprises the amino acid sequence of KKLFKKILKYLKKLFKKIL-KYLKKKKKKKK (SEQ ID NO: 23) or KKLFKKIL-KYLKHKHKHKHKHKHKHKHKH (SEQ ID NO: 24);
   and
   wherein the protein of interest is to be introduced into a target plant cell.

2. The complex according to claim 1, wherein the complex has an average hydrodynamic diameter of 150 to 700 nm.

3. The complex according to claim 1, wherein the protein of interest has a molecular weight of 5 kDa to 200 kDa.

4. The complex according to claim 1, wherein the protein of interest is TALEN-L or TALEN-R, ZFN, or Cas9.

5. A method for producing the carrier peptide/protein complex according to claim 1 comprising:

a step of mixing a carrier peptide with a protein of interest to form the carrier peptide/protein complex according to claim 1.

6. A method for introducing a protein of interest into a target plant cell comprising:

a step of mixing a carrier peptide with a protein of interest to form the carrier peptide/protein complex according to claim 1; and a step of bringing the resulting complex into contact with the target plant cell.

7. The method according to claim 5, wherein the carrier peptide is mixed with the protein of interest at a molar ratio of 2:1 to 25:1 in the step of forming a complex.

8. The method according to claim 5, wherein the target plant cell is obtained from a plant of Gramineae, Brassicaceae, Solanaceae, Leguminosae, or Salicaceae.

9. A kit for introducing a protein of interest into a target plant cell comprising:
   a protein of interest to be introduced into the target plant cell; and
   the carrier peptide as defined in claim 1.

10. The kit according to claim 9, wherein the protein of interest is TALEN-L or TALEN-R, ZFN, or Cas9.

* * * * *

SEQUENCE LISTING

```
<160> NUMBER OF SEQ ID NOS: 113

<210> SEQ ID NO 1
<211> LENGTH: 11
<212> TYPE: PRT
<213> ORGANISM: Artificial
<220> FEATURE:
<223> OTHER INFORMATION: Synthetic

<400> SEQUENCE: 1

Lys Lys Leu Phe Lys Lys Ile Leu Lys Tyr Leu
1               5                   10

<210> SEQ ID NO 2
<211> LENGTH: 18
<212> TYPE: PRT
<213> ORGANISM: Artificial
<220> FEATURE:
<223> OTHER INFORMATION: Synthetic

<400> SEQUENCE: 2

Arg Lys Lys Arg Arg Gln Arg Arg Arg Arg Lys Lys Arg Arg Gln Arg
1               5                   10                  15

Arg Arg

<210> SEQ ID NO 3
<211> LENGTH: 9
<212> TYPE: PRT
<213> ORGANISM: Artificial
<220> FEATURE:
<223> OTHER INFORMATION: Synthetic

<400> SEQUENCE: 3

Arg Lys Lys Arg Arg Gln Arg Arg Arg
1               5

<210> SEQ ID NO 4
<211> LENGTH: 12
<212> TYPE: PRT
<213> ORGANISM: Artificial
<220> FEATURE:
<223> OTHER INFORMATION: Synthetic

<400> SEQUENCE: 4

Pro Leu Ser Ser Ile Phe Ser Arg Ile Gly Asp Pro
1               5                   10
```

```
<210> SEQ ID NO 5
<211> LENGTH: 12
<212> TYPE: PRT
<213> ORGANISM: Artificial
<220> FEATURE:
<223> OTHER INFORMATION: Synthetic

<400> SEQUENCE: 5

Pro Ile Ser Ser Ile Phe Ser Arg Thr Gly Asp Pro
1               5                   10

<210> SEQ ID NO 6
<211> LENGTH: 12
<212> TYPE: PRT
<213> ORGANISM: Artificial
<220> FEATURE:
<223> OTHER INFORMATION: Synthetic

<400> SEQUENCE: 6

Ala Ile Ser Ser Ile Leu Ser Lys Thr Gly Asp Pro
1               5                   10

<210> SEQ ID NO 7
<211> LENGTH: 12
<212> TYPE: PRT
<213> ORGANISM: Artificial
<220> FEATURE:
<223> OTHER INFORMATION: Synthetic

<400> SEQUENCE: 7

Pro Ile Leu Ser Ile Phe Ser Lys Ile Gly Asp Leu
1               5                   10

<210> SEQ ID NO 8
<211> LENGTH: 12
<212> TYPE: PRT
<213> ORGANISM: Artificial
<220> FEATURE:
<223> OTHER INFORMATION: Synthetic

<400> SEQUENCE: 8

Pro Leu Ser Ser Ile Phe Ser Lys Ile Gly Asp Pro
1               5                   10

<210> SEQ ID NO 9
<211> LENGTH: 12
<212> TYPE: PRT
<213> ORGANISM: Artificial
<220> FEATURE:
<223> OTHER INFORMATION: Synthetic

<400> SEQUENCE: 9

Pro Leu Ser Ser Ile Phe Ser His Ile Gly Asp Pro
1               5                   10

<210> SEQ ID NO 10
<211> LENGTH: 12
<212> TYPE: PRT
<213> ORGANISM: Artificial
<220> FEATURE:
<223> OTHER INFORMATION: Synthetic

<400> SEQUENCE: 10

Pro Leu Ser Ser Ile Phe Ser Ser Ile Gly Asp Pro
1               5                   10

<210> SEQ ID NO 11
```

```
<211> LENGTH: 16
<212> TYPE: PRT
<213> ORGANISM: Artificial
<220> FEATURE:
<223> OTHER INFORMATION: Synthetic

<400> SEQUENCE: 11

Arg Gln Ile Lys Ile Trp Phe Gln Asn Arg Arg Met Lys Trp Lys Lys
1               5                   10                  15

<210> SEQ ID NO 12
<211> LENGTH: 34
<212> TYPE: PRT
<213> ORGANISM: Artificial
<220> FEATURE:
<223> OTHER INFORMATION: Synthetic

<400> SEQUENCE: 12

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Asp

<210> SEQ ID NO 13
<211> LENGTH: 16
<212> TYPE: PRT
<213> ORGANISM: Artificial
<220> FEATURE:
<223> OTHER INFORMATION: Synthetic

<400> SEQUENCE: 13

Ala Ala Val Ala Leu Leu Pro Ala Val Leu Leu Ala Leu Leu Ala Pro
1               5                   10                  15

<210> SEQ ID NO 14
<211> LENGTH: 12
<212> TYPE: PRT
<213> ORGANISM: Artificial
<220> FEATURE:
<223> OTHER INFORMATION: Synthetic

<400> SEQUENCE: 14

Ala Ala Val Leu Leu Pro Val Leu Leu Ala Ala Pro
1               5                   10

<210> SEQ ID NO 15
<211> LENGTH: 15
<212> TYPE: PRT
<213> ORGANISM: Artificial
<220> FEATURE:
<223> OTHER INFORMATION: Synthetic

<400> SEQUENCE: 15

Val Thr Val Leu Ala Leu Gly Ala Leu Ala Gly Val Gly Val Gly
1               5                   10                  15

<210> SEQ ID NO 16
<211> LENGTH: 17
<212> TYPE: PRT
<213> ORGANISM: Artificial
<220> FEATURE:
<223> OTHER INFORMATION: Synthetic

<400> SEQUENCE: 16

Gly Ala Leu Phe Leu Gly Trp Leu Gly Ala Ala Gly Ser Thr Met Gly
```

```
1               5                   10                  15

Ala

<210> SEQ ID NO 17
<211> LENGTH: 17
<212> TYPE: PRT
<213> ORGANISM: Artificial
<220> FEATURE:
<223> OTHER INFORMATION: Synthetic

<400> SEQUENCE: 17

Met Gly Leu Gly Leu His Leu Leu Val Leu Ala Ala Ala Leu Gln Gly
1               5                   10                  15

Ala

<210> SEQ ID NO 18
<211> LENGTH: 24
<212> TYPE: PRT
<213> ORGANISM: Artificial
<220> FEATURE:
<223> OTHER INFORMATION: Synthetic

<400> SEQUENCE: 18

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 19
<211> LENGTH: 26
<212> TYPE: PRT
<213> ORGANISM: Artificial
<220> FEATURE:
<223> OTHER INFORMATION: Synthetic

<400> SEQUENCE: 19

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 20
<211> LENGTH: 18
<212> TYPE: PRT
<213> ORGANISM: Artificial
<220> FEATURE:
<223> OTHER INFORMATION: Synthetic

<400> SEQUENCE: 20

Lys Leu Ala Leu Lys Leu Ala Leu Lys Ala Leu Lys Ala Ala Leu Lys
1               5                   10                  15

Leu Ala

<210> SEQ ID NO 21
<211> LENGTH: 8
<212> TYPE: PRT
<213> ORGANISM: Artificial
<220> FEATURE:
<223> OTHER INFORMATION: Synthetic

<400> SEQUENCE: 21

Lys Lys Lys Lys Lys Lys Lys Lys
1               5
```

-continued

<210> SEQ ID NO 22
<211> LENGTH: 18
<212> TYPE: PRT
<213> ORGANISM: Artificial
<220> FEATURE:
<223> OTHER INFORMATION: Synthetic

<400> SEQUENCE: 22

Lys His Lys His Lys His Lys His Lys His Lys His Lys His Lys His
1               5                   10                  15

Lys His

<210> SEQ ID NO 23
<211> LENGTH: 30
<212> TYPE: PRT
<213> ORGANISM: Artificial
<220> FEATURE:
<223> OTHER INFORMATION: Synthetic

<400> SEQUENCE: 23

Lys Lys Leu Phe Lys Lys Ile Leu Lys Tyr Leu Lys Lys Leu Phe Lys
1               5                   10                  15

Lys Ile Leu Lys Tyr Leu Lys Lys Lys Lys Lys Lys Lys Lys
            20                  25                  30

<210> SEQ ID NO 24
<211> LENGTH: 29
<212> TYPE: PRT
<213> ORGANISM: Artificial
<220> FEATURE:
<223> OTHER INFORMATION: Synthetic

<400> SEQUENCE: 24

Lys Lys Leu Phe Lys Lys Ile Leu Lys Tyr Leu Lys His Lys His Lys
1               5                   10                  15

His Lys His Lys His Lys His Lys His Lys His Lys His
            20                  25

<210> SEQ ID NO 25
<211> LENGTH: 582
<212> TYPE: PRT
<213> ORGANISM: Planomicrobium okeanokoites

<400> SEQUENCE: 25

Met Phe Leu Ser Met Val Ser Lys Ile Arg Thr Phe Gly Trp Val Gln
1               5                   10                  15

Asn Pro Gly Lys Phe Glu Asn Leu Lys Arg Val Val Gln Val Phe Asp
            20                  25                  30

Arg Asn Ser Lys Val His Asn Glu Val Lys Asn Ile Lys Ile Pro Thr
        35                  40                  45

Leu Val Lys Glu Ser Lys Ile Gln Lys Glu Leu Val Ala Ile Met Asn
    50                  55                  60

Gln His Asp Leu Ile Tyr Thr Tyr Lys Glu Leu Val Gly Thr Gly Thr
65                  70                  75                  80

Ser Ile Arg Ser Glu Ala Pro Cys Asp Ala Ile Ile Gln Ala Thr Ile
                85                  90                  95

Ala Asp Gln Gly Asn Lys Lys Gly Tyr Ile Asp Asn Trp Ser Ser Asp
            100                 105                 110

Gly Phe Leu Arg Trp Ala His Ala Leu Gly Phe Ile Glu Tyr Ile Asn
        115                 120                 125

```
Lys Ser Asp Ser Phe Val Ile Thr Asp Val Gly Leu Ala Tyr Ser Lys
    130                 135                 140

Ser Ala Asp Gly Ser Ala Ile Glu Lys Glu Ile Leu Ile Glu Ala Ile
145                 150                 155                 160

Ser Ser Tyr Pro Pro Ala Ile Arg Ile Leu Thr Leu Leu Glu Asp Gly
                165                 170                 175

Gln His Leu Thr Lys Phe Asp Leu Gly Lys Asn Leu Gly Phe Ser Gly
            180                 185                 190

Glu Ser Gly Phe Thr Ser Leu Pro Glu Gly Ile Leu Leu Asp Thr Leu
        195                 200                 205

Ala Asn Ala Met Pro Lys Asp Lys Gly Ile Arg Asn Asn Trp Glu Gly
210                 215                 220

Ser Ser Asp Lys Tyr Ala Arg Met Ile Gly Gly Trp Leu Asp Lys Leu
225                 230                 235                 240

Gly Leu Val Lys Gln Gly Lys Lys Glu Phe Ile Ile Pro Thr Leu Gly
                245                 250                 255

Lys Pro Asp Asn Lys Glu Phe Ile Ser His Ala Phe Lys Ile Thr Gly
            260                 265                 270

Glu Gly Leu Lys Val Leu Arg Arg Ala Lys Gly Ser Thr Lys Phe Thr
        275                 280                 285

Arg Val Pro Lys Arg Val Tyr Trp Glu Met Leu Ala Thr Asn Leu Thr
290                 295                 300

Asp Lys Glu Tyr Val Arg Thr Arg Arg Ala Leu Ile Leu Glu Ile Leu
305                 310                 315                 320

Ile Lys Ala Gly Ser Leu Lys Ile Glu Gln Ile Gln Asp Asn Leu Lys
                325                 330                 335

Lys Leu Gly Phe Asp Glu Val Ile Glu Thr Ile Glu Asn Asp Ile Lys
            340                 345                 350

Gly Leu Ile Asn Thr Gly Ile Phe Ile Glu Ile Lys Gly Arg Phe Tyr
        355                 360                 365

Gln Leu Lys Asp His Ile Leu Gln Phe Val Ile Pro Asn Arg Gly Val
    370                 375                 380

Thr Lys Gln Leu Val Lys Ser Glu Leu Glu Glu Lys Lys Ser Glu Leu
385                 390                 395                 400

Arg His Lys Leu Lys Tyr Val Pro His Glu Tyr Ile Glu Leu Ile Glu
                405                 410                 415

Ile Ala Arg Asn Ser Thr Gln Asp Arg Ile Leu Glu Met Lys Val Met
            420                 425                 430

Glu Phe Phe Met Lys Val Tyr Gly Tyr Arg Gly Lys His Leu Gly Gly
        435                 440                 445

Ser Arg Lys Pro Asp Gly Ala Ile Tyr Thr Val Gly Ser Pro Ile Asp
    450                 455                 460

Tyr Gly Val Ile Val Asp Thr Lys Ala Tyr Ser Gly Gly Tyr Asn Leu
465                 470                 475                 480

Pro Ile Gly Gln Ala Asp Glu Met Gln Arg Tyr Val Glu Glu Asn Gln
                485                 490                 495

Thr Arg Asn Lys His Ile Asn Pro Asn Glu Trp Trp Lys Val Tyr Pro
            500                 505                 510

Ser Ser Val Thr Glu Phe Lys Phe Leu Phe Val Ser Gly His Phe Lys
        515                 520                 525

Gly Asn Tyr Lys Ala Gln Leu Thr Arg Leu Asn His Ile Thr Asn Cys
    530                 535                 540

Asn Gly Ala Val Leu Ser Val Glu Glu Leu Leu Ile Gly Gly Glu Met
```

-continued

```
                545                 550                 555                 560
Ile Lys Ala Gly Thr Leu Thr Leu Glu Glu Val Arg Arg Lys Phe Asn
                565                 570                 575
Asn Gly Glu Ile Asn Phe
                580

<210> SEQ ID NO 26
<211> LENGTH: 34
<212> TYPE: PRT
<213> ORGANISM: Artificial
<220> FEATURE:
<223> OTHER INFORMATION: Synthetic

<400> SEQUENCE: 26

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
                20                  25                  30

His Gly

<210> SEQ ID NO 27
<211> LENGTH: 34
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (12)..(13)
<223> OTHER INFORMATION: Xaa can be any naturally occurring amino acid

<400> SEQUENCE: 27

Leu Thr Pro Glu Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
                20                  25                  30

His Gly

<210> SEQ ID NO 28
<211> LENGTH: 17
<212> TYPE: DNA
<213> ORGANISM: Artificial
<220> FEATURE:
<223> OTHER INFORMATION: Primer

<400> SEQUENCE: 28
gttttcccag tcacgac                                                    17

<210> SEQ ID NO 29
<211> LENGTH: 17
<212> TYPE: DNA
<213> ORGANISM: Artificial
<220> FEATURE:
<223> OTHER INFORMATION: Primer

<400> SEQUENCE: 29
caggaaacag ctatgac                                                    17

<210> SEQ ID NO 30
<211> LENGTH: 1368
<212> TYPE: PRT
<213> ORGANISM: Streptococcus pyogenes

<400> SEQUENCE: 30
```

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415
```

-continued

Gly Glu Leu His Ala Ile Leu Arg Arg Gln Asp Phe Tyr Pro Phe
            420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
        500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
        580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
        660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
        820                 825                 830

Leu Ser Asp Tyr Asp Val Asp His Ile Val Pro Gln Ser Phe Leu Lys

-continued

```
                835                 840                 845
Asp Asp Ser Ile Asp Asn Lys Val Leu Thr Arg Ser Asp Lys Asn Arg
        850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
        930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys  Tyr Pro Lys Leu Glu  Ser Glu Phe
            995                 1000                 1005
Val Tyr  Gly Asp Tyr Lys Val  Tyr Asp Val Arg Lys  Met Ile Ala
1010                 1015                 1020
Lys Ser  Glu Gln Glu Ile Gly  Lys Ala Thr Ala Lys  Tyr Phe Phe
1025                 1030                 1035
Tyr Ser  Asn Ile Met Asn Phe  Phe Lys Thr Glu Ile  Thr Leu Ala
1040                 1045                 1050
Asn Gly  Glu Ile Arg Lys Arg  Pro Leu Ile Glu Thr  Asn Gly Glu
1055                 1060                 1065
Thr Gly  Glu Ile Val Trp Asp  Lys Gly Arg Asp Phe  Ala Thr Val
1070                 1075                 1080
Arg Lys  Val Leu Ser Met Pro  Gln Val Asn Ile Val  Lys Lys Thr
1085                 1090                 1095
Glu Val  Gln Thr Gly Gly Phe  Ser Lys Glu Ser Ile  Leu Pro Lys
1100                 1105                 1110
Arg Asn  Ser Asp Lys Leu Ile  Ala Arg Lys Lys Asp  Trp Asp Pro
1115                 1120                 1125
Lys Lys  Tyr Gly Gly Phe Asp  Ser Pro Thr Val Ala  Tyr Ser Val
1130                 1135                 1140
Leu Val  Val Ala Lys Val Glu  Lys Gly Lys Ser Lys  Lys Leu Lys
1145                 1150                 1155
Ser Val  Lys Glu Leu Leu Gly  Ile Thr Ile Met Glu  Arg Ser Ser
1160                 1165                 1170
Phe Glu  Lys Asn Pro Ile Asp  Phe Leu Glu Ala Lys  Gly Tyr Lys
1175                 1180                 1185
Glu Val  Lys Lys Asp Leu Ile  Ile Lys Leu Pro Lys  Tyr Ser Leu
1190                 1195                 1200
Phe Glu  Leu Glu Asn Gly Arg  Lys Arg Met Leu Ala  Ser Ala Gly
1205                 1210                 1215
Glu Leu  Gln Lys Gly Asn Glu  Leu Ala Leu Pro Ser  Lys Tyr Val
1220                 1225                 1230
Asn Phe  Leu Tyr Leu Ala Ser  His Tyr Glu Lys Leu  Lys Gly Ser
1235                 1240                 1245
```

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 31
<211> LENGTH: 7
<212> TYPE: PRT
<213> ORGANISM: Artificial
<220> FEATURE:
<223> OTHER INFORMATION: Synthetic

<400> SEQUENCE: 31

Pro Lys Lys Lys Arg Lys Val
1               5

<210> SEQ ID NO 32
<211> LENGTH: 3
<212> TYPE: PRT
<213> ORGANISM: Artificial
<220> FEATURE:
<223> OTHER INFORMATION: Synthetic

<400> SEQUENCE: 32

Ser Lys Leu
1

<210> SEQ ID NO 33
<211> LENGTH: 32
<212> TYPE: PRT
<213> ORGANISM: Artificial
<220> FEATURE:
<223> OTHER INFORMATION: Synthetic

<400> SEQUENCE: 33

Met Ala Met Ala Met Arg Ser Thr Phe Ala Arg Val Gly Ala Lys
1               5                   10                  15

Pro Ala Val Arg Gly Ala Arg Pro Ala Ser Arg Met Ser Cys Met Ala
            20                  25                  30

<210> SEQ ID NO 34
<211> LENGTH: 32
<212> TYPE: PRT
<213> ORGANISM: Artificial
<220> FEATURE:
<223> OTHER INFORMATION: Synthetic

<400> SEQUENCE: 34

Met Gln Val Thr Met Lys Ser Ser Ala Val Ser Gly Gln Arg Val Gly
1               5                   10                  15

Gly Ala Arg Val Ala Thr Arg Ser Val Arg Arg Ala Gln Leu Gln Val
            20                  25                  30

<210> SEQ ID NO 35
<211> LENGTH: 74
<212> TYPE: PRT
<213> ORGANISM: Artificial
<220> FEATURE:
<223> OTHER INFORMATION: Synthetic

<400> SEQUENCE: 35

Met Ala Thr Met Val Ala Gly Ile Ser Leu Arg Gly Pro Val Met Ser
1               5                   10                  15

Ser His Arg Thr Phe Ser Val Thr Lys Arg Ala Ser Leu Pro Gln Ser
            20                  25                  30

Lys Leu Ser Ser Glu Leu Ser Phe Val Thr Ser Gln Leu Ser Gly Leu
        35                  40                  45

Lys Ile Ser Ser Thr His Phe Ile Ser Ser Ala Pro Leu Ser Val
    50                  55                  60

Pro Phe Lys Pro Ser Leu Gln Pro Val Ala
65                  70

<210> SEQ ID NO 36
<211> LENGTH: 41
<212> TYPE: PRT
<213> ORGANISM: Artificial
<220> FEATURE:
<223> OTHER INFORMATION: Synthetic

<400> SEQUENCE: 36

Met Ala Ala Leu Gln Ser Ser Phe Ala Gly Leu Ser Thr Ser Phe Phe
1               5                   10                  15

Gly Gln Arg Phe Ser Pro Pro Leu Ser Leu Pro Pro Leu Val Lys Ser
            20                  25                  30

Thr Glu Gly Pro Cys Leu Ile Gln Ala
        35                  40

<210> SEQ ID NO 37
<211> LENGTH: 51
<212> TYPE: PRT
<213> ORGANISM: Artificial
<220> FEATURE:
<223> OTHER INFORMATION: Synthetic

<400> SEQUENCE: 37

Met Ala Val Ser Phe Ser Leu Val Gly Ala Phe Lys Gly Leu Ser Leu
1               5                   10                  15

Ala Ser Ser Ser Ser Phe Leu Lys Gly Asp Phe Gly Ala Ala Phe Pro
            20                  25                  30

Val Ala Pro Lys Phe Ser Val Ser Phe Pro Leu Lys Ser Pro Leu Thr
        35                  40                  45

Ile Glu Ser
    50

<210> SEQ ID NO 38
<211> LENGTH: 57
<212> TYPE: PRT
<213> ORGANISM: Artificial
<220> FEATURE:
<223> OTHER INFORMATION: Synthetic

<400> SEQUENCE: 38

```
Met Ala Ser Ser Val Leu Ser Ser Ala Val Ala Thr Arg Ser Asn
1               5                   10                  15

Val Ala Gln Ala Asn Met Val Ala Pro Phe Thr Gly Leu Lys Ser Ala
            20                  25                  30

Ala Ser Phe Pro Val Ser Arg Lys Gln Asn Leu Asp Ile Thr Ser Ile
        35                  40                  45

Ala Ser Asn Gly Gly Arg Val Gln Cys
    50                  55
```

<210> SEQ ID NO 39
<211> LENGTH: 39
<212> TYPE: PRT
<213> ORGANISM: Artificial
<220> FEATURE:
<223> OTHER INFORMATION: Synthetic

<400> SEQUENCE: 39

```
Met Ala Ala Ser Thr Met Ala Leu Ser Ser Pro Ala Phe Ala Gly Lys
1               5                   10                  15

Ala Val Lys Leu Ser Pro Ala Ala Ser Glu Val Leu Gly Ser Gly Arg
            20                  25                  30

Val Thr Met Arg Lys Thr Val
        35
```

<210> SEQ ID NO 40
<211> LENGTH: 12
<212> TYPE: PRT
<213> ORGANISM: Artificial
<220> FEATURE:
<223> OTHER INFORMATION: Synthetic

<400> SEQUENCE: 40

```
Met Leu Ser Leu Arg Gln Ser Ile Arg Phe Phe Lys
1               5                   10
```

<210> SEQ ID NO 41
<211> LENGTH: 921
<212> TYPE: DNA
<213> ORGANISM: Artificial
<220> FEATURE:
<223> OTHER INFORMATION: Synthetic

<400> SEQUENCE: 41

| | | | | | |
|---|---|---|---|---|---|
| acagggtacc | cggggatcct | ctagagccac | gtccctcatg | tcgacatgct | acagtggtac | 60 |
| cactcgtgag | gtaagattat | cgatatttaa | attatttatt | tcttcttttc | cattttttttg | 120 |
| gctaacattt | tccatggttt | tatgatatca | tgcaggtacg | agcgctcgag | gcgggtatcg | 180 |
| cgataggcct | gctgcagggg | gcggtgagca | agggcgagga | gctgttcacc | ggggtggtgc | 240 |
| ccatcctggt | cgagctggac | ggcgacgtaa | acggccacaa | gttcagcgtg | tccggcgagg | 300 |
| gcgagggcga | tgccacctac | ggcaagctga | ccctgaagtt | catctgcacc | accggcaagc | 360 |
| tgcccgtgcc | ctggcccacc | ctcgtgacca | ccttcggcta | cggcctgcag | tgcttcgccc | 420 |
| gctaccccga | ccacatgaag | cagcacgact | tcttcaagtc | cgccatgccc | gaaggctacg | 480 |
| tccaggagcg | caccatcttc | ttcaaggacg | acggcaacta | caagacccgc | gccgaggtga | 540 |
| agttcgaggg | cgacaccctg | gtgaaccgca | tcgagctgaa | gggcatcgac | ttcaaggagg | 600 |
| acggcaacat | cctggggcac | aagctggagt | acaactacaa | cagccacaac | gtctatatca | 660 |
| tggccgacaa | gcagaagaac | ggcatcaagg | tgaacttcaa | gatccgccac | aacatcgagg | 720 |

```
acggcagcgt gcagctcgcc gaccactacc agcagaacac ccccatcggc gacggccccg    780
tgctgctgcc cgacaaccac tacctgagct accagtccgc cctgagcaaa gaccccaacg    840
agaagcgcga tcacatggtc ctgctggagt tcgtgaccgc cgccgggatc actctcggca    900
tggacgagct gtacaagtaa a                                              921
```

<210> SEQ ID NO 42
<211> LENGTH: 28
<212> TYPE: DNA
<213> ORGANISM: Artificial
<220> FEATURE:
<223> OTHER INFORMATION: Synthetic

<400> SEQUENCE: 42

```
ggcctgctgc aggggggcggt gagcaagg                                       28
```

<210> SEQ ID NO 43
<211> LENGTH: 23
<212> TYPE: DNA
<213> ORGANISM: Artificial
<220> FEATURE:
<223> OTHER INFORMATION: Synthetic

<400> SEQUENCE: 43

```
ccggcaagct gcccgtgccc tgg                                             23
```

<210> SEQ ID NO 44
<211> LENGTH: 20
<212> TYPE: DNA
<213> ORGANISM: Artificial
<220> FEATURE:
<223> OTHER INFORMATION: Primer

<400> SEQUENCE: 44

```
cctgaagttc atctgcacca                                                 20
```

<210> SEQ ID NO 45
<211> LENGTH: 20
<212> TYPE: DNA
<213> ORGANISM: Artificial
<220> FEATURE:
<223> OTHER INFORMATION: Primer

<400> SEQUENCE: 45

```
atgccgttct tctgcttgtc                                                 20
```

<210> SEQ ID NO 46
<211> LENGTH: 21
<212> TYPE: DNA
<213> ORGANISM: Artificial
<220> FEATURE:
<223> OTHER INFORMATION: Primer

<400> SEQUENCE: 46

```
tcgacatgct acagtggtac c                                               21
```

<210> SEQ ID NO 47
<211> LENGTH: 21
<212> TYPE: DNA
<213> ORGANISM: Artificial
<220> FEATURE:
<223> OTHER INFORMATION: Primer

<400> SEQUENCE: 47

```
ccggacacgc tgaacttgtg g                                               21
```

<210> SEQ ID NO 48
<211> LENGTH: 20
<212> TYPE: DNA
<213> ORGANISM: Artificial
<220> FEATURE:
<223> OTHER INFORMATION: Primer

<400> SEQUENCE: 48
acgtaaacgg ccacaagttc					20

<210> SEQ ID NO 49
<211> LENGTH: 20
<212> TYPE: DNA
<213> ORGANISM: Artificial
<220> FEATURE:
<223> OTHER INFORMATION: Primer

<400> SEQUENCE: 49
tcttgtagtt gccgtcgtcc					20

<210> SEQ ID NO 50
<211> LENGTH: 4275
<212> TYPE: DNA
<213> ORGANISM: Homo sapiens
<220> FEATURE:
<221> NAME/KEY: CDS
<222> LOCATION: (1)..(4275)

<400> SEQUENCE: 50

```
atg gac tat aag gac cac gac gga gac tac aag gat cat gat att gat         48
Met Asp Tyr Lys Asp His Asp Gly Asp Tyr Lys Asp His Asp Ile Asp
1               5                   10                  15 tac aaa gac gat gac gat aag atg gcc cca aag aag aag cgg aag gtc         96
Tyr Lys Asp Asp Asp Asp Lys Met Ala Pro Lys Lys Lys Arg Lys Val
            20                  25                  30 ggt atc cac gga gtc cca gca gcc gac aag aag tac agc atc ggc ctg        144
Gly Ile His Gly Val Pro Ala Ala Asp Lys Lys Tyr Ser Ile Gly Leu
        35                  40                  45 gac atc ggc acc aac tct gtg ggc tgg gcc gtg atc acc gac gag tac        192
Asp Ile Gly Thr Asn Ser Val Gly Trp Ala Val Ile Thr Asp Glu Tyr
    50                  55                  60 aag gtg ccc agc aag aaa ttc aag gtg ctg ggc aac acc gac cgg cac        240
Lys Val Pro Ser Lys Lys Phe Lys Val Leu Gly Asn Thr Asp Arg His
65                  70                  75                  80 agc atc aag aag aac ctg atc gga gcc ctg ctg ttc gac agc ggc gaa        288
Ser Ile Lys Lys Asn Leu Ile Gly Ala Leu Leu Phe Asp Ser Gly Glu
                85                  90                  95 aca gcc gag gcc acc cgg ctg aag aga acc gcc aga aga aga tac acc        336
Thr Ala Glu Ala Thr Arg Leu Lys Arg Thr Ala Arg Arg Arg Tyr Thr
            100                 105                 110 aga cgg aag aac cgg atc tgc tat ctg caa gag atc ttc agc aac gag        384
Arg Arg Lys Asn Arg Ile Cys Tyr Leu Gln Glu Ile Phe Ser Asn Glu
        115                 120                 125 atg gcc aag gtg gac gac agc ttc ttc cac aga ctg gaa gag tcc ttc        432
Met Ala Lys Val Asp Asp Ser Phe Phe His Arg Leu Glu Glu Ser Phe
    130                 135                 140 ctg gtg gaa gag gat aag aag cac gag cgg cac ccc atc ttc ggc aac        480
Leu Val Glu Glu Asp Lys Lys His Glu Arg His Pro Ile Phe Gly Asn
145                 150                 155                 160 atc gtg gac gag gtg gcc tac cac gag aag tac ccc acc atc tac cac        528
Ile Val Asp Glu Val Ala Tyr His Glu Lys Tyr Pro Thr Ile Tyr His
                165                 170                 175
```

```
ctg aga aag aaa ctg gtg gac agc acc gac aag gcc gac ctg cgg ctg      576
Leu Arg Lys Lys Leu Val Asp Ser Thr Asp Lys Ala Asp Leu Arg Leu
        180                 185                 190 atc tat ctg gcc ctg gcc cac atg atc aag ttc cgg ggc cac ttc ctg      624
Ile Tyr Leu Ala Leu Ala His Met Ile Lys Phe Arg Gly His Phe Leu
            195                 200                 205 atc gag ggc gac ctg aac ccc gac aac agc gac gtg gac aag ctg ttc      672
Ile Glu Gly Asp Leu Asn Pro Asp Asn Ser Asp Val Asp Lys Leu Phe
210                 215                 220 atc cag ctg gtg cag acc tac aac cag ctg ttc gag gaa aac ccc atc      720
Ile Gln Leu Val Gln Thr Tyr Asn Gln Leu Phe Glu Glu Asn Pro Ile
225                 230                 235                 240 aac gcc agc ggc gtg gac gcc aag gcc atc ctg tct gcc aga ctg agc      768
Asn Ala Ser Gly Val Asp Ala Lys Ala Ile Leu Ser Ala Arg Leu Ser
            245                 250                 255 aag agc aga cgg ctg gaa aat ctg atc gcc cag ctg ccc ggc gag aag      816
Lys Ser Arg Arg Leu Glu Asn Leu Ile Ala Gln Leu Pro Gly Glu Lys
        260                 265                 270 aag aat ggc ctg ttc gga aac ctg att gcc ctg agc ctg ggc ctg acc      864
Lys Asn Gly Leu Phe Gly Asn Leu Ile Ala Leu Ser Leu Gly Leu Thr
    275                 280                 285 ccc aac ttc aag agc aac ttc gac ctg gcc gag gat gcc aaa ctg cag      912
Pro Asn Phe Lys Ser Asn Phe Asp Leu Ala Glu Asp Ala Lys Leu Gln
290                 295                 300 ctg agc aag gac acc tac gac gac gac ctg gac aac ctg ctg gcc cag      960
Leu Ser Lys Asp Thr Tyr Asp Asp Asp Leu Asp Asn Leu Leu Ala Gln
305                 310                 315                 320 atc ggc gac cag tac gcc gac ctg ttt ctg gcc gcc aag aac ctg tcc     1008
Ile Gly Asp Gln Tyr Ala Asp Leu Phe Leu Ala Ala Lys Asn Leu Ser
            325                 330                 335 gac gcc atc ctg ctg agc gac atc ctg aga gtg aac acc gag atc acc     1056
Asp Ala Ile Leu Leu Ser Asp Ile Leu Arg Val Asn Thr Glu Ile Thr
        340                 345                 350 aag gcc ccc ctg agc gcc tct atg atc aag aga tac gac gag cac cac     1104
Lys Ala Pro Leu Ser Ala Ser Met Ile Lys Arg Tyr Asp Glu His His
    355                 360                 365 cag gac ctg acc ctg ctg aaa gct ctc gtg cgg cag cag ctg cct gag     1152
Gln Asp Leu Thr Leu Leu Lys Ala Leu Val Arg Gln Gln Leu Pro Glu
370                 375                 380 aag tac aaa gag att ttc ttc gac cag agc aag aac ggc tac gcc ggc     1200
Lys Tyr Lys Glu Ile Phe Phe Asp Gln Ser Lys Asn Gly Tyr Ala Gly
385                 390                 395                 400 tac att gac ggc gga gcc agc cag gaa gag ttc tac aag ttc atc aag     1248
Tyr Ile Asp Gly Gly Ala Ser Gln Glu Glu Phe Tyr Lys Phe Ile Lys
            405                 410                 415 ccc atc ctg gaa aag atg gac ggc acc gag gaa ctg ctc gtg aag ctg     1296
Pro Ile Leu Glu Lys Met Asp Gly Thr Glu Glu Leu Leu Val Lys Leu
        420                 425                 430 aac aga gag gac ctg ctg cgg aag cag cgg acc ttc gac aac ggc agc     1344
Asn Arg Glu Asp Leu Leu Arg Lys Gln Arg Thr Phe Asp Asn Gly Ser
    435                 440                 445 atc ccc cac cag atc cac ctg gga gag ctg cac gcc att ctg cgg cgg     1392
Ile Pro His Gln Ile His Leu Gly Glu Leu His Ala Ile Leu Arg Arg
450                 455                 460 cag gaa gat ttt tac cca ttc ctg aag gac aac cgg gaa aag atc gag     1440
Gln Glu Asp Phe Tyr Pro Phe Leu Lys Asp Asn Arg Glu Lys Ile Glu
465                 470                 475                 480 aag atc ctg acc ttc cgc atc ccc tac tac gtg ggc cct ctg gcc agg     1488
Lys Ile Leu Thr Phe Arg Ile Pro Tyr Tyr Val Gly Pro Leu Ala Arg
```

-continued

|  |  |  |  |  |  |  |  |  |  |  |  |  |  |  |  |
|---|---|---|---|---|---|---|---|---|---|---|---|---|---|---|---|
|  |  |  | 485 |  |  |  |  | 490 |  |  |  |  | 495 |  |  |
| gga | aac | agc | aga | ttc | gcc | tgg | atg | acc | aga | aag | agc | gag | gaa | acc | atc | 1536 |
| Gly | Asn | Ser | Arg | Phe | Ala | Trp | Met | Thr | Arg | Lys | Ser | Glu | Glu | Thr | Ile |
|  |  |  | 500 |  |  |  |  | 505 |  |  |  |  | 510 |  |  |
| acc | ccc | tgg | aac | ttc | gag | gaa | gtg | gtg | gac | aag | ggc | gct | tcc | gcc | cag | 1584 |
| Thr | Pro | Trp | Asn | Phe | Glu | Glu | Val | Val | Asp | Lys | Gly | Ala | Ser | Ala | Gln |
| 515 |  |  |  |  | 520 |  |  |  |  | 525 |  |  |  |  |  |
| agc | ttc | atc | gag | cgg | atg | acc | aac | ttc | gat | aag | aac | ctg | ccc | aac | gag | 1632 |
| Ser | Phe | Ile | Glu | Arg | Met | Thr | Asn | Phe | Asp | Lys | Asn | Leu | Pro | Asn | Glu |
| 530 |  |  |  |  | 535 |  |  |  |  | 540 |  |  |  |  |  |
| aag | gtg | ctg | ccc | aag | cac | agc | ctg | ctg | tac | gag | tac | ttc | acc | gtg | tat | 1680 |
| Lys | Val | Leu | Pro | Lys | His | Ser | Leu | Leu | Tyr | Glu | Tyr | Phe | Thr | Val | Tyr |
| 545 |  |  |  |  | 550 |  |  |  |  | 555 |  |  |  |  | 560 |
| aac | gag | ctg | acc | aaa | gtg | aaa | tac | gtg | acc | gag | gga | atg | aga | aag | ccc | 1728 |
| Asn | Glu | Leu | Thr | Lys | Val | Lys | Tyr | Val | Thr | Glu | Gly | Met | Arg | Lys | Pro |
|  |  |  |  | 565 |  |  |  |  | 570 |  |  |  |  | 575 |  |
| gcc | ttc | ctg | agc | ggc | gag | cag | aaa | aag | gcc | atc | gtg | gac | ctg | ctg | ttc | 1776 |
| Ala | Phe | Leu | Ser | Gly | Glu | Gln | Lys | Lys | Ala | Ile | Val | Asp | Leu | Leu | Phe |
|  |  |  | 580 |  |  |  |  | 585 |  |  |  |  | 590 |  |  |
| aag | acc | aac | cgg | aaa | gtg | acc | gtg | aag | cag | ctg | aaa | gag | gac | tac | ttc | 1824 |
| Lys | Thr | Asn | Arg | Lys | Val | Thr | Val | Lys | Gln | Leu | Lys | Glu | Asp | Tyr | Phe |
| 595 |  |  |  |  | 600 |  |  |  |  | 605 |  |  |  |  |  |
| aag | aaa | atc | gag | tgc | ttc | gac | tcc | gtg | gaa | atc | tcc | ggc | gtg | gaa | gat | 1872 |
| Lys | Lys | Ile | Glu | Cys | Phe | Asp | Ser | Val | Glu | Ile | Ser | Gly | Val | Glu | Asp |
| 610 |  |  |  |  | 615 |  |  |  |  | 620 |  |  |  |  |  |
| cgg | ttc | aac | gcc | tcc | ctg | ggc | aca | tac | cac | gat | ctg | ctg | aaa | att | atc | 1920 |
| Arg | Phe | Asn | Ala | Ser | Leu | Gly | Thr | Tyr | His | Asp | Leu | Leu | Lys | Ile | Ile |
| 625 |  |  |  |  | 630 |  |  |  |  | 635 |  |  |  |  | 640 |
| aag | gac | aag | gac | ttc | ctg | gac | aat | gag | gaa | aac | gag | gac | att | ctg | gaa | 1968 |
| Lys | Asp | Lys | Asp | Phe | Leu | Asp | Asn | Glu | Glu | Asn | Glu | Asp | Ile | Leu | Glu |
|  |  |  |  | 645 |  |  |  |  | 650 |  |  |  |  | 655 |  |
| gat | atc | gtg | ctg | acc | ctg | aca | ctg | ttt | gag | gac | aga | gag | atg | atc | gag | 2016 |
| Asp | Ile | Val | Leu | Thr | Leu | Thr | Leu | Phe | Glu | Asp | Arg | Glu | Met | Ile | Glu |
|  |  |  | 660 |  |  |  |  | 665 |  |  |  |  | 670 |  |  |
| gaa | cgg | ctg | aaa | acc | tat | gcc | cac | ctg | ttc | gac | gac | aaa | gtg | atg | aag | 2064 |
| Glu | Arg | Leu | Lys | Thr | Tyr | Ala | His | Leu | Phe | Asp | Asp | Lys | Val | Met | Lys |
|  |  | 675 |  |  |  |  | 680 |  |  |  |  | 685 |  |  |  |
| cag | ctg | aag | cgg | cgg | aga | tac | acc | ggc | tgg | ggc | agg | ctg | agc | cgg | aag | 2112 |
| Gln | Leu | Lys | Arg | Arg | Arg | Tyr | Thr | Gly | Trp | Gly | Arg | Leu | Ser | Arg | Lys |
|  | 690 |  |  |  |  | 695 |  |  |  |  | 700 |  |  |  |  |
| ctg | atc | aac | ggc | atc | cgg | gac | aag | cag | tcc | ggc | aag | aca | atc | ctg | gat | 2160 |
| Leu | Ile | Asn | Gly | Ile | Arg | Asp | Lys | Gln | Ser | Gly | Lys | Thr | Ile | Leu | Asp |
| 705 |  |  |  |  | 710 |  |  |  |  | 715 |  |  |  |  | 720 |
| ttc | ctg | aag | tcc | gac | ggc | ttc | gcc | aac | aga | aac | ttc | atg | cag | ctg | atc | 2208 |
| Phe | Leu | Lys | Ser | Asp | Gly | Phe | Ala | Asn | Arg | Asn | Phe | Met | Gln | Leu | Ile |
|  |  |  |  | 725 |  |  |  |  | 730 |  |  |  |  | 735 |  |
| cac | gac | gac | agc | ctg | acc | ttt | aaa | gag | gac | atc | cag | aaa | gcc | cag | gtg | 2256 |
| His | Asp | Asp | Ser | Leu | Thr | Phe | Lys | Glu | Asp | Ile | Gln | Lys | Ala | Gln | Val |
|  |  |  | 740 |  |  |  |  | 745 |  |  |  |  | 750 |  |  |
| tcc | ggc | cag | ggc | gat | agc | ctg | cac | gag | cac | att | gcc | aat | ctg | gcc | ggc | 2304 |
| Ser | Gly | Gln | Gly | Asp | Ser | Leu | His | Glu | His | Ile | Ala | Asn | Leu | Ala | Gly |
|  |  | 755 |  |  |  |  | 760 |  |  |  |  | 765 |  |  |  |
| agc | ccc | gcc | att | aag | aag | ggc | atc | ctg | cag | aca | gtg | aag | gtg | gtg | gac | 2352 |
| Ser | Pro | Ala | Ile | Lys | Lys | Gly | Ile | Leu | Gln | Thr | Val | Lys | Val | Val | Asp |
|  | 770 |  |  |  |  | 775 |  |  |  |  | 780 |  |  |  |  |
| gag | ctc | gtg | aaa | gtg | atg | ggc | cgg | cac | aag | ccc | gag | aac | atc | gtg | atc | 2400 |
| Glu | Leu | Val | Lys | Val | Met | Gly | Arg | His | Lys | Pro | Glu | Asn | Ile | Val | Ile |
| 785 |  |  |  |  | 790 |  |  |  |  | 795 |  |  |  |  | 800 |
| gaa | atg | gcc | aga | gag | aac | cag | acc | acc | cag | aag | gga | cag | aag | aac | agc | 2448 |

```
           Glu  Met  Ala  Arg  Glu  Asn  Gln  Thr  Thr  Gln  Lys  Gly  Gln  Lys  Asn  Ser
                          805                           810                      815 cgc  gag  aga  atg  aag  cgg  atc  gaa  gag  ggc  atc  aaa  gag  ctg  ggc  agc                2496
Arg  Glu  Arg  Met  Lys  Arg  Ile  Glu  Glu  Gly  Ile  Lys  Glu  Leu  Gly  Ser
          820                           825                      830 cag  atc  ctg  aaa  gaa  cac  ccc  gtg  gaa  aac  acc  cag  ctg  cag  aac  gag                2544
Gln  Ile  Leu  Lys  Glu  His  Pro  Val  Glu  Asn  Thr  Gln  Leu  Gln  Asn  Glu
               835                           840                      845 aag  ctg  tac  ctg  tac  tac  ctg  cag  aat  ggg  cgg  gat  atg  tac  gtg  gac                2592
Lys  Leu  Tyr  Leu  Tyr  Tyr  Leu  Gln  Asn  Gly  Arg  Asp  Met  Tyr  Val  Asp
     850                           855                      860 cag  gaa  ctg  gac  atc  aac  cgg  ctg  tcc  gac  tac  gat  gtg  gac  cat  atc                2640
Gln  Glu  Leu  Asp  Ile  Asn  Arg  Leu  Ser  Asp  Tyr  Asp  Val  Asp  His  Ile
865                      870                           875                      880 gtg  cct  cag  agc  ttt  ctg  aag  gac  gac  tcc  atc  gac  aac  aag  gtg  ctg                2688
Val  Pro  Gln  Ser  Phe  Leu  Lys  Asp  Asp  Ser  Ile  Asp  Asn  Lys  Val  Leu
                    885                           890                      895 acc  aga  agc  gac  aag  aac  cgg  ggc  aag  agc  gac  aac  gtg  ccc  tcc  gaa                2736
Thr  Arg  Ser  Asp  Lys  Asn  Arg  Gly  Lys  Ser  Asp  Asn  Val  Pro  Ser  Glu
               900                           905                      910 gag  gtc  gtg  aag  aag  atg  aag  aac  tac  tgg  cgg  cag  ctg  ctg  aac  gcc                2784
Glu  Val  Val  Lys  Lys  Met  Lys  Asn  Tyr  Trp  Arg  Gln  Leu  Leu  Asn  Ala
          915                           920                      925 aag  ctg  att  acc  cag  aga  aag  ttc  gac  aat  ctg  acc  aag  gcc  gag  aga                2832
Lys  Leu  Ile  Thr  Gln  Arg  Lys  Phe  Asp  Asn  Leu  Thr  Lys  Ala  Glu  Arg
     930                           935                      940 ggc  ggc  ctg  agc  gaa  ctg  gat  aag  gcc  ggc  ttc  atc  aag  aga  cag  ctg                2880
Gly  Gly  Leu  Ser  Glu  Leu  Asp  Lys  Ala  Gly  Phe  Ile  Lys  Arg  Gln  Leu
945                      950                           955                      960 gtg  gaa  acc  cgg  cag  atc  aca  aag  cac  gtg  gca  cag  atc  ctg  gac  tcc                2928
Val  Glu  Thr  Arg  Gln  Ile  Thr  Lys  His  Val  Ala  Gln  Ile  Leu  Asp  Ser
                    965                           970                      975 cgg  atg  aac  act  aag  tac  gac  gag  aat  gac  aag  ctg  atc  cgg  gaa  gtg                2976
Arg  Met  Asn  Thr  Lys  Tyr  Asp  Glu  Asn  Asp  Lys  Leu  Ile  Arg  Glu  Val
               980                           985                      990 aaa  gtg  atc  acc  ctg  aag  tcc  aag  ctg  gtg  tcc  gat  ttc  cgg  aag  gat                3024
Lys  Val  Ile  Thr  Leu  Lys  Ser  Lys  Leu  Val  Ser  Asp  Phe  Arg  Lys  Asp
          995                          1000                     1005 ttc  cag  ttt  tac  aaa  gtg  cgc  gag  atc  aac  aac  tac  cac  cac  gcc                     3069
Phe  Gln  Phe  Tyr  Lys  Val  Arg  Glu  Ile  Asn  Asn  Tyr  His  His  Ala
     1010                          1015                     1020 cac  gac  gcc  tac  ctg  aac  gcc  gtc  gtg  gga  acc  gcc  ctg  atc  aaa                     3114
His  Asp  Ala  Tyr  Leu  Asn  Ala  Val  Val  Gly  Thr  Ala  Leu  Ile  Lys
1025                          1030                     1035 aag  tac  cct  aag  ctg  gaa  agc  gag  ttc  gtg  tac  ggc  gac  tac  aag                     3159
Lys  Tyr  Pro  Lys  Leu  Glu  Ser  Glu  Phe  Val  Tyr  Gly  Asp  Tyr  Lys
     1040                          1045                     1050 gtg  tac  gac  gtg  cgg  aag  atg  atc  gcc  aag  agc  gag  cag  gaa  atc                     3204
Val  Tyr  Asp  Val  Arg  Lys  Met  Ile  Ala  Lys  Ser  Glu  Gln  Glu  Ile
     1055                          1060                     1065 ggc  aag  gct  acc  gcc  aag  tac  ttc  ttc  tac  agc  aac  atc  atg  aac                     3249
Gly  Lys  Ala  Thr  Ala  Lys  Tyr  Phe  Phe  Tyr  Ser  Asn  Ile  Met  Asn
     1070                          1075                     1080 ttt  ttc  aag  acc  gag  att  acc  ctg  gcc  aac  ggc  gag  atc  cgg  aag                     3294
Phe  Phe  Lys  Thr  Glu  Ile  Thr  Leu  Ala  Asn  Gly  Glu  Ile  Arg  Lys
     1085                          1090                     1095 cgg  cct  ctg  atc  gag  aca  aac  ggc  gaa  acc  ggg  gag  atc  gtg  tgg                     3339
Arg  Pro  Leu  Ile  Glu  Thr  Asn  Gly  Glu  Thr  Gly  Glu  Ile  Val  Trp
     1100                          1105                     1110
```

```
gat aag ggc cgg gat ttt gcc acc gtg cgg aaa gtg ctg agc atg    3384
Asp Lys Gly Arg Asp Phe Ala Thr Val Arg Lys Val Leu Ser Met
    1115            1120                1125 ccc caa gtg aat atc gtg aaa aag acc gag gtg cag aca ggc ggc    3429
Pro Gln Val Asn Ile Val Lys Lys Thr Glu Val Gln Thr Gly Gly
    1130            1135                1140 ttc agc aaa gag tct atc ctg ccc aag agg aac agc gat aag ctg    3474
Phe Ser Lys Glu Ser Ile Leu Pro Lys Arg Asn Ser Asp Lys Leu
    1145            1150                1155 atc gcc aga aag aag gac tgg gac cct aag aag tac ggc ggc ttc    3519
Ile Ala Arg Lys Lys Asp Trp Asp Pro Lys Lys Tyr Gly Gly Phe
    1160            1165                1170 gac agc ccc acc gtg gcc tat tct gtg ctg gtg gtg gcc aaa gtg    3564
Asp Ser Pro Thr Val Ala Tyr Ser Val Leu Val Val Ala Lys Val
    1175            1180                1185 gaa aag ggc aag tcc aag aaa ctg aag agt gtg aaa gag ctg ctg    3609
Glu Lys Gly Lys Ser Lys Lys Leu Lys Ser Val Lys Glu Leu Leu
    1190            1195                1200 ggg atc acc atc atg gaa aga agc agc ttc gag aag aat ccc atc    3654
Gly Ile Thr Ile Met Glu Arg Ser Ser Phe Glu Lys Asn Pro Ile
    1205            1210                1215 gac ttt ctg gaa gcc aag ggc tac aaa gaa gtg aaa aag gac ctg    3699
Asp Phe Leu Glu Ala Lys Gly Tyr Lys Glu Val Lys Lys Asp Leu
    1220            1225                1230 atc atc aag ctg cct aag tac tcc ctg ttc gag ctg gaa aac ggc    3744
Ile Ile Lys Leu Pro Lys Tyr Ser Leu Phe Glu Leu Glu Asn Gly
    1235            1240                1245 cgg aag aga atg ctg gcc tct gcc ggc gaa ctg cag aag gga aac    3789
Arg Lys Arg Met Leu Ala Ser Ala Gly Glu Leu Gln Lys Gly Asn
    1250            1255                1260 gaa ctg gcc ctg ccc tcc aaa tat gtg aac ttc ctg tac ctg gcc    3834
Glu Leu Ala Leu Pro Ser Lys Tyr Val Asn Phe Leu Tyr Leu Ala
    1265            1270                1275 agc cac tat gag aag ctg aag ggc tcc ccc gag gat aat gag cag    3879
Ser His Tyr Glu Lys Leu Lys Gly Ser Pro Glu Asp Asn Glu Gln
    1280            1285                1290 aaa cag ctg ttt gtg gaa cag cac aag cac tac ctg gac gag atc    3924
Lys Gln Leu Phe Val Glu Gln His Lys His Tyr Leu Asp Glu Ile
    1295            1300                1305 atc gag cag atc agc gag ttc tcc aag aga gtg atc ctg gcc gac    3969
Ile Glu Gln Ile Ser Glu Phe Ser Lys Arg Val Ile Leu Ala Asp
    1310            1315                1320 gct aat ctg gac aaa gtg ctg tcc gcc tac aac aag cac cgg gat    4014
Ala Asn Leu Asp Lys Val Leu Ser Ala Tyr Asn Lys His Arg Asp
    1325            1330                1335 aag ccc atc aga gag cag gcc gag aat atc atc cac ctg ttt acc    4059
Lys Pro Ile Arg Glu Gln Ala Glu Asn Ile Ile His Leu Phe Thr
    1340            1345                1350 ctg acc aat ctg gga gcc cct gcc gcc ttc aag tac ttt gac acc    4104
Leu Thr Asn Leu Gly Ala Pro Ala Ala Phe Lys Tyr Phe Asp Thr
    1355            1360                1365 acc atc gac cgg aag agg tac acc agc acc aaa gag gtg ctg gac    4149
Thr Ile Asp Arg Lys Arg Tyr Thr Ser Thr Lys Glu Val Leu Asp
    1370            1375                1380 gcc acc ctg atc cac cag agc atc acc ggc ctg tac gag aca cgg    4194
Ala Thr Leu Ile His Gln Ser Ile Thr Gly Leu Tyr Glu Thr Arg
    1385            1390                1395 atc gac ctg tct cag ctg gga ggc gac aaa agg ccg gcg gcc acg    4239
Ile Asp Leu Ser Gln Leu Gly Gly Asp Lys Arg Pro Ala Ala Thr
    1400            1405                1410
```

-continued

```
aaa aag gcc ggc cag gca aaa     aag aaa aag aaa taa                    4275
Lys Lys Ala Gly Gln Ala Lys     Lys Lys Lys Lys
    1415                1420
```

<210> SEQ ID NO 51
<211> LENGTH: 1424
<212> TYPE: PRT
<213> ORGANISM: Homo sapiens

<400> SEQUENCE: 51

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Ile His Gly Val Pro Ala Ala Asp Lys Lys Tyr Ser Ile Gly Leu
        35                  40                  45

Asp Ile Gly Thr Asn Ser Val Gly Trp Ala Val Ile Thr Asp Glu Tyr
    50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Arg Tyr Thr
            100                 105                 110

Arg Arg Lys Asn Arg Ile Cys Tyr Leu Gln Glu Ile Phe Ser Asn Glu
        115                 120                 125

Met Ala Lys Val Asp Asp Ser Phe Phe His Arg Leu Glu Glu Ser Phe
    130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
        195                 200                 205

Ile Glu Gly Asp Leu Asn Pro Asp Asn Ser Asp Val Asp Lys Leu Phe
    210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
            260                 265                 270

Lys Asn Gly Leu Phe Gly Asn Leu Ile Ala Leu Ser Leu Gly Leu Thr
        275                 280                 285

Pro Asn Phe Lys Ser Asn Phe Asp Leu Ala Glu Asp Ala Lys Leu Gln
    290                 295                 300

Leu Ser Lys Asp Thr Tyr Asp Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
            340                 345                 350

```
Lys Ala Pro Leu Ser Ala Ser Met Ile Lys Arg Tyr Asp Glu His His
            355                 360                 365

Gln Asp Leu Thr Leu Leu Lys Ala Leu Val Arg Gln Gln Leu Pro Glu
    370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
            420                 425                 430

Asn Arg Glu Asp Leu Leu Arg Lys Gln Arg Thr Phe Asp Asn Gly Ser
        435                 440                 445

Ile Pro His Gln Ile His Leu Gly Glu Leu His Ala Ile Leu Arg Arg
    450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
            500                 505                 510

Thr Pro Trp Asn Phe Glu Glu Val Val Asp Lys Gly Ala Ser Ala Gln
    515                 520                 525

Ser Phe Ile Glu Arg Met Thr Asn Phe Asp Lys Asn Leu Pro Asn Glu
    530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
            580                 585                 590

Lys Thr Asn Arg Lys Val Thr Val Lys Gln Leu Lys Glu Asp Tyr Phe
    595                 600                 605

Lys Lys Ile Glu Cys Phe Asp Ser Val Glu Ile Ser Gly Val Glu Asp
    610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                645                 650                 655

Asp Ile Val Leu Thr Leu Thr Leu Phe Glu Asp Arg Glu Met Ile Glu
            660                 665                 670

Glu Arg Leu Lys Thr Tyr Ala His Leu Phe Asp Asp Lys Val Met Lys
    675                 680                 685

Gln Leu Lys Arg Arg Arg Tyr Thr Gly Trp Gly Arg Leu Ser Arg Lys
    690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
            740                 745                 750

Ser Gly Gln Gly Asp Ser Leu His Glu His Ile Ala Asn Leu Ala Gly
    755                 760                 765

Ser Pro Ala Ile Lys Lys Gly Ile Leu Gln Thr Val Lys Val Val Asp
```

```
            770                 775                 780
Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                805                 810                 815

Arg Glu Arg Met Lys Arg Ile Glu Glu Gly Ile Lys Glu Leu Gly Ser
                820                 825                 830

Gln Ile Leu Lys Glu His Pro Val Glu Asn Thr Gln Leu Gln Asn Glu
                835                 840                 845

Lys Leu Tyr Leu Tyr Tyr Leu Gln Asn Gly Arg Asp Met Tyr Val Asp
                850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
                885                 890                 895

Thr Arg Ser Asp Lys Asn Arg Gly Lys Ser Asp Asn Val Pro Ser Glu
                900                 905                 910

Glu Val Val Lys Lys Met Lys Asn Tyr Trp Arg Gln Leu Leu Asn Ala
                915                 920                 925

Lys Leu Ile Thr Gln Arg Lys Phe Asp Asn Leu Thr Lys Ala Glu Arg
930                 935                 940

Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
                965                 970                 975

Arg Met Asn Thr Lys Tyr Asp Glu Asn Asp Lys Leu Ile Arg Glu Val
                980                 985                 990

Lys Val Ile Thr Leu Lys Ser Lys Leu Val Ser Asp Phe Arg Lys Asp
                995                1000                1005

Phe Gln Phe Tyr Lys Val Arg Glu Ile Asn Asn Tyr His His Ala
1010                1015                1020

His Asp Ala Tyr Leu Asn Ala Val Val Gly Thr Ala Leu Ile Lys
1025                1030                1035

Lys Tyr Pro Lys Leu Glu Ser Glu Phe Val Tyr Gly Asp Tyr Lys
1040                1045                1050

Val Tyr Asp Val Arg Lys Met Ile Ala Lys Ser Glu Gln Glu Ile
1055                1060                1065

Gly Lys Ala Thr Ala Lys Tyr Phe Phe Tyr Ser Asn Ile Met Asn
1070                1075                1080

Phe Phe Lys Thr Glu Ile Thr Leu Ala Asn Gly Glu Ile Arg Lys
1085                1090                1095

Arg Pro Leu Ile Glu Thr Asn Gly Glu Thr Gly Glu Ile Val Trp
1100                1105                1110

Asp Lys Gly Arg Asp Phe Ala Thr Val Arg Lys Val Leu Ser Met
1115                1120                1125

Pro Gln Val Asn Ile Val Lys Lys Thr Glu Val Gln Thr Gly Gly
1130                1135                1140

Phe Ser Lys Glu Ser Ile Leu Pro Lys Arg Asn Ser Asp Lys Leu
1145                1150                1155

Ile Ala Arg Lys Lys Asp Trp Asp Pro Lys Lys Tyr Gly Gly Phe
1160                1165                1170

Asp Ser Pro Thr Val Ala Tyr Ser Val Leu Val Val Ala Lys Val
1175                1180                1185
```

Glu Lys Gly Lys Ser Lys Lys Leu Lys Ser Val Lys Glu Leu Leu
    1190            1195                1200

Gly Ile Thr Ile Met Glu Arg Ser Ser Phe Glu Lys Asn Pro Ile
    1205            1210                1215

Asp Phe Leu Glu Ala Lys Gly Tyr Lys Glu Val Lys Lys Asp Leu
    1220            1225                1230

Ile Ile Lys Leu Pro Lys Tyr Ser Leu Phe Glu Leu Glu Asn Gly
    1235            1240                1245

Arg Lys Arg Met Leu Ala Ser Ala Gly Glu Leu Gln Lys Gly Asn
    1250            1255                1260

Glu Leu Ala Leu Pro Ser Lys Tyr Val Asn Phe Leu Tyr Leu Ala
    1265            1270                1275

Ser His Tyr Glu Lys Leu Lys Gly Ser Pro Glu Asp Asn Glu Gln
    1280            1285                1290

Lys Gln Leu Phe Val Glu Gln His Lys His Tyr Leu Asp Glu Ile
    1295            1300                1305

Ile Glu Gln Ile Ser Glu Phe Ser Lys Arg Val Ile Leu Ala Asp
    1310            1315                1320

Ala Asn Leu Asp Lys Val Leu Ser Ala Tyr Asn Lys His Arg Asp
    1325            1330                1335

Lys Pro Ile Arg Glu Gln Ala Glu Asn Ile Ile His Leu Phe Thr
    1340            1345                1350

Leu Thr Asn Leu Gly Ala Pro Ala Ala Phe Lys Tyr Phe Asp Thr
    1355            1360                1365

Thr Ile Asp Arg Lys Arg Tyr Thr Ser Thr Lys Glu Val Leu Asp
    1370            1375                1380

Ala Thr Leu Ile His Gln Ser Ile Thr Gly Leu Tyr Glu Thr Arg
    1385            1390                1395

Ile Asp Leu Ser Gln Leu Gly Gly Asp Lys Arg Pro Ala Ala Thr
    1400            1405                1410

Lys Lys Ala Gly Gln Ala Lys Lys Lys Lys Lys
    1415            1420

<210> SEQ ID NO 52
<211> LENGTH: 45
<212> TYPE: DNA
<213> ORGANISM: Artificial
<220> FEATURE:
<223> OTHER INFORMATION: Primer

<400> SEQUENCE: 52
actgagaacc tgtacttcca gggaatggac tataaggacc acgac        45

<210> SEQ ID NO 53
<211> LENGTH: 46
<212> TYPE: DNA
<213> ORGANISM: Artificial
<220> FEATURE:
<223> OTHER INFORMATION: Primer

<400> SEQUENCE: 53 gggcgggat caatcaatca ttatttcttt ttcttttttg cctggc        46

<210> SEQ ID NO 54
<211> LENGTH: 21
<212> TYPE: DNA
<213> ORGANISM: Artificial
<220> FEATURE:

<223> OTHER INFORMATION: Synthetic

<400> SEQUENCE: 54
tcttcaagga cgacggcaac t                                         21

<210> SEQ ID NO 55
<211> LENGTH: 19
<212> TYPE: DNA
<213> ORGANISM: Artificial
<220> FEATURE:
<223> OTHER INFORMATION: Synthetic

<400> SEQUENCE: 55
tcgccctcga acttcacct                                            19

<210> SEQ ID NO 56
<211> LENGTH: 25
<212> TYPE: DNA
<213> ORGANISM: Artificial
<220> FEATURE:
<223> OTHER INFORMATION: Primer

<400> SEQUENCE: 56
cacatgaagc agcacgactt cttca                                     25

<210> SEQ ID NO 57
<211> LENGTH: 25
<212> TYPE: DNA
<213> ORGANISM: Artificial
<220> FEATURE:
<223> OTHER INFORMATION: Primer

<400> SEQUENCE: 57
ctcgatgttg tggcggatct tgaag                                     25

<210> SEQ ID NO 58
<211> LENGTH: 35
<212> TYPE: DNA
<213> ORGANISM: Artificial
<220> FEATURE:
<223> OTHER INFORMATION: Primer

<400> SEQUENCE: 58
atatccatgg ggattgaaca agatggattg cacgc                          35

<210> SEQ ID NO 59
<211> LENGTH: 35
<212> TYPE: DNA
<213> ORGANISM: Artificial
<220> FEATURE:
<223> OTHER INFORMATION: Primer

<400> SEQUENCE: 59
atatggatcc cggaagaact cgtcaagaag gcgat                          35

<210> SEQ ID NO 60
<211> LENGTH: 214
<212> TYPE: DNA
<213> ORGANISM: Artificial
<220> FEATURE:
<223> OTHER INFORMATION: Primer

<400> SEQUENCE: 60
gctcttgtca ttgtgcttcg catgattacg aattcagatc tcgatcccgc gaaattaata      60
cgactcacta tagggagacc acaacggttt ccctctagaa ataatttgt ttaactttaa     120

| | |
|---|---|
| gaaggagata tacatatgaa agatcatctc atccacaatc atcacaaaca tgagcacgct | 180 |
| catgccgaac atactgagaa cctgtacttc cagg | 214 |

<210> SEQ ID NO 61
<211> LENGTH: 178
<212> TYPE: DNA
<213> ORGANISM: Artificial
<220> FEATURE:
<223> OTHER INFORMATION: Primer

<400> SEQUENCE: 61

| | |
|---|---|
| aatgattgat tgatccccgc ccagctgagt tggctgctgc caccgctgag caataactag | 60 |
| cataacccct tggggcctct aaacgggtct tgaggggttt tttgctgaaa ggaggaacta | 120 |
| tatccggata acctcgagct gcaggcatgc aagcttggcg aagcacaatg acaagagc | 178 |

<210> SEQ ID NO 62
<211> LENGTH: 20
<212> TYPE: DNA
<213> ORGANISM: Artificial
<220> FEATURE:
<223> OTHER INFORMATION: Primer

<400> SEQUENCE: 62

| | |
|---|---|
| gctcttgtca ttgtgcttcg | 20 |

<210> SEQ ID NO 63
<211> LENGTH: 22
<212> TYPE: PRT
<213> ORGANISM: Artificial
<220> FEATURE:
<223> OTHER INFORMATION: Synthetic

<400> SEQUENCE: 63

Lys Lys Leu Phe Lys Lys Ile Leu Lys Tyr Leu Lys Lys Leu Phe Lys
1               5                   10                  15

Lys Ile Leu Lys Tyr Leu
            20

<210> SEQ ID NO 64
<211> LENGTH: 17
<212> TYPE: PRT
<213> ORGANISM: Artificial
<220> FEATURE:
<223> OTHER INFORMATION: Synthetic

<400> SEQUENCE: 64

Thr Arg Gln Ala Arg Arg Asn Arg Arg Arg Arg Trp Arg Glu Arg Gln
1               5                   10                  15

Arg

<210> SEQ ID NO 65
<211> LENGTH: 9
<212> TYPE: PRT
<213> ORGANISM: Artificial
<220> FEATURE:
<223> OTHER INFORMATION: Synthetic

<400> SEQUENCE: 65

Arg Arg Arg Arg Arg Arg Arg Arg Arg
1               5

<210> SEQ ID NO 66

```
<211> LENGTH: 9
<212> TYPE: PRT
<213> ORGANISM: Artificial
<220> FEATURE:
<223> OTHER INFORMATION: Synthetic: All amino acid residues are in D-
      form

<400> SEQUENCE: 66

Arg Arg Arg Arg Arg Arg Arg Arg Arg
1               5

<210> SEQ ID NO 67
<211> LENGTH: 12
<212> TYPE: PRT
<213> ORGANISM: Artificial
<220> FEATURE:
<223> OTHER INFORMATION: Synthetic

<400> SEQUENCE: 67

Arg Arg Arg Arg Arg Arg Arg Arg Arg Arg Arg Arg
1               5                   10

<210> SEQ ID NO 68
<211> LENGTH: 9
<212> TYPE: PRT
<213> ORGANISM: Artificial
<220> FEATURE:
<223> OTHER INFORMATION: Synthetic

<400> SEQUENCE: 68

Lys Lys Lys Lys Lys Lys Lys Lys Lys
1               5

<210> SEQ ID NO 69
<211> LENGTH: 18
<212> TYPE: PRT
<213> ORGANISM: Artificial
<220> FEATURE:
<223> OTHER INFORMATION: Synthetic

<400> SEQUENCE: 69

Lys Lys Lys Lys Lys Lys Lys Lys Lys Lys Lys Lys Lys Lys Lys Lys
1               5                   10                  15

Lys Lys

<210> SEQ ID NO 70
<211> LENGTH: 16
<212> TYPE: PRT
<213> ORGANISM: Artificial
<220> FEATURE:
<223> OTHER INFORMATION: Synthetic

<400> SEQUENCE: 70

Arg Gln Ile Lys Ile Phe Phe Gln Asn Arg Arg Met Lys Phe Lys Lys
1               5                   10                  15

<210> SEQ ID NO 71
<211> LENGTH: 16
<212> TYPE: PRT
<213> ORGANISM: Artificial
<220> FEATURE:
<223> OTHER INFORMATION: Synthetic

<400> SEQUENCE: 71

Arg Lys Lys Arg Arg Arg Glu Ser Arg Lys Lys Arg Arg Arg Glu Ser
1               5                   10                  15
```

<210> SEQ ID NO 72
<211> LENGTH: 8
<212> TYPE: PRT
<213> ORGANISM: Artificial
<220> FEATURE:
<223> OTHER INFORMATION: Synthetic

<400> SEQUENCE: 72

Gly Arg Lys Arg Lys Lys Arg Thr
1               5

<210> SEQ ID NO 73
<211> LENGTH: 13
<212> TYPE: PRT
<213> ORGANISM: Artificial
<220> FEATURE:
<223> OTHER INFORMATION: Synthetic

<400> SEQUENCE: 73

Gly Arg Arg Arg Arg Arg Arg Arg Arg Pro Pro Gln
1               5                   10

<210> SEQ ID NO 74
<211> LENGTH: 9
<212> TYPE: PRT
<213> ORGANISM: Artificial
<220> FEATURE:
<223> OTHER INFORMATION: Synthetic

<400> SEQUENCE: 74

Arg Arg Arg Gln Arg Arg Lys Lys Arg
1               5

<210> SEQ ID NO 75
<211> LENGTH: 16
<212> TYPE: PRT
<213> ORGANISM: Artificial
<220> FEATURE:
<223> OTHER INFORMATION: Synthetic

<400> SEQUENCE: 75

Gly Leu Arg Lys Arg Leu Arg Lys Phe Arg Asn Lys Ile Lys Glu Lys
1               5                   10                  15

<210> SEQ ID NO 76
<211> LENGTH: 18
<212> TYPE: PRT
<213> ORGANISM: Artificial
<220> FEATURE:
<223> OTHER INFORMATION: Synthetic

<400> SEQUENCE: 76

Lys Ala Leu Lys Lys Leu Leu Ala Lys Trp Leu Ala Ala Ala Lys Ala
1               5                   10                  15

Leu Leu

<210> SEQ ID NO 77
<211> LENGTH: 18
<212> TYPE: PRT
<213> ORGANISM: Artificial
<220> FEATURE:
<223> OTHER INFORMATION: Synthetic

<400> SEQUENCE: 77

Gln Leu Ala Leu Gln Leu Ala Leu Gln Ala Leu Gln Ala Ala Leu Gln
1               5                   10                  15

Leu Ala

<210> SEQ ID NO 78
<211> LENGTH: 18
<212> TYPE: PRT
<213> ORGANISM: Artificial
<220> FEATURE:
<223> OTHER INFORMATION: Synthetic

<400> SEQUENCE: 78

Leu Lys Thr Leu Ala Thr Ala Leu Thr Lys Leu Ala Lys Thr Leu Thr
1               5                   10                  15

Thr Leu

<210> SEQ ID NO 79
<211> LENGTH: 15
<212> TYPE: PRT
<213> ORGANISM: Artificial
<220> FEATURE:
<223> OTHER INFORMATION: Synthetic

<400> SEQUENCE: 79

Arg Ala Trp Met Arg Trp Tyr Ser Pro Thr Thr Arg Arg Tyr Gly
1               5                   10                  15

<210> SEQ ID NO 80
<211> LENGTH: 18
<212> TYPE: PRT
<213> ORGANISM: Artificial
<220> FEATURE:
<223> OTHER INFORMATION: Synthetic

<400> SEQUENCE: 80

Leu Leu Ile Ile Leu Arg Arg Arg Ile Arg Lys Gln Ala His Ala His
1               5                   10                  15

Ser Lys

<210> SEQ ID NO 81
<211> LENGTH: 16
<212> TYPE: PRT
<213> ORGANISM: Artificial
<220> FEATURE:
<223> OTHER INFORMATION: Synthetic

<400> SEQUENCE: 81

Arg Gln Ile Arg Ile Trp Phe Gln Asn Arg Arg Met Arg Trp Arg Arg
1               5                   10                  15

<210> SEQ ID NO 82
<211> LENGTH: 22
<212> TYPE: PRT
<213> ORGANISM: Artificial
<220> FEATURE:
<223> OTHER INFORMATION: Synthetic

<400> SEQUENCE: 82

Met Val Thr Val Leu Phe Arg Arg Leu Arg Ile Arg Arg Ala Cys Gly
1               5                   10                  15

Pro Pro Arg Val Arg Val
            20

<210> SEQ ID NO 83
<211> LENGTH: 18
<212> TYPE: PRT

<213> ORGANISM: Artificial
<220> FEATURE:
<223> OTHER INFORMATION: Synthetic

<400> SEQUENCE: 83

Val Arg Leu Pro Pro Val Arg Leu Pro Pro Val Arg Leu Pro
1               5                   10                  15

Pro Pro

<210> SEQ ID NO 84
<211> LENGTH: 14
<212> TYPE: PRT
<213> ORGANISM: Artificial
<220> FEATURE:
<223> OTHER INFORMATION: Synthetic

<400> SEQUENCE: 84

Leu Leu Leu Phe Leu Leu Lys Lys Arg Lys Lys Arg Lys Tyr
1               5                   10

<210> SEQ ID NO 85
<211> LENGTH: 23
<212> TYPE: PRT
<213> ORGANISM: Artificial
<220> FEATURE:
<223> OTHER INFORMATION: Synthetic

<400> SEQUENCE: 85

Ser Tyr Phe Ile Leu Arg Arg Arg Lys Arg Phe Pro Tyr Phe Phe
1               5                   10                  15

Thr Asp Val Arg Val Ala Ala
            20

<210> SEQ ID NO 86
<211> LENGTH: 17
<212> TYPE: PRT
<213> ORGANISM: Artificial
<220> FEATURE:
<223> OTHER INFORMATION: Synthetic

<400> SEQUENCE: 86

Arg Ala Gly Leu Gln Phe Pro Val Gly Arg Val His Arg Leu Leu Arg
1               5                   10                  15

Lys

<210> SEQ ID NO 87
<211> LENGTH: 18
<212> TYPE: PRT
<213> ORGANISM: Artificial
<220> FEATURE:
<223> OTHER INFORMATION: Synthetic

<400> SEQUENCE: 87

Ile Ala Ala Arg Ile Lys Leu Arg Ser Arg Gln His Ile Lys Leu Arg
1               5                   10                  15

His Leu

<210> SEQ ID NO 88
<211> LENGTH: 23
<212> TYPE: PRT
<213> ORGANISM: Artificial
<220> FEATURE:
<223> OTHER INFORMATION: Synthetic

<400> SEQUENCE: 88

```
Ser Tyr Asp Asp Leu Arg Arg Arg Lys Arg Phe Pro Tyr Phe Phe
1               5                   10                  15

Thr Asp Val Arg Val Ala Ala
            20
```

<210> SEQ ID NO 89
<211> LENGTH: 26
<212> TYPE: PRT
<213> ORGANISM: Artificial
<220> FEATURE:
<223> OTHER INFORMATION: Synthetic

<400> SEQUENCE: 89

```
Lys Lys Ala Leu Leu Ala Leu Ala Leu His His Leu Ala His Leu Ala
1               5                   10                  15

Leu His Leu Ala Leu Ala Leu Lys Lys Ala
            20                  25
```

<210> SEQ ID NO 90
<211> LENGTH: 20
<212> TYPE: PRT
<213> ORGANISM: Artificial
<220> FEATURE:
<223> OTHER INFORMATION: Synthetic

<400> SEQUENCE: 90

```
Gly Leu Phe Lys Ala Leu Leu Lys Leu Leu Lys Ser Leu Trp Lys Leu
1               5                   10                  15

Leu Leu Lys Ala
            20
```

<210> SEQ ID NO 91
<211> LENGTH: 27
<212> TYPE: PRT
<213> ORGANISM: Artificial
<220> FEATURE:
<223> OTHER INFORMATION: Synthetic

<400> SEQUENCE: 91

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 92
<211> LENGTH: 40
<212> TYPE: PRT
<213> ORGANISM: Artificial
<220> FEATURE:
<223> OTHER INFORMATION: Synthetic

<400> SEQUENCE: 92

```
Gly Leu Phe Lys Ala Leu Leu Lys Leu Leu Lys Ser Leu Trp Lys Leu
1               5                   10                  15

Leu Leu Lys Ala Gly Leu Phe Lys Ala Leu Leu Lys Leu Leu Lys Ser
            20                  25                  30

Leu Trp Lys Leu Leu Leu Lys Ala
        35                  40
```

<210> SEQ ID NO 93
<211> LENGTH: 16
<212> TYPE: PRT
<213> ORGANISM: Artificial

<220> FEATURE:
<223> OTHER INFORMATION: Synthetic

<400> SEQUENCE: 93

```
Arg Gln Ile Lys Ile Trp Phe Pro Asn Arg Arg Met Lys Trp Lys Lys
1               5                   10                  15
```

<210> SEQ ID NO 94
<211> LENGTH: 15
<212> TYPE: PRT
<213> ORGANISM: Artificial
<220> FEATURE:
<223> OTHER INFORMATION: Synthetic

<400> SEQUENCE: 94

```
Gln Ile Lys Ile Trp Phe Gln Asn Arg Arg Met Lys Trp Lys Lys
1               5                   10                  15
```

<210> SEQ ID NO 95
<211> LENGTH: 13
<212> TYPE: PRT
<213> ORGANISM: Artificial
<220> FEATURE:
<223> OTHER INFORMATION: Synthetic

<400> SEQUENCE: 95

```
Lys Met Asp Cys Arg Trp Arg Trp Lys Cys Cys Lys Lys
1               5                   10
```

<210> SEQ ID NO 96
<211> LENGTH: 12
<212> TYPE: PRT
<213> ORGANISM: Artificial
<220> FEATURE:
<223> OTHER INFORMATION: Synthetic

<400> SEQUENCE: 96

```
Met Asp Cys Arg Trp Arg Trp Lys Cys Cys Lys Lys
1               5                   10
```

<210> SEQ ID NO 97
<211> LENGTH: 14
<212> TYPE: PRT
<213> ORGANISM: Artificial
<220> FEATURE:
<223> OTHER INFORMATION: Synthetic

<400> SEQUENCE: 97

```
Lys Cys Gly Cys Arg Trp Arg Trp Lys Cys Gly Cys Lys Lys
1               5                   10
```

<210> SEQ ID NO 98
<211> LENGTH: 10
<212> TYPE: PRT
<213> ORGANISM: Artificial
<220> FEATURE:
<223> OTHER INFORMATION: Synthetic

<400> SEQUENCE: 98

```
Cys Arg Trp Arg Trp Lys Cys Cys Lys Lys
1               5                   10
```

<210> SEQ ID NO 99
<211> LENGTH: 22
<212> TYPE: PRT
<213> ORGANISM: Artificial
<220> FEATURE:

<223> OTHER INFORMATION: Synthetic

<400> SEQUENCE: 99

Thr Lys Arg Arg Ile Thr Pro Lys Asp Val Ile Asp Val Arg Ser Val
1               5                   10                  15

Thr Thr Glu Ile Asn Thr
            20

<210> SEQ ID NO 100
<211> LENGTH: 26
<212> TYPE: PRT
<213> ORGANISM: Artificial
<220> FEATURE:
<223> OTHER INFORMATION: Synthetic

<400> SEQUENCE: 100

Ala Glu Lys Val Asp Pro Val Lys Leu Asn Leu Thr Leu Ser Ala Ala
1               5                   10                  15

Ala Glu Ala Leu Thr Gly Leu Gly Asp Lys
            20                  25

<210> SEQ ID NO 101
<211> LENGTH: 22
<212> TYPE: PRT
<213> ORGANISM: Artificial
<220> FEATURE:
<223> OTHER INFORMATION: Synthetic

<400> SEQUENCE: 101

Thr Lys Arg Arg Ile Thr Pro Lys Asp Val Ile Asp Val Arg Ser Val
1               5                   10                  15

Thr Thr Lys Ile Asn Thr
            20

<210> SEQ ID NO 102
<211> LENGTH: 28
<212> TYPE: PRT
<213> ORGANISM: Artificial
<220> FEATURE:
<223> OTHER INFORMATION: Synthetic

<400> SEQUENCE: 102

His His His His His His Thr Lys Arg Arg Ile Thr Pro Lys Asp Val
1               5                   10                  15

Ile Asp Val Arg Ser Val Thr Thr Glu Ile Asn Thr
            20                  25

<210> SEQ ID NO 103
<211> LENGTH: 22
<212> TYPE: PRT
<213> ORGANISM: Artificial
<220> FEATURE:
<223> OTHER INFORMATION: Synthetic

<400> SEQUENCE: 103

Met Val Arg Arg Phe Leu Val Thr Leu Arg Ile Arg Arg Ala Cys Gly
1               5                   10                  15

Pro Pro Arg Val Arg Val
            20

<210> SEQ ID NO 104
<211> LENGTH: 25
<212> TYPE: PRT
<213> ORGANISM: Artificial

```
<220> FEATURE:
<223> OTHER INFORMATION: Synthetic

<400> SEQUENCE: 104

Gly Thr Lys Met Ile Phe Val Gly Ile Lys Lys Lys Glu Glu Arg Ala
1               5                   10                  15

Asp Leu Ile Ala Tyr Leu Lys Lys Ala
            20                  25

<210> SEQ ID NO 105
<211> LENGTH: 22
<212> TYPE: PRT
<213> ORGANISM: Artificial
<220> FEATURE:
<223> OTHER INFORMATION: Synthetic

<400> SEQUENCE: 105

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 106
<211> LENGTH: 13
<212> TYPE: PRT
<213> ORGANISM: Artificial
<220> FEATURE:
<223> OTHER INFORMATION: Synthetic

<400> SEQUENCE: 106

Glu Glu Glu Ala Ala Gly Arg Lys Arg Lys Lys Arg Thr
1               5                   10

<210> SEQ ID NO 107
<211> LENGTH: 15
<212> TYPE: PRT
<213> ORGANISM: Artificial
<220> FEATURE:
<223> OTHER INFORMATION: Synthetic

<400> SEQUENCE: 107

Phe Leu Gly Lys Lys Phe Lys Lys Tyr Phe Leu Gln Leu Leu Lys
1               5                   10                  15

<210> SEQ ID NO 108
<211> LENGTH: 23
<212> TYPE: PRT
<213> ORGANISM: Artificial
<220> FEATURE:
<223> OTHER INFORMATION: Synthetic

<400> SEQUENCE: 108

Phe Leu Ile Phe Ile Arg Val Ile Cys Ile Val Ile Ala Lys Leu Lys
1               5                   10                  15

Ala Asn Leu Met Cys Lys Thr
            20

<210> SEQ ID NO 109
<211> LENGTH: 16
<212> TYPE: PRT
<213> ORGANISM: Artificial
<220> FEATURE:
<223> OTHER INFORMATION: Synthetic

<400> SEQUENCE: 109
```

```
Tyr Ile Val Leu Arg Arg Arg Lys Arg Val Asn Thr Lys Arg Ser
1               5                   10                  15

<210> SEQ ID NO 110
<211> LENGTH: 16
<212> TYPE: PRT
<213> ORGANISM: Artificial
<220> FEATURE:
<223> OTHER INFORMATION: Synthetic

<400> SEQUENCE: 110

Lys Thr Val Leu Leu Arg Lys Leu Leu Lys Leu Leu Val Arg Lys Ile
1               5                   10                  15

<210> SEQ ID NO 111
<211> LENGTH: 16
<212> TYPE: PRT
<213> ORGANISM: Artificial
<220> FEATURE:
<223> OTHER INFORMATION: Synthetic

<400> SEQUENCE: 111

Leu Leu Lys Lys Arg Lys Val Val Arg Leu Ile Lys Phe Leu Leu Lys
1               5                   10                  15

<210> SEQ ID NO 112
<211> LENGTH: 16
<212> TYPE: PRT
<213> ORGANISM: Artificial
<220> FEATURE:
<223> OTHER INFORMATION: Synthetic

<400> SEQUENCE: 112

Lys Lys Ile Cys Thr Arg Lys Pro Arg Phe Met Ser Ala Trp Ala Gln
1               5                   10                  15

<210> SEQ ID NO 113
<211> LENGTH: 23
<212> TYPE: PRT
<213> ORGANISM: Artificial
<220> FEATURE:
<223> OTHER INFORMATION: Synthetic

<400> SEQUENCE: 113

Gly Ile Gly Lys Phe Leu His Ser Ala Lys Lys Trp Gly Lys Ala Phe
1               5                   10                  15

Val Gly Gln Ile Met Asn Cys
                20
```